United States Patent [19]
Darzins et al.

[11] Patent Number: 6,133,016
[45] Date of Patent: *Oct. 17, 2000

[54] SPHINGOMONAS BIODESULFURIZATION CATALYST

[75] Inventors: Aldis Darzins, The Woodlands; Gregory T. Mrachko, Spring, both of Tex.

[73] Assignee: Energy BioSystems Corporation, The Woodlands, Tex.

[*] Notice: This patent is subject to a terminal disclaimer.

[21] Appl. No.: 08/851,089

[22] Filed: May 5, 1997

Related U.S. Application Data

[63] Continuation-in-part of application No. 08/835,292, Apr. 7, 1997, abandoned.

[51] Int. Cl.$^7$ .............................. C12N 1/20; C12N 9/02; C12N 15/00; C07H 21/04
[52] U.S. Cl. ................. 435/252.3; 435/189; 435/254.11; 435/320.1; 536/23.2
[58] Field of Search ................................ 435/189, 320.1, 435/252.3, 254.11; 935/22; 536/23.2

[56] References Cited

U.S. PATENT DOCUMENTS

| | | | |
|---|---|---|---|
| 5,002,888 | 3/1991 | Kilbane, II | 435/282.31 |
| 5,104,801 | 4/1992 | Kilbane, II | 435/282 |
| 5,132,219 | 7/1992 | Kilbane, II | 435/195 |
| 5,198,341 | 3/1993 | Kilbane, II | 435/42 |
| 5,344,778 | 9/1994 | Kilbane, II | 435/262 |
| 5,356,801 | 10/1994 | Rambosek et al. | 435/195 |
| 5,356,813 | 10/1994 | Monticello | 435/282 |
| 5,358,870 | 10/1994 | Monticello et al. | 435/282 |
| 5,607,857 | 3/1997 | Grossman et al. | 435/282 |

FOREIGN PATENT DOCUMENTS 0 218 734  4/1987  European Pat. Off. .

OTHER PUBLICATIONS

Rudinger (1976) Characteristics of the amino acids as components of a peptide hormone sequence. In: Peptide Hormones. Ed. J. A. Parsons. University Park Press, Baltimore, MD. pp. 1–7, Jun. 1976.

Ngo et al. (1994) Computational complexity, protein structure prediction, and the lLevinthal paradox. In: The Protein Folding Problem and Tertiary Structure Prediction. Eds. Merz et al. Birkhauser et al. Boston, MA. pp. 491–495, Jan. 1994.

Thornton et al. (1995) Protein Engineering: Editorial Overview. Current Opinion in Biotechnology 6(4): 367–369, Aug. 1995.

Wallace (1993) Understanding cytochrome c function: engineering protein structure by semisynthesis. The FASEB Journal 7: 505–515, Apr. 1993.

Sigma Catalog 1995, Sigma Chemical Company, St. Louis, Missouri. pp. 320, 322, 323 and 327, Jan. 1995.

Constanti, M., et al., "Desulphurization of dibenzothiophene by bacteria," *World Journal of Microbiology & Biotechnology* 10(5) :510–516 (1994).

Klubek, B, et al., "Characterization of soil bacteria that desulphurize organic sulphur compounds. 1. Classification and growth studies," *Microbios* 88(357) :223–236 (1996).

Xu, Y. et al., Abstracts of the 95th General Meeting of the American Society for Microbiology, Q–281).

Li, M.Z. et al., "Genetic Analysis of the dsz Promoter and Associated Regulatory Regions of *Rhodococcus erythropolis* IGTS8," *J. Bacteriol.*, 178(22): 6409–6418 (Nov. 1996).

Parry, R.J. et al., "Cloning, Analysis, and Overexpression of the Gene Encoding Isobutylamine N–Hydroxylase from the Valanimycin Producer, *Streptomyces viridifaciens*," *J. Bacteriol.*, 179(2) : 409–416 (Jan. 1997).

Hirel, Ph. –Hervé, et al., "Extent of N–terminal methionine excision from *Escherichia coli* proteins is governed by the side–chain length of the penultimate amino acid," *Proc. Nat. Acad. Sci. USA*, 86: 8247–8251 (Nov. 1989).

Monticello, D.J. and Finnerty, W.R., "Microbial Desulfurization of Fossil Fuels," *Ann. Rev. Microbiol.*, 39: 371–389 (1985).

Gundlach, E.R. et al., The Fate of Amoco Cadiz Oil, *Science*, 221: 122–129 (1983).

Yen, K.–M., "Construction of Cloning Cartridges for Development of Expression Vectors in Gram–Negative Bacteria," *J. Bacteriol.*, 173: 5328–5335 (Sep. 1991).

Omori, T. et al., "Desulfurization of Dibenzothiophene by Corynebacterium sp. Strain SY1," *Appl. Env. Microbiol.*, 58(3) : 911–915 (Mar. 1992).

Izumi, Y. et al., "Selective Desulfurization of Dibenzothiophene by *Rhodococcus erythropolis* D–1," *Appl. Env. Microbiol.*, 60(1) : 223–226 (Jan. 1994).

Lee, M.K. et al., "Sulfur–Specific Microbial Desulfurization of Sterically Hindered Analogs of Dibenzothiophene," *Appl. Environ. Microbiol.*, 61(12) : 4362–4366 (Dec. 1995).

Constanti, M. et al., "Degradation and desulfurization of dibenzothiophene sulfone and other sulfur compounds by Agrobacterium MC501 and a mixed culture," *Enzyme Microb. Tech.*, 19: 214–219 (1996).

Gray, K.A. et al., "Molecular mechanisms of biocatalytic desulfurization of fossil fuels," *Nature Biotech.*, 14: 1705–1709 (Dec. 1996).

Altschul, S.F. et al., "Basic Local Alignment Search Tool," *J. Mol. Biol.*, 215: 403–410 (1990).

(List continued on next page.)

*Primary Examiner*—Bradley Sisson
*Assistant Examiner*—Einar Stole
*Attorney, Agent, or Firm*—Hamilton, Brook, Smith & Reynolds, P.C.

[57] ABSTRACT

The invention relates to a novel microorganism, designated Sphingomonas sp. strain AD109, which is capable of selectively desulfurizing dibenzothiophene. The invention also includes isolated proteins and nucleic acid sequences obtained from this microorganism. In another embodiment, the invention provides a method of using this microorganism or enzyme preparations derived therefrom in the biocatalytic desulfurization of a fossil fuel containing organic sulfur compounds.

46 Claims, 24 Drawing Sheets

OTHER PUBLICATIONS

West, S.E.H. et al., "Codon usage in *Pseudomonas aeruginosa*," *Nucl. Acids Res.*, 16(19) : 9323–9335 (1988).

Blanc, V. et al., "Cloning and Analysis of Structural Genes from *Streptomyces pristinaespiralis* Encoding Enzymes Involved in the Conversion of Pristinamycin $II_B$ to Pristinamycin $II_A$ ($PII_A$): $PII_A$ Synthase and NADH:Riboflavin 5'–Phosphate Oxidoreductase," *J. Bacteriol.*, 177(18) : 5206–5214 (Sep. 1995).

Duggleby, R.G., "[3] Analysis of Enzyme Progress Curves by Nonlinear Regression," *Methods Enzymo.*, 249: 61–90 (1995).

Denome, S.A. et al., "Characterization of the Desulfurization Genes from Rhodococcus sp. Strain IGTS8," *J. Bacteriol.*, 176(21) : 6707–6716 (Nov. 1994).

Woo, T.H.S. et al., "An Application of a Simple Method for the Preparation of Bacterial DNA," *BioTechniques*, 13 (5): 696–698 (1992).

Birboim, H.C. and Doly, J. "A rapid alkaline extraction procedure for screening recombinant plasmid DNA," *Nuc. Acids Res.*, 7(6) : 1513–1523 (1979).

Vogelstein and Gillespie, *Proc. Natl. Acad. Sci. USA*, 76: 615–619 (1979).

Devereux, J. et al., "A comprehensive set of sequence analysis programs for the VAX," *Nucl. Acids Res.*, 12(1) : 387–395 (1984).

Yabuuchi, E. et al., "Proposals of *Sphingomonas paucimobilis* gen. nov. and comb. nov., *Sphingomonas parapaucimobilis* sp. nov., *Sphingomonas yanoikuyae* sp. nov., *Sphingomonas adhaesiva* sp. nov., *Sphingomonas capsulata* comb. nov., and Two Genospecies of the Genus Sphingomonas," *Microbiol. Immunol.*, 34(2) : 99–119 (1990).

Foght, J.M. and Westlake, D.W.S., "Expression of dibenzothiophene–degradative genes in two Pseudomonas species," *Can. J. Microbiol.*, 36: 718–724 (1990).

Monticello, D.J. et al., "Plasmid–Mediated Degradation of Dibenzothiophene by Pseudomonas species," *Appl. Environ. Microbiol.*, 49(4) : 756–760 (Apr. 1985).

Piddington, C.S. et al., "Sequence and Molecular Characterization of a DNA Region Encoding the Dibenzothiophene Desulfurization Operon of Rhodococcus sp. Strain IGTS8," *App. Environ. Microbiol.*, 61(2) : 468–475 (Feb. 1995).

Brosius, J., "Laboratory Methods," *DNA*, 8(10) : 759–777 (1989).

Vieira, J. and Messing, J., "New pUC–derived Cloning vectors with different selectable markers and DNA replication origins," *Gene*, 100: 189–194 (1991).

Vieria, J. and Messing, J., "The pUC plasmids, an M13mp7–derived system for insertion mutagenesis and sequencing with synthetic universal primers," *Gene*, 19: 259–268 (1982).

Monticello, D.J. et al., "Practical Considerations in Biodesulfurization of Petroleum," IGT's 3rd Intl. Symp. on Gas, Oil, Coal and Env. Biotech., (Dec. 3–5, 1990) New Orleans, LA.

FIG. 1A

Sphingamonas ORF1

```
ATG ACC GAT CCA CGT CAG CTG CAC CTG GCC GGA TTC TTC TGT GCC GGC AAC GTC ACG CAC    60
Met Thr Asp Pro Arg Gln Leu His Leu Ala Gly Phe Phe Cys Ala Gly Asn Val Thr His
  1               5                  10                  15                  20

GCC CAC GGA GCG TGG CGC CAC GCC GAC TCC AAC GGC TTC CTC ACC AAG GAG TAC TAC       120
Ala His Gly Ala Trp Arg His Ala Asp Ser Asn Gly Phe Leu Thr Lys Glu Tyr Tyr
                 25                  30                  35                  40

CAG CAG ATT GCC CGC ACG CTC GAG CGC GGC AAG TTC GAC GGT GTT ATC GCC GCG ATG CTG   180
Gln Gln Ile Ala Arg Thr Leu Glu Arg Gly Lys Phe Asp Gly Val Ile Ala Ala Met Leu
                 45                  50                  55                  60

CTC GCC GTG TGG GAC AGC TAC GGC GAT AAT CTG GAG ACC GGT CTG CGG TAT GGC GGG CAA   240
Leu Ala Val Trp Asp Ser Tyr Gly Asp Asn Leu Glu Thr Gly Leu Arg Tyr Gly Gly Gln
                 65                  70                  75                  80

GGC GCG GTG ATG CTG GGC GTA GTT ATC GCC GCG ATG GCC TCG GTG ACC GAA CAT           300
Gly Ala Val Met Leu Gly Val Val Ile Ala Ala Met Ala Ser Val Thr Glu His
                 85                  90                  95                 100

CTG GGG CTG GGC GCC ACC ATT TCC ACC ACC TAC TAC CCG CCC TAC CAT GTA GCC CGG GTC   360
Leu Gly Leu Gly Ala Thr Ile Ser Thr Thr Tyr Tyr Pro Pro Tyr His Val Ala Arg Val
                105                 110                 115                 120

GTC GCT TCG CTG GAC CAG CTG TCC TCC GGG CGA GTG TCG TGG CGA GTG TCG CTG           420
Val Ala Ser Leu Asp Gln Leu Ser Ser Gly Arg Val Ser Trp Arg Val Ser Leu
                125                 130                 135                 140
```

*Sphingamonas* ORF1 (cont)

```
AGC AAT GCA GAG GCG CGC AAC TTC GGC CGC AAC TTC GAT GAA CAT CTC GAC CAC GAT GCC CGC TAC     480
Ser Asn Ala Glu Ala Arg Asn Phe Gly Asp Phe Asp Glu His Leu Asp His Asp Ala Arg Tyr
            145                 150                 155                 160

GAT CGC GCC GAT GAA TTC CTC GAG GTC GTG CGC AAG CTC GTG AAC AGC TGG GAT CGC GAT     540
Asp Arg Ala Asp Glu Phe Leu Glu Val Val Arg Lys Leu Val Asn Ser Trp Asp Arg Asp
            165                 170                 175                 180

GCC CTG ACA CTC GAC AAG GCA ACC GGC CAG TTC GCC GAT CCG GCT AAG GTG CGC TAC ATC     600
Ala Leu Thr Leu Asp Lys Ala Thr Gly Gln Phe Ala Asp Pro Ala Lys Val Arg Tyr Ile
            185                 190                 195                 200

GAC CAC CGC GGC GAA TGG CTC AAC GTA CGC GGG CCG CTT CAG GTG CCG CGC TCC CCC CAG     660
Asp His Arg Gly Glu Trp Leu Asn Val Arg Gly Pro Leu Gln Val Pro Arg Ser Pro Gln
            205                 210                 215                 220

GGC GAG CCT GTC ATT CTG CAG GCC GGG CTT TCG GCG CGG GGC AAG CGC TTC GCC GGG CGC     720
Gly Glu Pro Val Ile Leu Gln Ala Gly Leu Ser Ala Arg Gly Lys Arg Phe Ala Gly Arg
            225                 230                 235                 240

TGG GCG GAC GCG GTG TTC ACG ATT TCG CCC AAT CTG GAC ATC ATG CAG GCC ACG TAC CGC     780
Trp Ala Asp Ala Val Phe Thr Ile Ser Pro Asn Leu Asp Ile Met Gln Ala Thr Tyr Arg
            245                 250                 255                 260

GAC ATA AAG GCG CAG GTC GAG GCC GGA CGC GCC GAT CCC GAG CAG GTC AAG GTG TTT GCC     840
Asp Ile Lys Ala Gln Val Glu Ala Gly Arg Ala Asp Pro Glu Gln Val Lys Val Phe Ala
            265                 270                 275                 280
```

FIG. 1B

*Sphingamonas* ORF1 (cont)

```
GCG GTG ATG CCG ATC CTC GGC GAG ACC GAG GCG ATC GCC AGG CAG CGT CTC GAA TAC ATA   900
Ala Val Met Pro Ile Leu Gly Glu Thr Glu Ala Ile Ala Arg Gln Arg Leu Glu Tyr Ile
            285                 290                 295                 300

AAT TCG CTG GTG CAT CCC GAA GTC GGG CTT TCT ACG TTG TCC AGC CAT GTC GGG GTC AAC   960
Asn Ser Leu Val His Pro Glu Val Gly Leu Ser Thr Leu Ser Ser His Val Gly Val Asn
            305                 310                 315                 320

CTT GCC GAC TAT TCG CTC GAT ACC CCG CTG ACC GAG GTC CTG GGC GAT CTC GCC CAG CGC  1020
Leu Ala Asp Tyr Ser Leu Asp Thr Pro Leu Thr Glu Val Leu Gly Asp Leu Ala Gln Arg
            325                 330                 335                 340

AAC GTG CCC ACC CAA CTG GGC ATG TTC GCC AGG ATG TTG CAG GCC GAG ACG CTG ACC GTG  1080
Asn Val Pro Thr Gln Leu Gly Met Phe Ala Arg Met Leu Gln Ala Glu Thr Leu Thr Val
            345                 350                 355                 360

GGA GAA ATG GGC CGG CGT TAT GGC GCC AAC GTG GGC TTC GTC CCG CAG TGG GCG GGA ACC  1140
Gly Glu Met Gly Arg Arg Tyr Gly Ala Asn Val Gly Phe Val Pro Gln Trp Ala Gly Thr
            365                 370                 375                 380

CGC GAG CAG ATC GCG GAC CTG ATC GAG ATC CAT TTC AAG GCC GGC GCC GAT GGC TTC      1200
Arg Glu Gln Ile Ala Asp Leu Ile Glu Ile His Phe Lys Ala Gly Gly Ala Asp Gly Phe
            385                 390                 395                 400

ATC ATC TCG CCG GCG TTC CTG CCC GGA TCT TAC GAG GAA TTC GTC GAT CAG GTG GTG CCC  1260
Ile Ile Ser Pro Ala Phe Leu Pro Gly Ser Tyr Glu Glu Phe Val Asp Gln Val Val Pro
            405                 410                 415                 420
```

FIG. 1C

*Sphingamonas* ORF1 (cont)

ATC CTG CAG CAC CGC GGA CTG TTC CGC ACT GAT TAC GAA GGC CGC ACC CTG CGC AGC CAT
Ile Leu Gln His Arg Gly Leu Phe Arg Thr Asp Tyr Glu Gly Arg Thr Leu Arg Ser His
425                              430                         435                         440

CTG GGA CTG CGT GAA CCC GCA TAC CTG GGA GAG TAC GCA TGA         1320
Leu Gly Leu Arg Glu Pro Ala Tyr Leu Gly Glu Tyr Ala
445                              450

FIG. 1D

Sphingamonas ORF2

| | | | | | | | | | | | | | | | | | | | | |
|---|---|---|---|---|---|---|---|---|---|---|---|---|---|---|---|---|---|---|---|---|
ATG ACG ACA GAC ATC CAC CCG GCG AGC GCC GCA TCG TCG CCG GCG CGC GCG ACG ATC 60
Met Thr Thr Asp Ile His Pro Ala Ser Ala Ala Ser Ser Pro Ala Arg Ala Thr Ile
1                   5                  10                  15                  20

ACC TAC AGC AAC TGC CCC GTG CCT AAT GCC CTC CTC GCC GCG CTC GGC TCA GGT ATT CTG 120
Thr Tyr Ser Asn Cys Pro Val Pro Asn Ala Leu Leu Ala Ala Leu Gly Ser Gly Ile Leu
                        25                  30                  35                  40

GAC AGT GCC GGG ATC ACA CTT GCC CTG ACC GGA AAG CAG GGC GAG GTG CAC TTC ACC 180
Asp Ser Ala Gly Ile Thr Leu Ala Leu Thr Gly Lys Gln Gly Glu Val His Phe Thr
            45                  50                  55                  60

TAC GAC CGA GAT TAC ACC CGC TTC GGC GAG ATT CCG CTG GTC AGC GAG GGA 240
Tyr Asp Arg Asp Tyr Thr Arg Phe Gly Gly Glu Ile Pro Leu Val Ser Glu Gly
            65                  70                  75                  80

CTG CGT GCG CCG GGG CGG ACC CGC CTG GGA CTG ACG CCG GCC GTG CTG GGC 300
Leu Arg Ala Pro Gly Arg Thr Arg Leu Gly Leu Thr Pro Val Leu Gly Arg Trp Gly
            85                  90                  95                 100

TAC TTC GTC GGC GAC AGC GCG ATC CGC ACC CCG GCC GAT CTT GCC GGC CGC GTC 360
Tyr Phe Val Arg Gly Asp Ser Ala Ile Arg Thr Pro Ala Asp Leu Ala Gly Arg Val
           105                 110                 115                 120

GGA GTA TCC GAT TCG GCC AGG AGG ATA TTG ACC GGA AGG CTG GGC GAC TAC CGC GAA CTT 420
Gly Val Ser Asp Ser Ala Arg Arg Ile Leu Thr Gly Arg Leu Gly Asp Tyr Arg Glu Leu
           125                 130                 135                 140

FIG. 2A

Sphingamonas ORF2 (cont)

| | | | | | | | | | |
|---|---|---|---|---|---|---|---|---|---|
| GAT | CCC | TGG | CGG | CAG | ACC | CTG | GTC | GCG | CTG | GGG | ACA | TGG | GAG | GCG | CGT | GCC | TTG | CTG | AGC | 480 |
| Asp | Pro | Trp | Arg | Gln | Thr | Leu | Val | Ala | Leu | Gly | Thr | Trp | Glu | Ala | Arg | Ala | Leu | Leu | Ser |
| | | | 145 | | | | | 150 | | | | | 155 | | | | | 160 | |

ACG CTC GAG ACG GCG GGG CTT GGC GTC GGC GAC GTC GAG CTG ACG CGC ATC GAG AAC CCG 540
Thr Leu Glu Thr Ala Gly Leu Gly Val Gly Asp Val Glu Leu Thr Arg Ile Glu Asn Pro
             165                 170                 175                 180

TTC GTC GAC GTG CCG ACC GAA CGA CTG CAT GCC GCC GGC TCG CTC AAA GGA ACC GAC CTG 600
Phe Val Asp Val Pro Thr Glu Arg Leu His Ala Ala Gly Ser Leu Lys Gly Thr Asp Leu
             185                 190                 195                 200

TTC CCC GAC GTG ACC AGC CAG CAG GCC GCA GTC CTT GAG GAT GAG CGC GCC GAC GCC CTG 660
Phe Pro Asp Val Thr Ser Gln Gln Ala Ala Val Leu Glu Asp Glu Arg Ala Asp Ala Leu
             205                 210                 215                 220

TTC GCG TGG CTT CCC TGG GCG GCC GAG CTC GAG ACC CGC ATC GGT GCA CGG CCG GTC CTA 720
Phe Ala Trp Leu Pro Trp Ala Ala Glu Leu Glu Thr Arg Ile Gly Ala Arg Pro Val Leu
             225                 230                 235                 240

GAC CTC AGC GCA GAC GAC CGC AAT GCC TAT GCG AGC ACC TGG ACG GTG AGC GCC GAG CTG 780
Asp Leu Ser Ala Asp Asp Arg Asn Ala Tyr Ala Ser Thr Trp Thr Val Ser Ala Glu Leu
             245                 250                 255                 260

GTG GAC CGG CAG CCC GAA CTG GTG CAG CGG CTC GTC GAT GCC GTG GAT GCA GGG CGG 840
Val Asp Arg Gln Pro Glu Leu Val Gln Arg Leu Val Asp Ala Val Asp Ala Gly Arg
             265                 270                 275                 280

FIG. 2B

Sphingamonas ORF2

| TGG | GCC | GAG | GCC | AAT | GGC | GAT | GTC | GTC | TCC | CGC | CTG | CAC | GCC | GAT | AAC | CTC | GGT | GTC | AGT | |
|---|---|---|---|---|---|---|---|---|---|---|---|---|---|---|---|---|---|---|---|---|
| Trp | Ala | Glu | Ala | Asn | Gly | Asp | Val | Val | Ser | Arg | Leu | His | Ala | Asp | Asn | Leu | Gly | Val | Ser | 900 |
| | | | 280 | | | | | 285 | | | | | 290 | | | | | | 300 | |

| CCC | GAA | AGC | GTC | CGC | CAG | GGA | TTC | GGA | GCC | GAT | TTT | CAC | CGC | CGC | CTG | ACG | CCG | CGG | CTC | |
|---|---|---|---|---|---|---|---|---|---|---|---|---|---|---|---|---|---|---|---|---|
| Pro | Glu | Ser | Val | Arg | Gln | Gly | Phe | Gly | Ala | Asp | Phe | His | Arg | Arg | Leu | Thr | Pro | Arg | Leu | 960 |
| | | 305 | | | | | | 310 | | | | | 315 | | | | | | 320 | |

| GAC | AGC | GAT | GCT | ATC | GCC | ATC | CTG | GAG | CGT | ACT | CAG | CGG | TTC | CTG | AAG | GAT | GCG | AAC | CTG | |
|---|---|---|---|---|---|---|---|---|---|---|---|---|---|---|---|---|---|---|---|---|
| Asp | Ser | Asp | Ala | Ile | Ala | Ile | Leu | Glu | Arg | Thr | Gln | Arg | Phe | Leu | Lys | Asp | Ala | Asn | Leu | 1020 |
| | | | 325 | | | | | 330 | | | | | 335 | | | | | | 340 | |

| ATC | GAT | CGG | TCG | TTG | GCG | CTC | GAT | CGG | TGG | GCT | GCA | CCT | GAA | TTC | CTC | GAA | CAA | AGT | CTC | |
|---|---|---|---|---|---|---|---|---|---|---|---|---|---|---|---|---|---|---|---|---|
| Ile | Asp | Arg | Ser | Leu | Ala | Leu | Asp | Arg | Trp | Ala | Ala | Pro | Glu | Phe | Leu | Glu | Gln | Ser | Leu | 1080 |
| | | 345 | | | | | | 350 | | | | | 355 | | | | | | 360 | |

| TCA | CGC | CAG | GTC | GAA | GGG | CAG | ATA | GCA | TGA |
|---|---|---|---|---|---|---|---|---|---|
| Ser | Arg | Gln | Val | Glu | Gly | Gln | Ile | Ala | |
| | | 365 | | | | | | 370 | |

FIG. 2C

*Sphingomonas* ORF3

```
ATG AAC GAA CTC GTC AAA GAT CTC GGC CTC AAT CGA TCC GAT CCG ATC GGC GCT GTG CGG      60
Met Asn Glu Leu Val Lys Asp Leu Gly Leu Asn Arg Ser Asp Pro Ile Gly Ala Val Arg
 1               5                  10                  15                  20

CGA CTG GCC GCG CAG TGG GGG GCC ACC GCT GTT GAT CGG GAC CGG GCC GGA TCG GCA     120
Arg Leu Ala Ala Gln Trp Gly Ala Thr Ala Val Asp Arg Asp Arg Ala Gly Gly Ser Ala
             25                  30                  35                  40

ACC GCC GAA CTC GAT CAA CTG CGC GGC AGC GGC CTG CTC TCG CTG TCC ATT CCC GCC GCA     180
Thr Ala Glu Leu Asp Gln Leu Arg Gly Ser Gly Leu Leu Ser Leu Ser Ile Pro Ala Ala
             45                  50                  55                  60

TAT GGC GGC TGG GGC GAC TGG CCA ACG ACT CTG GAA GTT ATC CGC GAA GTC GCA ACG     240
Tyr Gly Gly Trp Gly Asp Trp Pro Thr Thr Leu Glu Val Ile Arg Glu Val Ala Thr
             65                  70                  75                  80

GTG GAC GGA TCG CTG GCG CAT CTA TTC GGC TAC CAC CTC GGC TGC GTA CCG ATG ATC GAG     300
Val Asp Gly Ser Leu Ala His Leu Phe Gly Tyr His Leu Gly Cys Val Pro Met Ile Glu
             85                  90                  95                 100

CTG TTC GGC TCG GCG CCA CAA AAG GAA CGG CTG TAC CGC CAG ATC GCA AGC CAT GAT TGG     360
Leu Phe Gly Ser Ala Pro Gln Lys Glu Arg Leu Tyr Arg Gln Ile Ala Ser His Asp Trp
            105                 110                 115                 120

CGG GTC GGG AAT GCG TCG AGC GAA AAC AGC CAC GTC CTC GAG TGG AAG CTT GCC GCC     420
Arg Val Gly Asn Ala Ser Ser Glu Asn Ser His Val Leu Glu Trp Lys Leu Ala Ala
            125                 130                 135                 140
```

FIG. 3A sPHINGOMONAS orf3 (cont)

```
ACC GCC GTC GAT GAT GGC GGG TTC GTC CTC AAC GGC GCG AAG CAC TTC TGC AGC GGC GCC    480
Thr Ala Val Asp Asp Gly Gly Phe Val Leu Asn Gly Ala Lys His Phe Cys Ser Gly Ala
        145                 150                 155                 160

AAA AGC TCC GAC CTG CTC GTG TTC GGC GTG ATC CAG GAC GAA TCC CCC CTG CGC GGC    540
Lys Ser Ser Asp Leu Leu Val Phe Gly Val Ile Gln Asp Glu Ser Pro Leu Arg Gly
        165                 170                 175                 180

GCG ATC ATC ACC GCG GTC ATT CCC ACC GAC CGG GCC GGT GTT CAG ATC AAT GAC GAC TGG    600
Ala Ile Ile Thr Ala Val Ile Pro Thr Asp Arg Ala Gly Val Gln Ile Asn Asp Asp Trp
        185                 190                 195                 200

CGC GCA ATC GGG ATG CGC CAG ACC GAC AGC GGC AGC GCC GAA TTT CGC GAC GTC CGA GTC    660
Arg Ala Ile Gly Met Arg Gln Thr Asp Ser Gly Ser Ala Glu Phe Arg Asp Val Arg Val
        205                 210                 215                 220

TAC CCA GAC GAG ATC TTG GGG GCA CCA AAC TCA GTC GTT GAG GCG TTC GTG ACA AGC AAC    720
Tyr Pro Asp Glu Ile Leu Gly Ala Pro Asn Ser Val Val Glu Ala Phe Val Thr Ser Asn
        225                 230                 235                 240

CGC GGC AGC CTG TGG ACG CCG GCG ATT CAG TCG ATC TTC TCG AAC GTT TAT CTG GGG CTC    780
Arg Gly Ser Leu Trp Thr Pro Ala Ile Gln Ser Ile Phe Ser Asn Val Tyr Leu Gly Leu
        245                 250                 255                 260

GCG CGT GGC GCG GCA GCG CTC GAG CTG GCA GCG GCA GCG GAT TAC ACC CAG AGC CGC CCC TGG ACA    840
Ala Arg Gly Ala Ala Leu Glu Leu Ala Ala Ala Asp Tyr Thr Gln Ser Arg Pro Trp Thr
        265                 270                 275                 280
```

FIG. 3B

```
Sphingomonas ORF3 (cont)

CCC GCC GGC GTG GCG AAG GCG ACA GAG GAT CCC CAC ATC ATC GCC ACC TAC GGT GAA CTG   900
Pro Ala Gly Val Ala Lys Ala Thr Glu Asp Pro His Ile Ile Ala Thr Tyr Gly Glu Leu
                285                 290                 295                 300

GCG ATC GCG CTC CAG GGC GCC GAG GCG CGC GAG GTC GCG GCG CTG TTG CAA CAG           960
Ala Ile Ala Leu Gln Gly Ala Glu Ala Arg Glu Val Ala Ala Leu Leu Gln Gln
                305                 310                 315                 320

GCG TGG GAC AAG GGC GAT GCG GTG ACG CCC GAA GAG CGC GGC CAG CTG ATG GTG AAG GTT  1020
Ala Trp Asp Lys Gly Asp Ala Val Thr Pro Glu Glu Arg Gly Gln Leu Met Val Lys Val
                325                 330                 335                 340

TCG GGT GTG AAG GCC CTC TCG ACG AAG GCC GCA CTC GAC ATC ACC AGC CGT ATT TTC GAG  1080
Ser Gly Val Lys Ala Leu Ser Thr Lys Ala Ala Leu Asp Ile Thr Ser Arg Ile Phe Glu
                345                 350                 355                 360

ACA ACG GGC TCG CGA TCG ACG CAT CCC AGA TAC GGA TTC GAT TTC TGG CGT AAC ATC      1140
Thr Thr Gly Ser Arg Ser Thr His Pro Arg Tyr Gly Phe Asp Phe Trp Arg Asn Ile
                365                 370                 375                 380

CGG ACT CAT ACG CTG CAC GAT CCG GTA TAT AAA ATC GTC GAT GTG GGG AAC TAC ACG      1200
Arg Thr His Thr Leu His Asp Pro Val Tyr Lys Ile Val Asp Val Gly Asn Tyr Thr
                385                 390                 395                 400

CTC AAC GGG ACA TTC CCG GTT CCC GGA TTT ACG TCA
Leu Asn Gly Thr Phe Pro Val Pro Gly Phe Thr Ser
                405                 410

FIG. 3C
```

*Sphingomonas dsz sequence*

```
GGTTCGAGAT CGATCTGACC GTCGAACCCG GCGCGGTTCA AACCATCCTC TGGGGCCTCT    60
CCAAGCTCTA GCTAGACTGG CAGCTTGGGC CGCGCCAAGT TTGGTAGGAG ACCCCGGAGA

TCTTGCACTT GACATAGGAA TCTCTACTAA ATAAATAGAT ATTTATTCGA CACTAAGTTC   120
AGAACGTGAA CTGTATCCTT AGAGATGATT TATTTATCTA TAAATAAGCT GTGATTCAAG

GGTGATCAGG CCGACCGTGT GTCTCAAGTG CTCGCTCCGG GTTGCCACGA GCTAAAGCGC   180
CCACTAGTCC GGCTGGCACA CAGAGTTCAC GAGCGAGGCC CAACGGTGCT CGATTTCGCG

GCGATGCTGG GGCGACAGCG CTAGGCATTG CGTTCCCTCA CACCAATGAT GAGATGATAC   240
CGCTACGACC CCGCTGTCGC GATCCGTAAC GCAAGGGAGT GTGGTTACTA CTCTACTATG

GATGCGCATG ACCACTATCC GCACCTAGCA CGAAAGATCC GTGCATTTCG CGAATGCCAA   300
CTACGCGTAC TGGTGATAGG CGTGGATCGT GCTTTCTAGG CACGTAAAGC GCTTACGGTT

TGAAGAGGAC CGACGTACGG CAGCTTCCTA CGCTTTCGCG CCATCGTTCA TAGCCAAGGT   360
ACTTCTCCTG GCTGCATGCC GTCGAAGGAT GCGAAAGCGC GGTAGCAAGT ATCGGTTCCA

CTTTTCGACG CCGGTTCGCG TGGGCGACTG ACGGCGGTAG CGCCGCGACT ATTCGTTTCA   420
GAAAAGCTGC GGCCAAGCGC ACCCGCTGAC TGCCGCCATC GCGGCGCTGA TAAGCAAAGT

AACTCACGAG GATAAGAGCC TATGACCGAT CCACGTCAGC TGCACCTGGC CGGATTCTTC   480
TTGAGTGCTC CTATTCTCGG ATACTGGCTA GGTGCAGTCG ACGTGGACCG GCCTAAGAAG

TGTGCCGGCA ACGTCACGCA CGCCCACGGA GCGTGGCGCC ACGCCGACGA CTCCAACGGC   540
ACACGGCCGT TGCAGTGCGT GCGGGTGCCT CGCACCGCGG TGCGGCTGCT GAGGTTGCCG

TTCCTCACCA AGGAGTACTA CCAGCAGATT GCCCGCACGC TCGAGCGCGG CAAGTTCGAC   600
AAGGAGTGGT TCCTCATGAT GGTCGTCTAA CGGGCGTGCG AGCTCGCGCC GTTCAAGCTG
```

FIG. 6A

*Sphingomonas dsz* sequence (cont)

```
CTGCTGTTCC TTCCCGACGC GCTCGCCGTG TGGGACAGCT ACGGCGACAA TCTGGAGACC    660
GACGACAAGG AAGGGCTGCG CGAGCGGCAC ACCCTGTCGA TGCCGCTGTT AGACCTCTGG

GGTCTGCGGT ATGGCGGGCA AGGCGCGGTG ATGCTGGAGC CCGGCGTAGT TATCGCCGCG    720
CCAGACGCCA TACCGCCCGT TCCGCGCCAC TACGACCTCG GCCGCATCA ATAGCGGCGC

ATGGCCTCGG TGACCGAACA TCTGGGGCTG GCGCCACCA TTTCCACCAC CTACTACCCG    780
TACCGGAGCC ACTGGCTTGT AGACCCCGAC CCGCGGTGGT AAAGGTGGTG GATGATGGGC

CCCTACCATG TAGCCCGGGT CGTCGCTTCG CTGGACCAGC TGTCCTCCGG GCGAGTGTCG    840
GGGATGGTAC ATCGGGCCCA GCAGCGAAGC GACCTGGTCG ACAGGAGGCC CGCTCACAGC

TGGAACGTGG TCACCTCGCT CAGCAATGCA GAGGCGCGCA ACTTCGGCTT CGATGAACAT    900
ACCTTGCACC AGTGGAGCGA GTCGTTACGT CTCCGCGCGT TGAAGCCGAA GCTACTTGTA

CTCGACCACG ATGCCCGCTA CGATCGCGCC GATGAATTCC TCGAGGTCGT GCGCAAGCTC    960
GAGCTGGTGC TACGGGCGAT GCTAGCGCGG CTACTTAAGG AGCTCCAGCA CGCGTTCGAG

TGGAACAGCT GGGATCGCGA TGCGCTGACA CTCGACAAGG CAACCGGCCA GTTCGCCGAT   1020
ACCTTGTCGA CCCTAGCGCT ACGCGACTGT GAGCTGTTCC GTTGGCCGGT CAAGCGGCTA

CCGGCTAAGG TGCGCTACAT CGACCACCGC GGCGAATGGC TCAACGTACG CGGGCCGCTT   1080
GGCCGATTCC ACGCGATGTA GCTGGTGGCG CCGCTTACCG AGTTGCATGC GCCCGGCGAA

CAGGTGCCGC GCTCCCCCCA GGGCGAGCCT GTCATTCTGC AGGCCGGGCT TTCGGCGCGG   1140
GTCCACGGCG CGAGGGGGGT CCCGCTCGGA CAGTAAGACG TCCGGCCCGA AAGCCGCGCC

GGCAAGCGCT TCGCCGGGCG CTGGGCGGAC GCGGTGTTCA CGATTTCGCC CAATCTGGAC   1200
CCGTTCGCGA AGCGGCCCGC GACCCGCCTG CGCCACAAGT GCTAAAGCGG GTTAGACCTG
```

FIG. 6B

*Sphingomonas dsz* sequence (cont)

```
ATCATGCAGG CCACGTACCG CGACATAAAG GCGCAGGTCG AGGCCGCCGG ACGCGATCCC   1260
TAGTACGTCC GGTGCATGGC GCTGTATTTC CGCGTCCAGC TCCGGCGGCC TGCGCTAGGG

GAGCAGGTCA AGGTGTTTGC CGCGGTGATG CCGATCCTCG GCGAGACCGA GGCGATCGCC   1320
CTCGTCCAGT TCCACAAACG GCGCCACTAC GGCTAGGAGC CGCTCTGGCT CCGCTAGCGG

AGGCAGCGTC TCGAATACAT AAATTCGCTG GTGCATCCCG AAGTCGGGCT TTCTACGTTG   1380
TCCGTCGCAG AGCTTATGTA TTTAAGCGAC CACGTAGGGC TTCAGCCCGA AAGATGCAAC

TCCAGCCATG TCGGGTCAA CCTTGCCGAC TATTCGCTCG ATACCCCGCT GACCGAGGTC   1440
AGGTCGGTAC AGCCCCAGTT GGAACGGCTG ATAAGCGAGC TATGGGGCGA CTGGCTCCAG

CTGGGCGATC TCGCCCAGCG CAACGTGCCC ACCCAACTGG GCATGTTCGC CAGGATGTTG   1500
GACCCGCTAG AGCGGGTCGC GTTGCACGGG TGGGTTGACC CGTACAAGCG GTCCTACAAC

CAGGCCGAGA CGCTGACCGT GGGAGAAATG GGCCGGCGTT ATGGCGCCAA CGTGGGCTTC   1560
GTCCGGCTCT GCGACTGGCA CCCTCTTTAC CCGGCCGCAA TACCGCGGTT GCACCCGAAG

GTCCCGCAGT GGGCGGGAAC CCGCGAGCAG ATCGCGGACC TGATCGAGAT CCATTTCAAG   1620
CAGGGCGTCA CCCGCCCTTG GGCGCTCGTC TAGCGCCTGG ACTAGCTCTA GGTAAAGTTC

GCCGGCGGCG CCGATGGCTT CATCATCTCG CCGGCGTTCC TGCCCGGATC TTACGAGGAA   1680
CGGCCGCCGC GGCTACCGAA GTAGTAGAGC GGCCGCAAGG ACGGGCCTAG AATGCTCCTT

TTCGTCGATC AGGTGGTGCC CATCCTGCAG CACCGCGGAC TGTTCCGCAC TGATTACGAA   1740
AAGCAGCTAG TCCACCACGG GTAGGACGTC GTGGCGCCTG ACAAGGCGTG ACTAATGCTT

GGCCGCACCC TGCGCAGCCA TCTGGGACTG CGTGAACCCG CATACCTGGG AGAGTACGCA   1800
CCGGCGTGGG ACGCGTCGGT AGACCCTGAC GCACTTGGGC GTATGGACCC TCTCATGCGT
```

FIG. 6C

*Sphingomonas dsz* sequence (cont)

```
TGACGACAGA CATCCACCCG GCGAGCGCCG CATCGTCGCC GGCGGCGCGC GCGACGATCA   1860
ACTGCTGTCT GTAGGTGGGC CGCTCGCGGC GTAGCAGCGG CCGCCGCGCG CGCTGCTAGT

CCTACAGCAA CTGCCCCGTG CCTAATGCCC TGCTCGCCGC GCTCGGCTCA GGTATTCTGG   1920
GGATGTCGTT GACGGGGCAC GGATTACGGG ACGAGCGGCG CGAGCCGAGT CCATAAGACC

ACAGTGCCGG GATCACACTT GCCCTGCTGA CCGGAAAGCA GGGCGAGGTG CACTTCACCT   1980
TGTCACGGCC CTAGTGTGAA CGGGACGACT GGCCTTTCGT CCCGCTCCAC GTGAAGTGGA

ACGACCGAGA TGACTACACC CGCTTCGGCG GCGAGATTCC GCCGCTGGTC AGCGAGGGAC   2040
TGCTGGCTCT ACTGATGTGG GCGAAGCCGC CGCTCTAAGG CGGCGACCAG TCGCTCCCTG

TGCGTGCGCC GGGGCGGACC CGCCTGCTGG GACTGACGCC GGTGCTGGGC CGCTGGGGCT   2100
ACGCACGCGG CCCCGCCTGG GCGGACGACC CTGACTGCGG CCACGACCCG GCGACCCCGA

ACTTCGTCCG GGGCGACAGC GCGATCCGCA CCCCGGCCGA TCTTGCCGGC CGCCGCGTCG   2160
TGAAGCAGGC CCCGCTGTCG CGCTAGGCGT GGGGCCGGCT AGAACGGCCG GCGGCGCAGC

GAGTATCCGA TTCGGCCAGG AGGATATTGA CCGGAAGGCT GGGCGACTAC CGCGAACTTG   2220
CTCATAGGCT AAGCCGGTCC TCCTATAACT GGCCTTCCGA CCCGCTGATG GCGCTTGAAC

ATCCCTGGCG GCAGACCCTG GTCGCGCTGG GGACATGGGA GGCGCGTGCC TTGCTGAGCA   2280
TAGGGACCGC CGTCTGGGAC CAGCGCGACC CCTGTACCCT CCGCGCACGG AACGACTCGT

CGCTCGAGAC GGCGGGGCTT GGCGTCGGCG ACGTCGAGCT GACGCGCATC GAGAACCCGT   2340
GCGAGCTCTG CCGCCCCGAA CCGCAGCCGC TGCAGCTCGA CTGCGCGTAG CTCTTGGGCA

TCGTCGACGT GCCGACCGAA CGACTGCATG CCGCCGGCTC GCTCAAAGGA ACCGACCTGT   2400
AGCAGCTGCA CGGCTGGCTT GCTGACGTAC GGCGGCCGAG CGAGTTTCCT TGGCTGGACA
```

FIG. 6D

*Sphingomonas dsz sequence* (cont)

```
TCCCCGACGT GACCAGCCAG CAGGCCGCAG TCCTTGAGGA TGAGCGCGCC GACGCCCTGT  2460
AGGGGCTGCA CTGGTCGGTC GTCCGGCGTC AGGAACTCCT ACTCGCGCGG CTGCGGGACA

TCGCGTGGCT TCCCTGGGCG GCCGAGCTCG AGACCCGCAT CGGTGCACGG CCGGTCCTAG  2520
AGCGCACCGA AGGGACCCGC CGGCTCGAGC TCTGGGCGTA GCCACGTGCC GGCCAGGATC

ACCTCAGCGC AGACGACCGC AATGCCTATG CGAGCACCTG GACGGTGAGC GCCGAGCTGG  2580
TGGAGTCGCG TCTGCTGGCG TTACGGATAC GCTCGTGGAC CTGCCACTCG CGGCTCGACC

TGGACCGGCA GCCCGAACTG GTGCAGCGGC TCGTCGATGC CGTGGTGGAT GCAGGGCGGT  2640
ACCTGGCCGT CGGGCTTGAC CACGTCGCCG AGCAGCTACG GCACCACCTA CGTCCCGCCA

GGGCCGAGGC CAATGGCGAT GTCGTCTCCC GCCTGCACGC CGATAACCTC GGTGTCAGTC  2700
CCCGGCTCCG GTTACCGCTA CAGCAGAGGG CGGACGTGCG GCTATTGGAG CCACAGTCAG

CCGAAAGCGT CCGCCAGGGA TTCGGAGCCG ATTTTCACCG CCGCCTGACG CCGCGGCTCG  2760
GGCTTTCGCA GGCGGTCCCT AAGCCTCGGC TAAAAGTGGC GGCGGACTGC GGCGCCGAGC

ACAGCGATGC TATCGCCATC CTGGAGCGTA CTCAGCGGTT CCTGAAGGAT GCGAACCTGA  2820
TGTCGCTACG ATAGCGGTAG GACCTCGCAT GAGTCGCCAA GGACTTCCTA CGCTTGGACT

TCGATCGGTC GTTGGCGCTC GATCGGTGGG CTGCACCTGA ATTCCTCGAA CAAAGTCTCT  2880
AGCTAGCCAG CAACCGCGAG CTAGCCACCC GACGTGGACT TAAGGAGCTT GTTTCAGAGA

CACGCCAGGT CGAAGGGCAG ATAGCATGAA CGAACTCGTC AAAGATCTCG GCCTCAATCG  2940
GTGCGGTCCA GCTTCCCGTC TATCGTACTT GCTTGAGCAG TTTCTAGAGC CGGAGTTAGC

ATCCGATCCG ATCGGCGCTG TGCGGCGACT GGCCGCGCAG TGGGGGGCCA CCGCTGTTGA  3000
TAGGCTAGGC TAGCCGCGAC ACGCCGCTGA CCGGCGCGTC ACCCCCCGGT GGCGACAACT
```

FIG. 6E

*Sphingomonas dsz* sequence (cont)

```
TCGGGACCGG GCCGGCGGAT CGGCAACCGC CGAACTCGAT CAACTGCGCG GCAGCGGCCT    3060
AGCCCTGGCC CGGCCGCCTA GCCGTTGGCG GCTTGAGCTA GTTGACGCGC CGTCGCCGGA

GCTCTCGCTG TCCATTCCCG CCGCATATGG CGGCTGGGGC GCCGACTGGC CAACGACTCT    3120
CGAGAGCGAC AGGTAAGGGC GGCGTATACC GCCGACCCCG CGGCTGACCG GTTGCTGAGA

GGAAGTTATC CGCGAAGTCG CAACGGTGGA CGGATCGCTG GCGCATCTAT TCGGCTACCA    3180
CCTTCAATAG GCGCTTCAGC GTTGCCACCT GCCTAGCGAC CGCGTAGATA AGCCGATGGT

CCTCGGCTGC GTACCGATGA TCGAGCTGTT CGGCTCGGCG CCACAAAAGG AACGGCTGTA    3240
GGAGCCGACG CATGGCTACT AGCTCGACAA GCCGAGCCGC GGTGTTTTCC TTGCCGACAT

CCGCCAGATC GCAAGCCATG ATTGGCGGGT CGGGAATGCG TCGAGCGAAA ACAACAGCCA    3300
GGCGGTCTAG CGTTCGGTAC TAACCGCCCA GCCCTTACGC AGCTCGCTTT TGTTGTCGGT

CGTGCTCGAG TGGAAGCTTG CCGCCACCGC CGTCGATGAT GGCGGGTTCG TCCTCAACGG    3360
GCACGAGCTC ACCTTCGAAC GGCGGTGGCG GCAGCTACTA CCGCCCAAGC AGGAGTTGCC

CGCGAAGCAC TTCTGCAGCG GCGCCAAAAG CTCCGACCTG CTCATCGTGT TCGGCGTGAT    3420
GCGCTTCGTG AAGACGTCGC CGCGGTTTTC GAGGCTGGAC GAGTAGCACA AGCCGCACTA

CCAGGACGAA TCCCCCCTGC GCGGCGCGAT CATCACCGCG GTCATTCCCA CCGACCGGGC    3480
GGTCCTGCTT AGGGGGGACG CGCCGCGCTA GTAGTGGCGC CAGTAAGGGT GGCTGGCCCG

CGGTGTTCAG ATCAATGACG ACTGGCGCGC AATCGGGATG CGCCAGACCG ACAGCGGCAG    3540
GCCACAAGTC TAGTTACTGC TGACCGCGCG TTAGCCCTAC GCGGTCTGGC TGTCGCCGTC

CGCCGAATTT CGCGACGTCC GAGTCTACCC AGACGAGATC TTGGGGGCAC CAAACTCAGT    3600
GCGGCTTAAA GCGCTGCAGG CTCAGATGGG TCTGCTCTAG AACCCCGTG  GTTTGAGTCA
```

FIG. 6F

*Sphingomonas dsz sequence* (cont)

```
CGTTGAGGCG TTCGTGACAA GCAACCGCGG CAGCCTGTGG ACGCCGGCGA TTCAGTCGAT   3660
GCAACTCCGC AAGCACTGTT CGTTGGCGCC GTCGGACACC TGCGGCCGCT AAGTCAGCTA

CTTCTCGAAC GTTTATCTGG GGCTCGCGCG TGGCGCGCTC GAGGCGGCAG CGGATTACAC   3720
GAAGAGCTTG CAAATAGACC CCGAGCGCGC ACCGCGCGAG CTCCGCCGTC GCCTAATGTG

CCGGACCCAG AGCCGCCCCT GGACACCCGC CGGCGTGGCG AAGGCGACAG AGGATCCCCA   3780
GGCCTGGGTC TCGGCGGGGA CCTGTGGGCG GCCGCACCGC TTCCGCTGTC TCCTAGGGGT

CATCATCGCC ACCTACGGTG AACTGGCGAT CGCGCTCCAG GGCGCCGAGG CGGCCGCGCG   3840
GTAGTAGCGG TGGATGCCAC TTGACCGCTA GCGCGAGGTC CCGCGGCTCC GCCGGCGCGC

CGAGGTCGCG GCCCTGTTGC AACAGGCGTG GGACAAGGGC GATGCGGTGA CGCCCGAAGA   3900
GCTCCAGCGC CGGGACAACG TTGTCCGCAC CCTGTTCCCG CTACGCCACT GCGGGCTTCT

GCGCGGCCAG CTGATGGTGA AGGTTTCGGG TGTGAAGGCC CTCTCGACGA AGGCCGCCCT   3960
CGCGCCGGTC GACTACCACT TCCAAAGCCC ACACTTCCGG GAGAGCTGCT TCCGGCGGGA

CGACATCACC AGCCGTATTT TCGAGACAAC GGGCTCGCGA TCGACGCATC CCAGATACGG   4020
GCTGTAGTGG TCGGCATAAA AGCTCTGTTG CCCGAGCGCT AGCTGCGTAG GGTCTATGCC

ATTCGATCGG TTCTGGCGTA ACATCCGGAC TCATACGCTG CACGATCCGG TATCGTATAA   4080
TAAGCTAGCC AAGACCGCAT TGTAGGCCTG AGTATGCGAC GTGCTAGGCC ATAGCATATT

AATCGTCGAT GTGGGGAACT ACACGCTCAA CGGGACATTC CCGGTTCCCG GATTTACGTC   4140
TTAGCAGCTA CACCCCTTGA TGTGCGAGTT GCCCTGTAAG GGCCAAGGGC CTAAATGCAG

ATGA                                                                 4144
TACT
```

FIG. 6G

```
DszA (S)    1   MTDPRQLHLAGFFCAGNVTHAHGAWRHADDSNGFLTKEYYQQIARTLERG   50
                ||:.||:|||||||:|||||||||||||.|.||:||..|||:||||||||
DszA (R)    1   MTQQRQMHLAGFFSAGNVTHAHGAWRHTDASNDFLSGKYYQHIARTLERG   50

DszA (S)   51   KFDLLFLPDALAVWDSYGDNLETGLRYGGQGAVMLEPGVVIAAMASVTEH  100
                ||||||||:|||  ||||||:||: .||||| |||: |:|.||.||||
DszA (R)   51   KFDLLFLPDGLAVEDSYGDNLDTGVGLGGQGAVALEPASVVATMAAVTEH  100

DszA (S)  101   LGLGATISTTYYPPYHVARVVASLDQLSSGRVSWNVVTSLSNAEARNFGF  150
                ||||||||.|||||||||||.|.||||:||||||||||||..:|||||:
DszA (R)  101   LGLGATISATYYPPYHVARVFATLDQLSGGRVSWNVVTSLNDAEARNFGI  150

DszA (S)  151   DEHLDHDARYDRADEFLEVVRKLWNSWDRDALTLDKATGQFADPAKVRYI  200
                ::||:||||||||||||.|:|||||||.|||.||||.| |||||||:|:
DszA (R)  151   NQHLEHDARYDRADEFLEAVKKLWNSWDEDALVLDKAAGVFADPAKVHYV  200

DszA (S)  201   DHRGEWLNVRGPLQVPRSPQGEPVILQAGLSARGKRFAGRWADAVFTISP  250
                ||:|||||||||||||||||||||||||||:||:||||:|:||:.:.|
DszA (R)  201   DHHGEWLNVRGPLQVPRSPQGEPVILQAGLSPRGRRFAGKWAEAVFSLAP  250

DszA (S)  251   NLDIMQATYRDIKAQVEAAGRDPEQVKVFAAVMPILGETEAIARQRLEYI  300
                ||:||||.:|||:|:||||||||:|:|.|:|||:|||.:|:..:|||:
DszA (R)  251   NLEVMQATYQGIKAEVDAAGRDPDQTKIFTAVMPVLGESQAVAQERLEYL  300

DszA (S)  301   NSLVHPEVGLSTLSSHVGVNLADYSLDTPLTEVLGDLAQRNVPTQLGMFA  350
                |||||||||||||||.|:|||.|.||||:..:| ||.:||||||| |||
DszA (R)  301   NSLVHPEVGLSTLSSHTGINLAAYPLDTPIKDILRDLQDRNVPTQLHMFA  350

DszA (S)  351   RMLQAETLTVGEMGRRYGANVGFVPQWAGTREQIADLIEIHFKAGGADGF  400
                :.|.||::|||||||||.||||||||||||||||||  :  ||.:|||
DszA (R)  351   AATHSEELTLAEMGRRYGTNVGFVPQWAGTREQIADLIEIHFKAGGADGF  400

DszA (S)  401   IISPAFLPGSYEEFVDQVVPILQHRGLFRTDYEGRTLRSHLGLREPAYLG  450
                |||||||||||:||||||:||.||.|||:|:|.|||.|||||  |
DszA (R)  401   IISPAFLPGSYDEFVDQVVPVLQDRGYFRTEYQGNTLRDHLGLRVPQLQG  450

DszA (S)  451   EYA  453
                :  .
DszA (R)  451   QPS  453
```

FIG. 8

```
DszB (S)  MTTDIHPASAASSPAA--RATITYSNCPVPNALLAALGSGILDSAGITLALL       50
          ||    ||    |    | | |||||||||||| | || || ||| | |
DszB      MTSRVDPANPGSELDSAIRDTLTYSNCPVPNALLTASESGFLDAAGIELDVL       52

DszB (S)  TGKQGEVHFTYDRDDYTRFGGEIPPLVSEGLRAPGRTRLLGLTPVLGRWGYF      102
          | ||  ||||||   |||||||||| ||||||||||||||| || ||| ||
DszB      SGQQGTVHFTYDQPAYTRFGGEIPPLLSEGLRAPGRTRLLGITPLLGRQGFF      104

DszB (S)  VRGDSAIRTPADLAGRRVGVSDSARRILTGRLGDYRELDPWRQTLVALGTWE      154
          || ||  |   |||||| || | |  || |||||| |||||||||||| ||
DszB      VRDDSPITAAADLAGRRIGVSASAIRILRGQLGDYLELDPWRQTLVALGSWE      156

DszB (S)  ARALLSTLETAGLGVGDVELTRIENPFVDVPTERLHAAGSLKGTDLFPDVTS      206
          ||||| |||   ||| |||| |   | ||||  |       || ||||||
DszB      ARALLHTLEHGELGVDDVELVPISSPGVDVPAEQLEESATVKGADLFPDVAR      208

DszB (S)  QQAAVLEDERADALFAWLPWAAELETRIGARPVLDLSADDRNAYASTWTVSA      258
          |||||    |||   ||||| ||||  | ||||||||  |  |||||| ||
DszB      GQAAVLASGDVDALYSWLPWAGELQA-TGARPVVDLGLDERNAYASVWTVSS      260

DszB (S)  ELVDRQPELVQRLVDAVVDAGRWAEANGDVVSRLHADNLGVSPESVRQGFGA      310
          ||   | |||||||||||| |   |  |||||| |||||| |  ||||||
DszB      GLVRQRPGLVQRLVDAAVDAGLWARDHSDAVTSLHAANLGVSTGAVGQGFGA      312 szB  (S)  DFHRRLTPRLDSDAIAILERTQRFLKDANLIDRSLALDRWAAPEFLEQSLSRQVEGQIA  369
          || ||| |||| || || ||||| || | ||    ||  ||||||||||||| || |
DszB      DFQQRLVPRLDHDALALLERTQQFLLTNNLLQEPVALDQWAAPEFLNNSLNRHR        365
```

FIG. 9

```
DszC (S)   1    .....MNELVKDLGLNRSDPIGAVRRLAAQWGATAVDRDRAGGSATAELD    45
                     .: |:.  : . .||:::..|  ||..|  ||||:||||||||||| :
DszC (R)   1    MTLSPEKQHVRPRDAADNDPVAVARGLAEKWRATAVERDRAGGSATAERE    50

DszC (S)  46    QLRGSGLLSLSIPAAYGGWADWPTTLEVIREVATVDGSLAHLFGYHLGC     95
                :|||:|:||||  :|  .|||||||||||||..:||:||:|..||||:|||||||.
DszC (R)  51    DLRASALLSLLVPREYGGWADWPTAIEVVREIAAADGSLGHLFGYHLTN    100

DszC (S)  96    VPMIELFGSAPQKERLYRQIASHDWRVGNASSENNSHVLEWKLAATAVDD    145
                .|||||:||..|.|:||  |||  ::|:.|||||||||||||||:||:.||:.:|
DszC (R0 101    APMIELIGSQEQEEHLYTQIAQNNWWTGNASSENNSHVLDWKVSATPTED    150

DszC (S) 146    GGFVLNGAKHFCSGAKSSDLLIVFGVIQDESPLRGAIITAVIPTDRAGVQ    195
                ||:||||.|||||||||:|||||:||||:||:||  .||||.|.|||.||||
DszC (R) 151    GGYVLNGTKHFCSGAKGSDLLFVFGVVQDDSPQQGAIIAAAIPTSRAGVT    200

DszC (S) 196    INDDWRAIGMRQTDSGSAEFRDVRVYPDEILGAPNSVVEAFVTSNRGSLW    245
                ||||  ||||||||||||..:|::|:|  |||:|||||..|  |||:  |:|||||:
DszC (R0 201    PNDDWAAIGMRQTDSGSTDFHNVKVEPDEVLGAPNAFVLAFIQSERGSLF    250

DszC (S) 246    TPAIQSIFSNVYLGLARGALEAAADYTRTQSRPWTPAGVAKATEDPHIIA    295
                .|   |  ||.||||:|:|||:||  :|||||.|||||||:...||||..|
DszC (R) 251    APIAQLIFANVYLGIAHGALDAAREYTRTQARPWTPAGIQQATEDPYTIR    300

DszC (S) 296    TYGELAIALQGAEAAAREVAALLQQAWDKGDAVTPEERGQLMVKVSGVKA    345
                .|||:.||||||:|||||.|  |||  .||||||:|||:||:||||||||||
DszC (R) 301    SYGEFTIALQGADAAAREAAHLLQTVWDKGDALTPEDRGELMVKVSGVKA    350

DszC (S) 346    LSTKAALDITSRIFETTGSRSTHPRYGFDRFWRNIRTHTLHDPVSYKIVD    395
                |.|.|||:|.|  :||..|.|:|||||||||||:|||.|||||||||.|
DszC (R) 351    LATNAALNISSGVFEVIGARGTHPRYGFDRFWRNVRTHSLHDPVSYKIAD    400

DszC (S) 396    VGNYTLNGTFPVPGFTS    412
                ||..||||  :|:|||||
DszC (R) 401    VGKHTLNGQYPIPGFTS    417

FIG. 10
```

SPHINGOMONAS BIODESULFURIZATION CATALYST

RELATED APPLICATIONS

This application is a Continuation-in-part of Ser. No. 08/835,292, filed Apr. 7, 1997, now abandoned, the contents of which are incorporated herein by reference in their entirety.

BACKGROUND OF THE INVENTION

The microbial desulfurization of fossil fuels has been an area of active investigation for over fifty years. The object of these investigations has been to develop biotechnology based methods for the pre-combustion removal of sulfur from fossil fuels, such as coal, crude oil and petroleum distillates. The driving forces for the development of desulfurization methods are the increasing levels of sulfur in fossil fuel and the increasingly stringent regulation of sulfur emissions. Monticello et al., "Practical Considerations in Biodesulfurization of Petroleum," IGT's 3d Intl. Symp. on Gas, Oil, Coal and Env. Biotech., (Dec. 3–5, 1990) New Orleans, La.

Many biocatalysts and processes have been developed to desulfurize fossil fuels, including those described in U.S. Pat. Nos. 5,356,801, 5,358,870, 5,356,813, 5,198,341, 5,132,219, 5,344,778, 5,104,801 and 5,002,888, incorporated herein by reference. Economic analyses indicate that one limitation in the commercialization of the technology is improving the reaction rates and specific activities of the biocatalysts, such as the bacteria and enzymes that are involved in the desulfurization reactions. The reaction rates and specific activities (sulfur removed/hour/gram of biocatalyst) that have been reported in the literature are much lower than those necessary for optimal commercial technology. Therefore, improvements in the longevity and specific activity of the biocatalyst are desirable.

SUMMARY OF THE INVENTION

The invention relates to a novel microorganism, designated Sphingomonas sp. strain AD109, as well as isolated proteins and nucleic acid sequences obtained from this microorganism. This microorganism was obtained using a soil enrichment process using 2-(2-hydroxyphenyl) benzenesulfinate as the sole sulfur source. A biologically pure sample of this microorganism has been isolated and characterized.

The invention also relates to a collection of desulfurization enzymes isolated from Sphingomonas sp. strain AD109 which, together, catalyze the oxidative desulfurization of dibenzothiophene (DBT).

In another embodiment, the invention includes an isolated nucleic acid molecule, such as a DNA or RNA nucleotide sequence or molecule, which encodes one or more of the Sphingomonas desulfurization enzymes, or a homologue or active fragment thereof. The invention also includes a recombinant microorganism containing one or more heterologous nucleic acid molecules which encode one or more of the Sphingomonas desulfurization enzymes or homologues or active fragments thereof.

In a further embodiment, the invention provides a method of using the Sphingomonas microorganism or an enzyme preparation derived therefrom as a biocatalyst in the biocatalytic desulfurization of a fossil fuel containing organosulfur compounds. The method comprises the steps of (1) contacting the fossil fuel with an aqueous phase containing a Sphingomonas biocatalyst which is capable of biocatalytic desulfurization and, optionally, a flavoprotein, thereby forming a fossil fuel and aqueous phase mixture; (2) maintaining the mixture under conditions sufficient for sulfur oxidation and/or cleavage of the carbon-sulfur bonds of the organosulfur molecules by the biocatalyst, and (3) separating the fossil fuel having a reduced organic sulfur content from the resulting aqueous phase.

The invention also provides a method of oxidizing an organic compound. The method comprises the steps of: (1) contacting the organic compound with an aqueous phase containing a Sphingomonas biocatalyst comprising at least one enzyme capable of catalyzing at least one step in the oxidative cleavage of carbon-sulfur bonds, thereby forming an organic compound and aqueous phase mixture; (2) maintaining the mixture of step (1) under conditions sufficient for oxidation of the organic compound by the biocatalyst, thereby resulting in an oxidized organic compound, and, optionally, separating the oxidized organic compound from the aqueous phase.

BRIEF DESCRIPTION OF THE DRAWINGS

FIGS. 1A, 1B, 1C and 1D together set forth the DNA sequence and the corresponding amino acid sequence of open reading frame 1 (ORF-1, dszA) of the nucleotide sequence required for desulfurization activity in Sphingomonas sp. strain AD109.

FIGS. 2A, 2B and 2C together set forth the DNA sequence and the corresponding amino acid sequence of open reading frame 2 (ORF-2, dszb) of the nucleotide sequence required for desulfurization activity in Sphingomonas sp. strain AD109.

FIGS. 3A, 3B and 3C together set forth the DNA sequence and the corresponding amino acid sequence of open reading frame 3 (ORF-3, dszC) of the nucleotide sequence required for desulfurization activity in Sphingomonas sp. strain AD109.

FIGS. 6A, 6B, 6C, 6D, 6E, 6F and 6G together set forth the nucleotide sequence of the Sphingomonas dsz gene cluster.

FIG. 8 presents the results of a GAP analysis of the DszA proteins from Sphingomonas sp. strain AD109 and Rhodococcus IGTS8.

FIG. 9 presents the results of a GAP analysis of the DszB proteins from Sphingomonas sp. strain AD109 and Rhodococcus IGTS8.

FIG. 10 presents the results of a GAP analysis of the sequences of the DszC proteins from Sphingomonas sp. strain AD109 and Rhodococcus IGTS8.

DETAILED DESCRIPTION OF THE INVENTION

Figure 4:
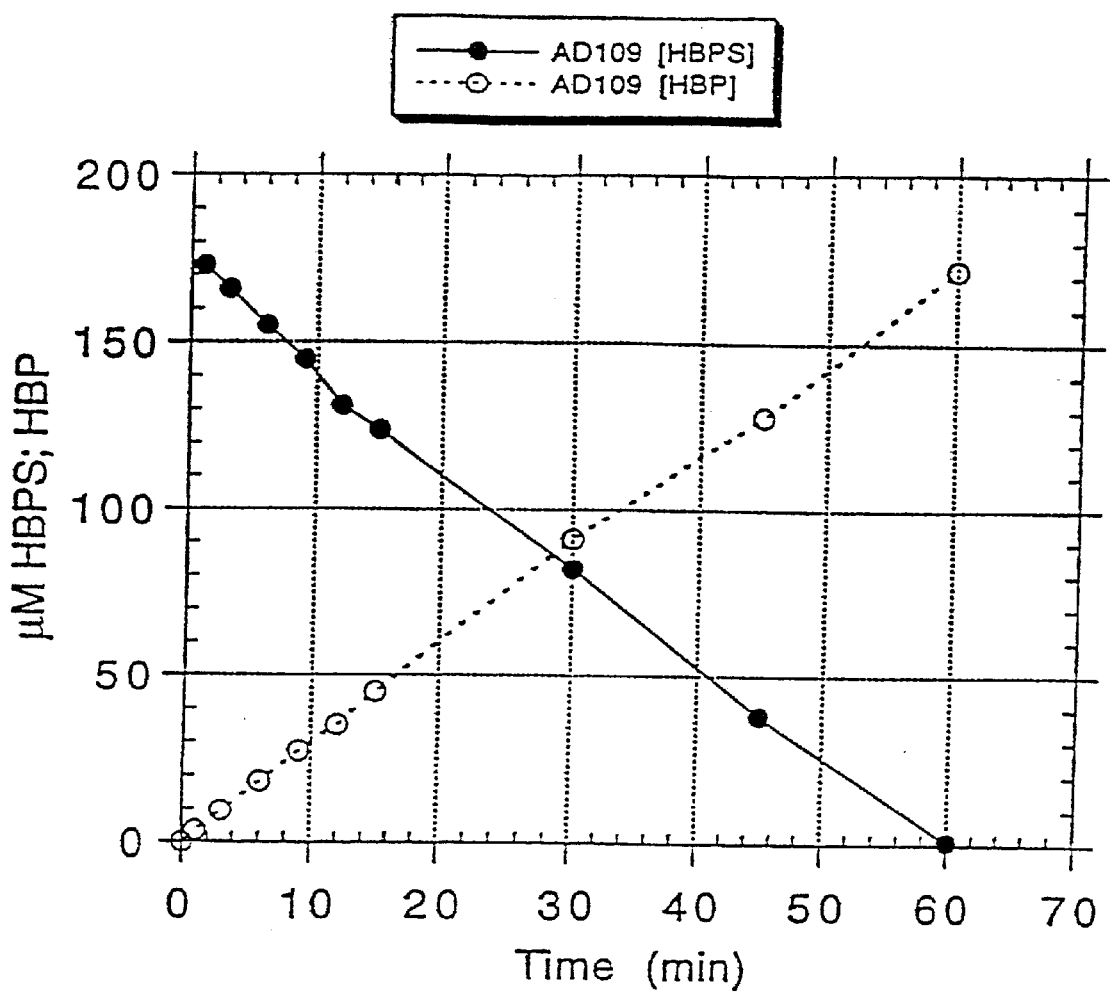
FIG. 4 is a graph showing the disappearance of 2-(2-phenyl)benzenesulfinate (HPBS) and the appearance of 2-hydroxybiphenyl (2-HBP) in the presence of Sphingomonas AD109 cell-free lysates.
Figure 5:
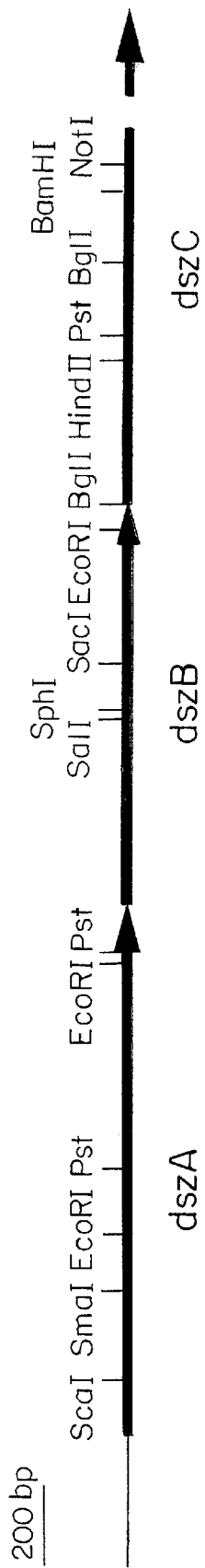
FIG. 5 shows a physical map of the Sphingomonas dsz gene cluster.

The present invention is based on the discovery and isolation of a novel microorganism which is capable of selectively desulfurizing dibenzothiophene ("DBT"). As described in Example 1, this microorganism was obtained from soil samples obtained at sites contaminated with petroleum and petroleum by-products by a soil enrichment procedure using 2-(2-hydroxyphenyl)benzenesulfinate as the sole sulfur source. A biologically pure sample of the novel microorganism has been isolated and characterized. The microorganism is a motile, gram-negative rod. Based on a fatty acid analysis, as described in Example 2, this microorganism has been identified as a Sphingomonas species, and designated strain AD-109. This microorganism has been deposited at the American Type Culture Collection (ATCC), 12301 Park Lawn Drive, Rockville, Md., U.S.A. 20852 under the terms of the Budapest Treaty and has been designated as ATCC Deposit No. 55954 on Apr. 21, 1997.

The novel microorganism of the invention can be grown by fermentation under aerobic conditions in the presence of a sulfur-free mineral salts medium (e.g., 4 g/L $K_2HPO_4$, 4 g/L $Na_2HPO_4$, 2 g/L $NH_4Cl$, 0.2 g/L $MgCl_2.6H_2O$, 0.001 g/L $CaCl_2.2H_2O$, and 0.001 g/L $FeCl_3.6H_2O$), containing a sulfur-free source of assimilable carbon such as glucose. The sole source of sulfur provided can be a heterocyclic organosulfur compound, such as dibenzothiophene or a derivative thereof.

Sphingomonas sp. strain AD109 expresses a collection of enzymes which together catalyze the conversion of DBT to 2-hydroxybiphenyl (also referred to as "2-HBP") and inorganic sulfur. An enzyme which catalyzes one or more steps in this overall process is referred to herein as a "desulfurization enzyme". The nucleic acid sequence required for this overall process has been identified and cloned using the general method described in U.S. Pat. No. 5,356,801, the contents of which are incorporated herein by reference, and is set forth in FIG. 6 (SEQ ID NO.: 12). This nucleic acid sequence (also referred to as the "Sphingomonas dsz sequence") comprises three open reading frames, designated ORF-1 (base pairs 442–1800, also set forth in FIGS. 1A–1D and SEQ ID NO.: 1), ORF-2 (base pairs 1800–2909, also set forth in FIGS. 2A–2C and SEQ ID NO.: 3) and ORF-3 (base pairs 2906–4141, sequence also set forth in FIGS. 3A–3C and SEQ ID NO.: 5). The predicted amino acid sequences encoded by these open reading frames are set forth in FIGS. 1A–1D (ORF-1, SEQ ID NO: 2), FIGS. 2A–2C (ORF-2, SEQ ID NO.: 4) and FIGS. 3A–3C (ORF-3, SEQ ID NO.: 6). Each of these open reading frames is homologous to the corresponding open reading frame of Rhodococcus sp. IGTS8; the sequences of the Rhodococcus open reading frames are disclosed in U.S. Pat. No. 5,356,801.

In one embodiment, the present invention provides an isolated nucleic acid molecule comprising one or more nucleotide sequences which encode one or more of the biodesulfurization enzymes of Sphingomonas sp. strain AD109. The isolated nucleic acid molecule can be, for example, a nucleotide sequence, such as a deoxyribonucleic acid (DNA) sequence or a ribonucleic acid (RNA) sequence. Such a nucleic acid molecule comprises one or more nucleotide sequences which encode one or more of the amino acid sequences set forth in SEQ ID NO.: 2, SEQ ID NO.: 4, and SEQ ID NO.: 6. For example, the isolated nucleic acid molecule can comprise one or more of the nucleotide sequences of SEQ ID NO.: 1, SEQ ID NO.: 3, and SEQ ID NO.: 5, or a complement of any of these sequences. The isolated nucleic acid molecule can also comprise a nucleotide sequence which results from a silent mutation of one or more of the sequences set forth in SEQ ID NO.: 1, SEQ ID NO.: 3, and SEQ ID NO.: 5. Such a nucleotide sequence can result, for example, from a mutation of the native sequence in which one or more codons have been replaced with a degenerate codon, i.e., a codon which encodes the same amino acid. Such mutant nucleotide sequences can be constructed using methods which are well known in the art, for example the methods discussed by Ausubel et al., *Current Protocols in Molecular Biology*, Wiley-Interscience, New York (1997)(hereinafter "Ausubel et al.") and by Sambrook et al., *Molecular Cloning: A Laboratory Manual*, third edition, Cold Spring Harbor Laboratory Press (1992) (hereinafter "Sambrook et al."), each of which are incorporated herein by reference.

In another embodiment, the invention includes an isolated nucleic acid molecule comprising a nucleotide sequence which is homologous to one or more of the sequences of SEQ ID NO.: 1, SEQ ID NO.: 3, and SEQ ID NO.: 5, or complements thereof. Such a nucleotide sequence exhibits at least about 80% homology, or sequence identity, with one of these Sphingomonas nucleotide sequences, preferably at least about 90% homology or sequence identity. Particularly preferred sequences have at least about 95% homology or have essentially the same sequence. Preparation of mutant nucleotide sequences can be accomplished by methods known in the art as are described in Old, et al., *Principles of Gene Manipulation*, Fourth Edition, Blackwell Scientific Publications (1989), in Sambrook et al., and in Ausubel et al.

The invention further includes nucleic acid molecules which are useful as hybridization probes, for example, for the isolation of the Sphingomonas genes encoding desulfurization enzymes or identical or homologous genes from other organisms. Such molecules comprise nucleotide sequences which hybridize to all or a portion of the nucleotide sequence of SEQ ID NO.: 1, SEQ ID NO.: 3 or SEQ ID NO.: 5 or to non-coding regions immediately (within about 1000 nucleotides) 5' or 3' of each open reading frame. The invention also includes an isolated nucleic acid molecule which comprises a fragment of one or more of the nucleotide sequences set forth in SEQ ID NO.: 1, SEQ ID NO.: 3 or SEQ ID NO.: 5 or complements of any of these sequences. Such a fragment will generally comprise at least about 20 or at least about 40 contiguous nucleotides and, preferably, at least about 50 contiguous nucleotides of one of the disclosed sequences. Preferably, the hybridization probe of the invention hybridizes to one of these sequences under stringent conditions, such as those set forth by Sambrook et al. and Ausubel et al. For example, under conditions of high stringency, such as high temperatures and low salt concentrations, only DNA molecules which are essentially exact matches, or complements, will hybridize, particularly if the probe is relatively short. Hybridization under conditions of lower stringency, such as low temperatures, low formamide concentrations and high salt concentrations, allows greater mismatch between the probe and the target DNA molecule. It is particularly preferred that the nucleic acid molecule hybridizes selectively to the disclosed sequences().

The nucleic acid molecules can be synthesized chemically from the disclosed sequences. Alternatively, the nucleic acid molecules can be isolated from a suitable nucleic acid library (such as a DNA library) obtained from a microorganism which is believed to possess the nucleic acid molecule (such as, Sphingomonas sp. strain AD109), employing hybridizing primers and/or probes designed from the disclosed sequences. Such a method can result in isolating the disclosed molecules (or spontaneous mutants thereof) for use in preparing recombinant enzymes, confirming the disclosed sequences, or for use in mutagenizing the native sequences.

In yet another embodiment, the nucleic acid molecule of the present invention can be a nucleic acid molecule, such as a recombinant DNA molecule, resulting from the insertion into its chain by chemical or biological means, of one or more of the nucleotide sequences described above. Recombinant DNA includes any DNA synthesized by procedures using restriction nucleases, nucleic acid hybridization, DNA cloning, DNA synthesis or any combination of the preceding. Methods of construction can be found in Sambrook et al. and Ausubel et al., and additional methods are known by those skilled in the art.

The isolated nucleic acid molecule of the invention can further comprise a nucleotide sequence which encodes an oxidoreductase, such as a flavoprotein, such as a flavin reductase. For example, the nucleic acid molecule can encode an oxidoreductase which is native to Sphingomonas sp. strain AD109. The nucleic acid molecule can also encode the oxidoreductase denoted DszD described in copending U.S. patent application Ser. No. 08/583,118; the flavin reductase from *Vibrio harveyii* described in copending U.S. patent application Ser. No. 08/351,754; or the flavin reductase from Rhodococcus sp. IGTS8, described in copending U.S. patent application Ser. No. 08/735,963. The contents of each of these applications are incorporated herein by reference.

The invention also includes a plasmid or vector comprising a recombinant DNA sequence or molecule which comprises one or more of the nucleic acid molecules, e.g. nucleotide sequences, of the invention, as described above. The terms "plasmid" and "vector" are intended to encompass any replication competent or replication incompetent plasmid or vector capable of having foreign or exogenous DNA inserted into it by chemical or biological means and subsequently, when transformed into an appropriate non-human host organism, of expressing the product of the foreign or exogenous DNA insert (e.g., of expressing the biocatalyst and flavoprotein of the present invention). In addition, the plasmid or vector is receptive to the insertion of a DNA molecule or fragment thereof containing the gene or genes of the present invention, said gene or genes encoding a biocatalyst as described herein. Procedures for the construction of DNA plasmid vectors include those described in Sambrook et al. and Ausubel et al. and others known by those skilled in the art.

The plasmids of the present invention include any DNA fragment containing a nucleotide sequence as described above. The DNA fragment should be transmittable, for example, to a host microorganism by transformation or conjugation. Procedures for the construction or extraction of DNA plasmids include those described in Sambrook et al. and Ausubel et al., and others known by those skilled in the art. In one embodiment, the plasmid comprises a nucleotide sequence of the invention operatively linked to a competent or functional regulatory sequence. Examples of suitable regulatory sequences include promoters, enhancers, transcription binding sites, ribosomal binding sites, transcription termination sequences, etc.

In one preferred embodiment, the regulatory or promoter sequences are those native to the Sphingomonas operon containing the genes disclosed herein. In yet another embodiment, one or more regulatory sequences (e.g. the promoter) is native to the selected host cell for expression. The promoter can be selected so that the gene or genes are inducible or constitutively expressed. Furthermore, the sequences can be regulated individually or together, as an operon. Examples of suitable promoters include the *E. coli* lac and tac promoters and the Pseudomonas $P_G$ promoter (Yen, *J. Bacteriol.* 173 : 5328–5335 (1991)). An example of such a plasmid and its construction are described in Example 8.

In another embodiment, the invention relates to a recombinant or transformed non-human host organism which contains a heterologous DNA molecule of the invention as described above. The recombinant non-human host organisms of the present invention can be created by various methods by those skilled in the art. Any method for introducing a recombinant plasmid, such as a plasmid of the invention described above, into the organism of choice can be used, and a variety of such methods are described by Sambrook et al. and Ausubel et al. For example, the recombinant plasmid can be introduced via a suitable vector by transformation, conjugation, transduction or electroporation. By the term "non-human host organism" is intended any non-human organism capable of the uptake and expression of foreign, exogenous or recombinant DNA.

The recombinant microorganism can be derived from a host organism which does not express a native desulfurization biocatalyst. Such microorganisms include bacteria and yeasts, e.g., *E. coli*, Bacillus, and non-desulfurizing pseudomonads (as described in U.S. patent application Ser. No. 08/851,085. In another embodiment, the recombinant microorganism is derived from a host organism which expresses a native biodesulfurization catalyst. Preferred microorganisms of this type are Rhodococcus sp. IGTS8 (ATCC 53968), recombinant microorganisms comprising one or more of the IGTS8 desulfurizing genes and Sphingomonas sp. strain AD109. Other desulfurizing microorganisms which are suitable host organisms include Corynebacterium sp. strain SY1, as disclosed by Omori et al., *Appl. Env. Microbiol.*, 58 : 911–915 (1992); *Rhodococcus erythropolis* D-1, as disclosed by Izumi et al., *Appl. Env. Microbiol.*, 60 :223–226 (1994); the Arthrobacter strain described by Lee et al., Appl. Environ. Microbiol. 61 : 4362–4366' (1995); the Agrobacterium strain disclosed by Constanti et al., *Enzyme Microb. Tech.* 19 : 214–219 (1996) and the Rhodococcus strains (ATCC 55309 and ATCC 55310) disclosed by Grossman et al., U.S. Pat. No. 5,607, 857, each of which is incorporated herein by reference in its entirety. Each of these microorganisms produces one or more enzymes (protein biocatalysts) that catalyze one or more reactions in the desulfurization of DBT.

The invention also relates to desulfurization enzymes which can be isolated from Sphingomonas sp. strain AD109. These include desulfurization enzymes which catalyze one or more steps in the oxidative desulfurization of DBT. The enzyme encoded by ORF-2 has been partially purified and exhibits 2-(2-hydroxyphenyl)benzenesulfinate (HPBS) desulfinase activity and has an apparent molecular weight by denaturing gel electrophoresis of about 40,000 daltons.

In one embodiment, the invention includes an isolated desulfurization enzyme from Sphingomonas sp. strain AD109 using methods and assays which are known the art, for example, the methods used by Gray et al. to isolate and characterize desulfurization enzymes from Rhodococcus IGTS8 (Gray et al., *Nature Biotech.* 14 : 1705–1709 (1996)). These enzymes can be isolated or purified from the cell by lysing the cell and subjecting the cell lysate to known protein purification methods, and testing the fractions obtained thereby for the desired enzymatic activity. Examples of suitable protein purification methods include ammonium sulfate precipitation, ultrafiltration, diafiltration, immunoabsorption, anion exchange chromatography, gel filtration chromatography and hydrophobic interaction chromatography. The enzymes of the invention can also be recombinant proteins produced by heterologous expression of a nucleic acid molecule comprising a nucleotide sequence of SEQ ID NO.: 1, SEQ ID NO.: 3 or SEQ ID NO.: 5; or a mutation or fragment thereof, as discussed above. When the recombinant organism is derived from a non-Sphingomonas host, the recombinant proteins can be prepared in a form which is substantially free of other Sphingomonas proteins.

The invention also includes an isolated enzyme having an amino acid sequence which is homologous to the amino acid sequence of SEQ ID NO.: 2, SEQ ID NO.: 4 or SEQ ID NO.: 6, or fragments thereof. The term "homologous" or "homologue", as used herein, describes a protein (which is not obtained from Rhodococcus or Rhodococcus sp IGTS8) having at least about 80% sequence identity or homology with the reference protein, and preferably about 90% sequence homology, in an amino acid alignment. Most preferably, the protein exhibits at least about 95% homology or essentially the same sequence as the disclosed sequence. An amino acid alignment of two or more proteins can be produced by methods known in the art, for example, using a suitable computer program, such as BLAST (Altschul et al., *J. Mol. Biol.* 215 : 403–410 (1990)). A homologous protein can also have one or more additional amino acids appended at the carboxyl terminus or amino terminus, such as a fusion protein.

The homologous enzymes described herein can be native to an organism, such as a desulfurizing microorganism, including Sphingomonas sp. strain AD109 and mutants thereof. Such enzymes can be isolated from such sources using standard techniques and assays, as are described in the Exemplification and others known in the art. For example, the Sphingomonas desulfurization enzymes can be used to induce the formation of antibodies, such as monoclonal antibodies, according to known methods. The antibodies can then be used to purify the desulfurization enzymes from a desulfurizing organism via affinity chromatography, as is well known in the art.

The homologous enzymes of the invention can also be non-naturally occurring. For example, a homologous enzyme can be a mutant desulfurization enzyme which has a modified amino acid sequence resulting from the deletion, insertion or substitution of one or more amino acid residues in the amino acid sequence of a Sphingomonas desulfurization enzyme. Such amino acid sequence variants can be prepared by methods known in the art. For example, the desired polypeptide can be synthesized in vitro using known methods of peptide synthesis. The amino acid sequence variants are preferably made by introducing appropriate nucleotide changes into a DNA molecule encoding the native enzyme, followed by expression of the mutant enzyme in an appropriate vector, such as *E. coli*. These methods include site-directed mutagenesis or random mutagenesis, for example.

Particularly preferred mutants include those having amino acid sequences which include the amino acid residues which are encoded by both SEQ ID NO.: 1, SEQ ID NO.: 3 or SEQ ID NO.: 5 and the corresponding open reading frame of Rhodococcus sp. IGTS8, as disclosed in U.S. Pat. No. 5,356,801. That is, these mutants include the amino acid residues which are conserved in these two organisms in an amino acid alignment. Mutants which result from conservative substitution of one or more of these conserved residues, as well as non-conserved residues, are also included. Conservative and non-conservative substitutions (including deletions and insertions) can be made in non-conserved regions of the amino acid sequence and mutants resulting from both conservative and non-conservative substitutions of these residues are included herein.

Conservative substitutions are those in which a first amino acid residue is substituted by a second residue having similar side chain properties. An example of such a conservative substitution is replacement of one hydrophobic residue, such as valine, with another hydrophobic residue, such as leucine. A non-conservative substitution involves replacing a first residue with a second residue having different side chain properties. An example of this type of substitution is the replacement of a hydrophobic residue, such as valine, with an acidic residue, such as glutamic acid.

The two primary variables in the construction of amino acid sequence variants are (1) the location of the mutation site and (2) the nature of the mutation. These variables can be manipulated to identify amino acid residues at the active site of the enzyme. For example, an amino acid substitution which yields a mutant enzyme having significantly different activity than the native enzyme suggests that the substituted amino acid residue is at the active site. Such mutants can have the same or similar, increased or decreased activity relative to that of the native enzyme.

Amino acids can be modified, for example, by substituting first with a conservative choice, followed by non-conservative choices depending upon the results achieved, by deleting the target residue(s) or by inserting residues adjacent to a particular site. Variants can also be constructed using a combination of these approaches.

The proteins of the present invention can be produced using techniques to overexpress the gene, as are described by Sambrook et al. and Ausubel et al. Improved expression, activity or overexpression of the Sphingomonas desulfurization enzymes (in Sphingomonas sp AD 109 or in recombinant host cells harboring the disclosed nucleic acid molecules) can also be accomplished by mutagenesis. Suitable mutagens include radiation, e.g., ultraviolet radiation, and chemical mutagens, such as N-methyl-N'-nitrosoguanidine, hydroxylamine, ethylmethanesulfonate and nitrous acid. Furthermore, spontaneous mutants can be selected where the microorganism is subjected to an enrichment culture, as exemplified herein. The mutagenesis and subsequent screening for mutants harboring increased enzymatic activity can be conducted according to methods generally known in the art.

The present invention also provides a method of desulfurizing a carbonaceous material containing organosulfur molecules. The carbonaceous material can be, for example, a DBT-containing material or a fossil fuel, such as petroleum, a petroleum distillate fraction or coal. The method comprises the steps of (1) contacting the carbonaceous material with an aqueous phase containing a Sphingomonas-derived biocatalyst comprising at least one enzyme capable of catalyzing at least one step in the oxidative cleavage of carbon-sulfur bonds, thereby forming a carbonaceous material and aqueous phase mixture; (2) maintaining the mixture of step (1) under conditions sufficient for biocatalysis; and (3) separating the carbonaceous material having a reduced organic sulfur content from the resulting aqueous phase.

The term "Sphingomonas-derived biocatalyst", as used herein, is a biocatalyst which includes one or more desulfurization enzymes encoded by SEQ ID NO.: 1, SEQ ID NO.: 3 and SEQ ID NO.: 5; or a mutant or homologue thereof. In one embodiment, the biocatalyst is a microorganism, such as Sphingomonas sp. strain AD109. The biocatalyst can also be a recombinant organism which contains one or more heterologous nucleotide sequences or nucleic acid molecules as described above.

Although living microorganisms (e.g., a culture) can be used as the biocatalyst herein, this is not required. Biocatalytic enzyme preparations that are useful in the present invention include microbial lysates, extracts, fractions, subfractions, or purified products obtained by conventional means and capable of carrying out the desired biocatalytic function. Generally, such enzyme preparations are substantially free of intact microbial cells. In a particularly preferred embodiment, the biocatalyst is overexpressed in the recombinant host cell (such as a cell which contains more than one copy of the gene or genes).

Enzyme biocatalyst preparations suitable for use herein can optionally be affixed to a solid support, e.g., a membrane, filter, polymeric resin, glass particles or beads, or ceramic particles or beads. The use of immobilized enzyme preparations facilitates the separation of the biocatalyst from the treated fossil fuel which has been depleted of refractory organosulfur compounds.

A fossil fuel that is suitable for desulfurization treatment according to the present invention is one that contains organic sulfur. Such a fossil fuel is referred to as a "substrate fossil fuel". Substrate fossil fuels that are rich in thiophenic sulfur are particularly suitable for desulfurization according to the method described herein. Examples of such substrate fossil fuels include Cerro Negro or Orinoco heavy crude oils; Athabascan tar and other types of bitumen; petroleum refining fractions such as gasoline, kerosene, diesel, fuel oil, residual oils and miscellaneous refinery by-products; shale oil and shale oil fractions; and coal-derived liquids manufactured from sources such as Pocahontas #3, Lewis-Stock, Australian Glencoe or Wyodak coal.

In the petroleum extraction and refining arts, the term "organic sulfur" is generally understood as referring to organic molecules having a hydrocarbon framework to which one or more sulfur atoms are covalently joined. These sulfur atoms can be directly bonded to the hydrocarbon framework, e.g., by one or more carbon-sulfur bonds, or can be present in a substituent bonded to the hydrocarbon framework of the molecule, e.g., a sulfate group. The general class of organic molecules having one or more sulfur heteroatoms are sometimes referred to as "organosulfur compounds". The hydrocarbon portion of these compounds can be aliphatic and/or aromatic.

Sulfur-bearing heterocycles, such as substituted and unsubstituted thiophene, benzothiophene, and dibenzothiophene, are known to be stable to conventional desulfurization treatments, such as hydrodesulfurization (HDS). Sulfur-bearing heterocycles can have relatively simple or relatively complex chemical structures. In complex heterocycles, multiple condensed aromatic rings, one or more of which can be heterocyclic, are present. The difficulty of desulfurization generally increases with the structural complexity of the molecule. That is, refractory behavior is particularly accentuated in complex sulfur-bearing heterocycles, such as dibenzothiophene (DBT, $C_{12}H_8S$).

Much of the residual post-HDS organic sulfur in fossil fuel refining intermediates and combustible products is thiophenic sulfur. The majority of this residual thiophenic sulfur is present in DBT and derivatives thereof having one or more alkyl or aryl groups attached to one or more carbon atoms present in one or both flanking benzo rings. DBT itself is accepted as a model compound illustrative of the behavior of the class of compounds encompassing DBT and derivatives thereof in reactions involving thiophenic sulfur (Monticello and Finnerty, *Ann. Rev. Microbiol.*, 39 : 371–389 (1985)). DBT and derivatives thereof can account for a significant percentage of the total sulfur content of particular crude oils, coals and bitumen. For example, these sulfur-bearing heterocycles have been reported to account for as much as 70 wt % of the total sulfur content of West Texas crude oil, and up to 40 wt % of the total sulfur content of some Middle East crude oils. Thus, DBT is considered to be particularly relevant as a model compound for the forms of thiophenic sulfur found in fossil fuels, such as crude oils, coals or bitumen of particular geographic origin, and various refining intermediates and fuel products manufactured therefrom (Monticello and Finnerty (1985), supra). Another characteristic of DBT and derivatives thereof is that, following a release of fossil fuel into the environment, these sulfur-bearing heterocycles persist for long periods of time without significant biodegradation. Gundlach et al., *Science* 221 : 122–129 (1983). Thus, most prevalent naturally occurring microorganisms do not effectively metabolize and break down sulfur-bearing heterocycles.

Biocatalytic desulfurization (biocatalysis or BDS) is the excision (liberation or removal) of sulfur from organosulfur compounds, including refractory organosulfur compounds such as sulfur-bearing heterocycles, as a result of the oxidative, preferably selective, cleavage of carbon-sulfur bonds in said compounds by a biocatalyst. BDS treatment yields the desulfurized combustible hydrocarbon framework of the former refractory organosulfur compound, along with inorganic sulfur substances which can be readily separated from each other by known techniques such as fractional distillation or water extraction. For example, DBT is converted into 2-hydroxybiphenyl when subjected to BDS treatment. A suitable biocatalyst for BDS comprises Sphingomonas sp. strain AD109 or an enzyme preparation derived therefrom, optionally, in combination with one or more additional non-human desulfurizing organisms (e.g., microorganisms); or an enzyme preparation derived from such an organism. Suitable additional desulfurizing organisms include those described above.

The specific activity of a given biocatalyst is a measure of its biocatalytic activity per unit mass. Thus, the specific activity of a particular biocatalyst depends on the nature or identity of the microorganism used or used as a source of biocatalytic enzymes, as well as the procedures used for preparing and/or storing the biocatalyst preparation. The concentration of a particular biocatalyst can be adjusted as desired for use in particular circumstances. For example, where a culture of living microorganisms, such as Sphingomonas sp. strain AD109, is used as the biocatalyst preparation, a suitable culture medium lacking a sulfur source other than sulfur-bearing heterocycles can be inoculated with suitable microorganisms and grown until a desired culture density is reached. The resulting culture can be diluted with additional medium or another suitable buffer, or microbial cells present in the culture can be retrieved e.g., by centrifugation, and resuspended at a greater concentration than that of the original culture. The concentrations of microorganism and enzyme biocatalyst can be adjusted similarly. In this manner, appropriate volumes of biocatalyst preparations having predetermined specific activities and/or concentrations can be obtained.

In the biocatalytic desulfurization stage, the liquid fossil fuel containing sulfur-bearing heterocycles is combined with the biocatalyst. The relative amounts of biocatalyst and liquid fossil fuel can be adjusted to suit particular conditions, or to produce a particular level of residual sulfur in the treated, deeply desulfurized fossil fuel. The amount of biocatalyst preparation to be combined with a given quantity of liquid fossil fuel will reflect the nature, concentration and specific activity of the particular biocatalyst used, as well as the nature and relative abundance of inorganic and organic sulfur compounds present in the substrate fossil fuel and the degree of deep desulfurization sought or considered acceptable.

The method of desulfurizing a fossil fuel of the present invention involves two aspects. First, a host organism or biocatalytic preparation obtained therefrom is contacted with a fossil fuel to be desulfurized. This can be done in any appropriate container, optionally fitted with an agitation or mixing device. The mixture is combined thoroughly and maintained or allowed to incubate for a sufficient time to allow for biocatalysis. In one embodiment, an aqueous emulsion or microemulsion is produced with an aqueous culture of the organism or enzyme fraction and the fossil fuel, allowing the organism to propagate in the emulsion while the expressed biocatalyst cleaves carbon-sulfur bonds.

Variables such as temperature, pH, oxidation levels, mixing rate and rate of desulfurization will vary according to the nature of the biocatalyst used. Optimal parameters can generally be determined through no more than routine experimentation.

When the fossil fuel is a liquid hydrocarbon, such as petroleum, the desulfurized fossil fuel and the aqueous phase can form an emulsion. The components of such emulsions can be separated by a variety of methods, such as those described in U.S. Pat. No. 5,358,870 and U.S. patent application Ser. No. 08/640,129, which are incorporated herein by reference. For example, some emulsions reverse spontaneously when maintained under stationary conditions for a suitable period of time. Other emulsions can be reversed by adding an additional amount of an aqueous phase. Still other emulsions can be separated by the addition of a suitable chemical agent, such as a demulsifying agent or by employing suitable physical conditions, such as a particular temperature range.

The biocatalyst can be recovered from the aqueous phase, for example, by centrifugation, filtration or lyophilization. When the biocatalyst is a microorganism, the biocatalyst can be resuspended in fresh sulfur-free nutrient medium and/or any fresh microorganism culture as necessary to reconstitute or replenish to the desired level of biocatalytic activity. The biocatalyst can then be reintroduced into the reaction system.

Several suitable techniques for monitoring the rate and extent of desulfurization are well-known and readily available to those skilled in the art. Baseline and time course samples can be collected from the incubation mixture, and prepared for a determination of the residual organic sulfur in the fossil fuel. The disappearance of sulfur from organosulfur compounds, such as DBT, in the sample being subjected to biocatalytic treatment can be monitored using, e.g., X-ray fluorescence (XRF) or atomic emission spectrometry (flame spectrometry). Preferably, the molecular components of the sample are first separated, e.g., by gas chromatography.

Without being limited to any particular mechanism or theory, it is believed that the pathway of the desulfurization reaction in Sphingomonas sp. strain AD109 and other desulfurizing organisms, such as Rhodococcus sp. IGTS8, is set forth below:

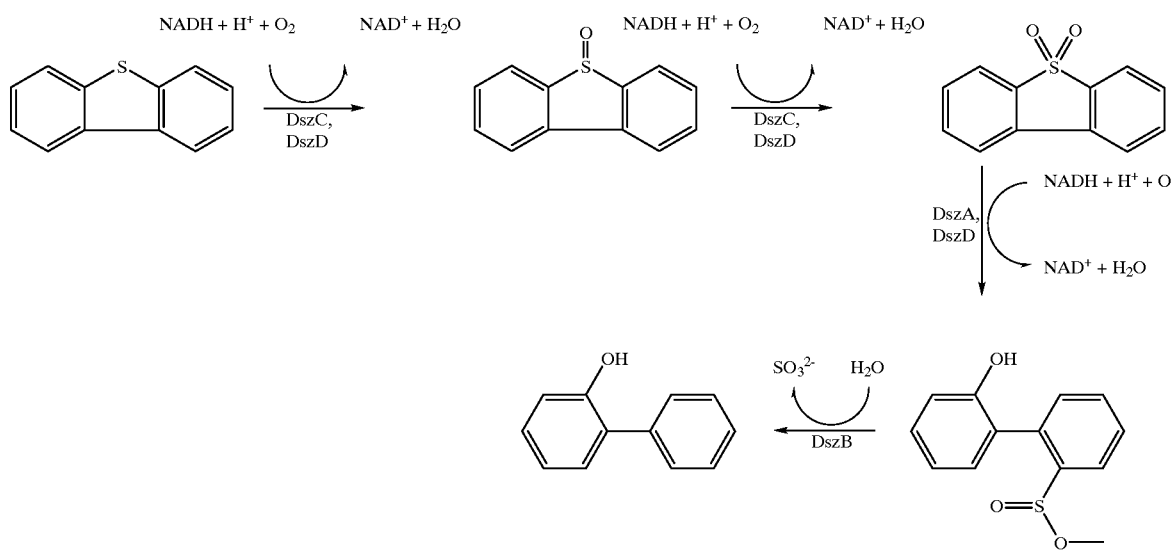

Here the flavin reductase provides an electron transport chain which delivers, via $FMNH_2$, the reducing equivalents from NADH (or other electron donor) to the enzymes DszC and/or DszA. The enzyme DszC is responsible for the biocatalysis of the oxidation reaction of DBT to $DBTO_2$. The enzyme DszA is responsible for the reaction of $DBTO_2$ to 2-(2-hydroxyphenyl)benzenesulfinate (HPBS). The enzyme DszB catalyzes the conversion of HPBS to 2-hydroxybiphenyl and inorganic sulfur.

Another method of use of the Sphingomonas desulfurization enzymes, or mutants, homologues or active fragments thereof, is as a biocatalyst for the oxidation of organic compounds, such as substituted or unsubstituted dibenzothiophenes. The method comprises the steps of (1) contacting the organic compound with an aqueous phase containing a Sphingomonas-derived biocatalyst comprising at least one enzyme capable of catalyzing at least one step in the oxidative cleavage of carbon-sulfur bonds, thereby forming an organic compound and aqueous phase mixture; (2) maintaining the mixture of step (1) under conditions sufficient for oxidation of the organic compound by the biocatalyst, thereby resulting in an oxidized organic compound, and, optionally, separating the oxidized organic compound from the aqueous phase. In one embodiment, the organic compound is a heteroorganic compound, such as an organonitrogen compound or an organosulfur compound. In one embodiment, the organic compound is an organosulfur compound which is a component of a fossil fuel, such as petroleum or a petroleum distillate fraction. In a second embodiment, the organic compound is a substituted or unsubstituted indole, as described in U.S. Provisional Patent Application Ser. No. 60/020563, filed Jul. 2, 1996, which is incorporated herein by reference.

The enzyme encoded by the nucleotide sequence of ORF-3 catalyzes the oxidation of dibenzothiophene to dibenzothiophene-5,5-dioxide (dibenzothiophene sulfone), and the enzyme encoded by the nucleotide sequence of ORF-1 catalyzes the oxidation of dibenzothiophene-5,5-dioxide to 2-(2-hydroxyphenyl)benzenesulfinate (also referred to as "HPBS"). In one embodiment the biocatalyst comprises the enzyme encoded by ORF-3, or a mutant, homologue or active fragment thereof; the organosulfur compound is substituted or unsubstituted dibenzothiophene; and the oxidized organosulfur is a substituted or unsubstituted dibenzothiophene-5,5-dioxide or dibenzothiophene-5-oxide (dibenzothiophene sulfoxide). In another embodiment the biocatalyst comprises the enzymes encoded by ORF-1 and ORF-3, or a mutant, homologue or active fragment thereof; the organosulfur compound is a substituted or unsubstituted dibenzothiophene; and the oxidized organosulfur compound is a substituted or unsubstituted 2-(2-hydroxyphenyl)benzenesulfinate. In yet another embodiment, the biocatalyst comprises the enzyme encoded by ORF-1 or a mutant, homologue or active fragment thereof; the organosulfur compound is a substituted or unsubstituted dibenzothiophene-5,5-dioxide; and the oxidized organosulfur compound is a substituted or unsubstituted 2-(2-hydroxyphenyl)benzenesulfinate.

The oxidized organosulfur compound can, optionally, be further processed, for example, via a non-biological process or an enzyme-catalyzed reaction. In one embodiment, the oxidized organosulfur compound is desulfurized in a process employing suitable desulfurization enzymes from an organism other than a Sphingomonas.

The biocatalyst can be an organism, such as Sphingomonas sp. strain AD109, a desulfurizing mutant thereof, or a recombinant organism or enzyme preparation, as discussed above. When the organosulfur compound is a component of a fossil fuel, suitable reaction conditions and fossil fuel sources can be determined as described above.

The invention will now be further illustrated by the way of the following examples.

EXAMPLES

Figure 11:
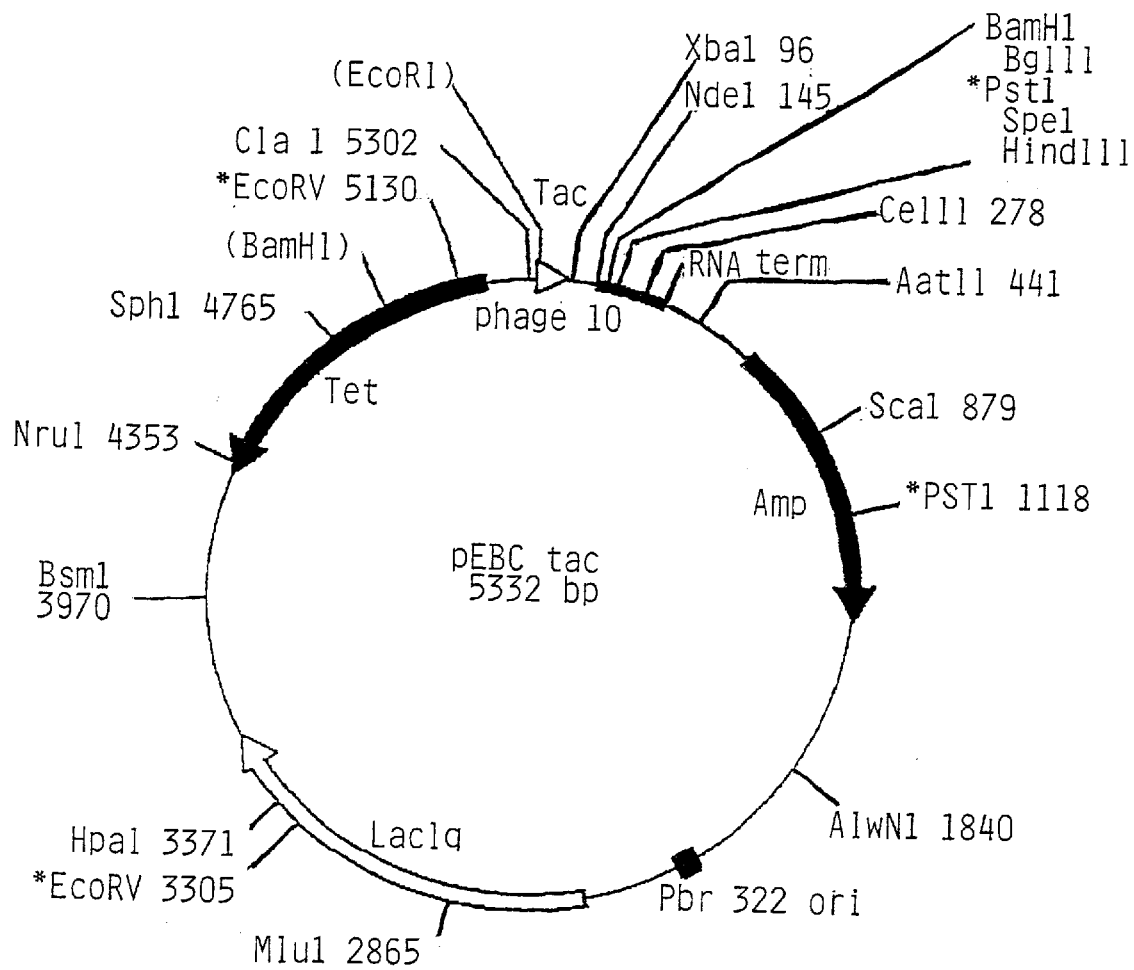
FIG. 11 is a physical map of the plasmid pEBCtac.

General Methods and Materials
Bacterial strains and plasmids $E.$ $coli$ DH10β (F$^-$ mcrA Δ(mrr-hsdRMS-mcrBC)phi80dlacZAM15 ΔlacX74 deoR recA1 endA1 araΔ139 A(ara, leu)7697 galU galK lambda$^-$ rpsL nupG; Gibco-BRL, Gaithersburg, Md.) was used as the cloning host. Plasmids pUC18 (Ap$^R$; Vieria and Messing, $Gene$ 19 259–268, (1982)), pOK12 (Km$^R$; Vieria and Messing, $Gene$ 100 : 189–194 (1991)) and pSL1180 (Ap$^R$; Brosius, $DNA$ 8 : 759, (1989)) were used as cloning vectors. Plasmid pEBCtac (Ap$^R$ Tc$^R$ lacI$^q$ tac, shown in FIG. 11, was used to overexpress the Sphingomonas dszB in $E.$ $coli$.

Media and Reagents

Luria broth (LB) medium was routinely used to propagate $E.$ $coli$. LB medium is 1% tryptone (Difco), 0.5% yeast extract (Difco) and 0.5% NaCl. Rich medium (RM) was used to propagate Sphingomonas strain AD109. RM medium is 0.8% nutrient broth, 0.05% yeast extract and 1% glucose. 2YT medium, used in gene expression studies, is 1.6% tryptone, 1% yeast extract and 0.5% NaCl. Basal salts medium (BSM-glucose) contained the following (per liter): phosphate buffer 100 mmol (pH 7.2); glucose, 20 g: NH$_4$Cl, 2 g; MgCl$_2$.6H$_2$O, 644 mg; MnCl$_2$.4H$_2$O, 1 mg; nitriloacetic acid, 0.1 g; FeCl$_2$.4H$_2$O, 2.6 mg; Na$_2$B$_4$O$_y$.10H$_2$O, 0.1 mg; CuCl$_2$.2H$_2$O, 0.15 mg; Co(NO$_3$)$_2$.6H$_2$O, 0.125 mg; ZnCl$_2$, 2.6 mg; CaCl$_2$.2H$_2$O, 33 mg; (NH$_4$)$_6$Mo$_7$O$_{24}$.4H$_2$O, 0.09 mg; and EDTA, 1.25 mg. When required the sulfur source was either 2 mM MgSO$_4$, 300 μM Dibenzothiophene (DBT), 300 μM Dibenzothiophene sulfone (DBTO$_2$) or 300 μM 2-(2-hydroxyphenyl) benzenesulfinate (HPBS). For solid media, agar or agarose was added at a concentration of 1.5% (wt/wt). The antibiotic concentrations for $E.$ $coli$ were as follows: ampicillin, 100 μg/ml; kanamycin, 30 μg/ml; tetracycline, 10 μg/ml.

DNA Methods

Restriction enzymes and T4 DNA ligase were purchased from New England Biolabs, Inc. (Beverly, Mass.) and used as recommended by the supplier. Chromosomal DNA was isolated by the method described by Woo et al., $BioTechniques$ 13: 696–698 (1992). Small scale plasmid preparations from $E.$ $coli$ were carried out as described by Birboim and Doly, $Nuc.$ $Acids$ $Res.$ 7: 1513–1523 (1979). Larger scale DNA preparations were carried out with Midi-prep columns from Qiagen (Chatsworth, Calif.). DNA fragments were purified from agarose gels after electrophoretic separation by the method of Vogelstein and Gillespie ($Proc.$ $Natl.$ $Acad.$ $Sci.$ $USA$ 76: 615–619 (1979). DNA fragments were cloned into vectors by using techniques described by Sambrook et al.

Degenerate oligonucleotide probes were end-labeled using standard digoxygenin protocols according to the Boehringer Mannheim DIG Oligonucleotide 3'-End Labeling Kit (Cat. No. 1362372). Hybridization was performed in 5× SSC with blocking solution containing 50% ultrapure deionized formamide at 42° C. overnight (16 hr). Detection of hybrids was by enzyme immunoassay according to the Boehringer Mannheim Nonradioactive DIG DNA Labeling and Detection Kit (Cat. No. 1093657).

DNA samples were sequenced by SeqWright (Houston, Tex.) using a dye-terminator cycling sequencing kit from Perkin Elmer and the 373A and 377 ABI automatic DNA sequencer. The sequence was extended by synthesizing overlapping oligonucleotides to previously read sequence. The synthesized oligonucleotides were used as primers for continuing sequence reactions. Sequencing reads were assembled and edited to 99.99% accuracy using Genecode's $Sequencher$, version 3.0 computer software.

DNA and protein sequence analysis was performed with the MacVector software program (Oxford Molecular Group, Campbell, Calif.). Nucleotide and amino acid sequences were compared to sequences in the available databases using BLAST. The Wisconsin Genetics Computer Group (GCG) software (Devereux et al., $Nucl.$ $Acids$ $Res.$ 12 : 387–395 (1984)) program GAP was used to generate comparisons of the protein sequences.

Transformation of $E.$ $coli$

Plasmid DNA was introduced into $E.$ $coli$ DH10β by electroporation. Competent ElectroMAX DH10β (Gibco-BRL, Gaithersburg, Md.) were used according to the manufacturer's suggestions.

Preparation of cell-free extracts

Cells grown in the appropriate medium were concentrated to an optical density at 600 nm of 50 by centrifugation and resuspended in 10 mM phosphate buffer (pH 7.0). Cells were disrupted in a French press and debris was removed by centrifugation at 32,000× g for 20 min. Cell lysates were stored on ice at 4° C.

Desulfurization assays and analytical analysis

HPBS desulfinase activity was assayed by the ability of cell-free lysates to convert HPBS (substrate) to 2-HBP (product) in a one hour assay at 30° C. The amounts of product made and substrate consumed during the reaction were quantitated by high-pressure liquid chromatography (HPLC) analysis. HPBS desulfinase activity was also measured by fluorescence spectroscopy. In a typical enzyme assay, enzyme activity is determined by the change in fluorescence at an excitation wavelength of 288 nm and an emission wavelength of 414 nm as HPBS is converted to 2-HBP. The assay is initiated by the addition of 20–100 μg total protein to a 3 mL solution of 200 μM HPBS in 50 mM phosphate buffer pH 7.5 containing 0.1 M NaCl.

Expression studies

E. coli DH10β harboring the Sphingomonas dszB overexpression plasmid pDA296 was inoculated into 100 ml of 2YT medium containing ampicillin and allowed to grow with shaking at 30° C. At an $OD_{600}$ of approximately 0.3, the culture was divided into two parts. One half of the culture was induced by the addition of isopropylthio-β-galactoside (IPTG) (final conc. 1 mM) and the remaining culture was used as an uninduced control (no IPTG was added). Following incubation for an additional 3 hr, both cultures were harvested and cell-free lysates were prepared.

Protein purification and N-terminal sequencing

Sphingomonas AD109 cell paste was resuspended in an approximately equal weight of 25 mM phosphate buffer pH 7.5 containing 0.1 mM EDTA, 0.5 mM dithiothreitol (DTT), 10 μg/mL DNAse and 1 mM phenylmethylsulfonyl fluoride and passed through a French press mini-cell at about 20,000 psi. Cell debris was removed by centrifugation and the cell lysate was fractionated over an Econo-Pac High Q cartridge manufactured by Bio-Rad. A linear 0–0.5 M NaCl gradient was used to elute the bound protein into fractions. The active fractions were identified by a 2-HBP fluorescence enzyme assay (excitation/emission wavelengths set at 288/414 nm). The active fractions were pooled and desalted over a Bio-Rad P6 gel filtration cartridge, diluted to 1.7 M ammonium sulfate and fractionated over a Phenyl Superose HR 5/5 column manufactured by Pharmacia. A linear 1.7–0.0 M ammonium sulfate gradient was used to elute protein into fractions. Active fractions were identified and pooled as described above. Identity and purity of the AD109 HPBS desulfinase protein was also determined by SDS-PAGE and Western blots using antibodies generated against the DszB protein from *Rhodococcus erythroplis* strain IGTS8. N-terminal microsequencing of the HPBS desulfinase was carried out by Edman degradation after transfer of the purified protein to a polyvinylidene difluoride (PVDF) membrane.

SDS-PAGE and Western Blot Analysis

Protein separations were done with Novex (San Diego, Calif.) precast 10% polyacrylamide gels with Tris-Glycine-sodium dodecyl sulfate (SDS) (Laemmli) running buffer. Western blot analysis was carried out by first transferring the proteins electrophoretically to nitrocellulose membranes as recommended by Biorad (Hercules, Calif.). Blots were treated with antisera raised against the purified IGTS8 DszB protein (primary antibody) and then with goat anti-rabbit antisera conjugated to horseradish peroxidase as the secondary antibody. Finally, the proteins were detected with a horseradish peroxidase catalyzed chemiluminescent reaction.

Example 1

Soil enrichments and isolation of a microorganism that can use HPBS as a sole sulfur source Three independent soil samples from oil-contaminated sites were used to perform soil enrichments for microorganisms able to use HPBS as a sole sulfur source. Approximately 5 grams of each soil sample was placed into a sterile 250 ml flask along with 50 ml of BSM Glucose medium containing HPBS (300 μM) as the sole source of sulfur. Following incubation for 96 hrs at 30° C., a 3 ml sample of each enrichment was transferred to fresh BSM Glucose medium containing HPBS. After 72 hrs, one of the three flasks (flask #3) showed visible turbidity, while the two remaining flasks showed no visible increase in turbidity (even after more than a week of incubation). Microscopic analysis of the contents of flask #3 revealed the presence of a mixed population of bacterial cells (i.e., sessile and motile rods of varying shapes; large and small coccoid shaped bacteria). After repeated liquid subculture enrichments with HPBS as the sole sulfur source, the contents of the flask was plated onto several RM and LB agar plates. Following incubation at 30° C., a variety of microorganisms with different colony morphologies was present. Analysis of individual colonies from these plates identified a pure isolate that efficiently used HPBS as a sole sulfur source. This strain, designated AD109, was selected for further analysis.

Example 2

Characterization and identification of strain AD109

The HPBS utilizing strain AD109 is a Gram-negative, motile rod that forms distinctive yellow colonies on agar plates. It grows somewhat poorly on LB agar, but grows rather well on RM agar plates. Like Rhodococcus IGTS8, strain AD109 also has the ability to produce clearing zones on a BSM Glucose DBT-sulfone plate. The optimal growth temperature of AD109 was found to be between 30 and 37° C.

Based on fatty acid analysis (Acculab, Inc., Newark, Del.), this strain was identified as a Sphingomonas species. Strain AD109 was a "good" match to *S. paucimobilis* (formerly *Pseudomonas paucimobilis*) based on its "similarity index". The similarity index is a mathematical expression of the extent to which the fatty acid profile of a given unknown matches the mean profile for an organism in the TSBA database. Strain AD109 had an index value of 0.426 which indicates that it is from a strain of a species that differs significantly from those represented in the database. A similarity index of 0.5 or above is considered to be an "excellent" match (a value of 1.0 being the highest possible). On the other hand, an index below 0.3 indicates that the sample is from a species that is not likely to be in the database. Based on 16S rRNA sequence analysis and the presence of sphingoglycolipids, Yabuuchi et al. (*Microbiol. Immunol.* 34 : 99–119 (1990)) proposed that *P. paucimobilis* be reclassified and placed into the genus Sphingomonas.

Example 3

Growth characteristics of Sphingomonas species strain AD109

Evidence for the existence of an HPBS desulfinase activity was demonstrated by monitoring the supernatant of a AD109 culture growing in BSM Glucose HPBS (300 μM). By the time the culture was well into stationary phase all of the HPBS had been converted with no apparent accumulation of identifiable intermediates. There was, however, a transient production of a small amount of 2-HBP, as determined by HPLC analysis, which also disappeared with time. This preliminary result suggested that AD109 may also be capable of metabolizing 2-HBP. Sphingomonas strain AD109 was also capable of utilizing DBT-sulfone (DBTO$_2$) as a sole sulfur source. The ability to utilize DBT-sulfone as a sole sulfur source suggests that strain AD109 may also contain a gene that encodes DBT-sulfone monooxygenase activity.

During the course of growth studies it was discovered that strain AD109 could utilize DBT as a sole sulfur source. While growing with DBT, however, the culture supernatant takes on a very characteristic orange/brown color with an absorption maximum of approximately 470 nm. Orange-colored oxidation products have been previously identified in a number of Pseudomonas species that are capable of degrading DBT (Monticello et al., *Appl. Environ. Microbiol.* 49 : 756–760 (1985)); Foght and Westlake, *Can. J. Microbiol.* 36 : 718–724 (1990)). No such color development was detected in cultures growing with either HPBS or DBT-sulfone as sulfur sources.

Example 4

Demonstration of HPBS desulfinase activity in AD109 cell-free lysates

A cell-free lysate prepared from a culture of Sphingomonas strain AD109 (grown in BSM Glucose medium containing HPBS) was used in a time course study to examine the rate at which HPBS is converted to 2-HBP. As presented in FIG. 4, at a protein concentration of 4 mg/ml there was a linear increase in 2-HBP production and a concomitant disappearance of HPBS.

The product of the in vitro reaction was confirmed to be 2-HBP by a spectral comparison to authentic 2-HBP. The ultraviolet absorption spectrum of the suspected 2-HBP peak produced by the action of the AD109 lysate is virtually identical with that of the 2-HBP standard. Furthermore, the molecular weight of the unknown compound was exactly that of authentic 2-HBP as determined by GC-MS analysis.

Example 5

Purification of the HPBS desulfinase from Sphingomonas AD109

HPBS desulfinase was purified from AD109 by a series of chromatographic steps using a Bio-Rad low pressure column chromatography Econo system and a Pharmacia FPLC (Gray et al., *Nature Biotech.* 14 : 1705–1709 (1996)). The steps included fractionation over an anion exchange resin followed by a hydrophobic interaction column chromatography step. These protein purification steps are described above. A 15–20 fold purification was achieved in these two steps which is comparable to protein preparations from a Rhodococcus IGTS8 lysate.

The molecular weight of this protein by SDS-PAGE was estimated to be 40,000 daltons, which is approximately the same size as DszB purified from IGTS8. Western analysis demonstrated that the purified protein shows some cross-reactivity with anti-DszB antisera.

Nonlinear regression analysis of an enzyme progress curve was performed according to the general method described by Duggleby, *Methods Enzymol.* 249 : 61–90 (1995). The analysis involves fitting the integrated Michealis-Menton rate equation $V_m*t=y-K_m*1\,n(1-y/[A]_0)$ to concentration vs. time data from the enzyme catalyzed reaction of 2-(2-phenyl)benzenesulfinate to 2-hydroxybiphenyl monitored to completion by fluorescence. The semi-pure protein sample was generated by fractionation of a crude lysate over Q Sepharose Fast Flow resin (Pharmacia) by a linear 0–0.5 M NaCl gradient, as discussed in more detail above. The purity of the active fraction was determined by SDS-PAGE. Pure enzyme is not necessary for the application of enzyme progress curve analysis, however, the calculation of $k_{cat}(V_m=[E]_t*k_{cat})$ was limited to a value range as only a crude estimate of the enzyme concentration was available. The reaction conditions were as follows. A 3 mL reaction solution containing 1 FM HPBS and 0.1 M NaCl in 50 mM phosphate at pH 7.5 and 30° C. was initiated by the addition of 0.023 mg total protein and was monitored for 30 min by fluorescence at an excitation wavelength of 288 nm and an emission wavelength of 414 nm. The data were fit to the equation using the Kaleidagraph data analysis/graphics application (Abelleck Software).

Based on the kinetic parameters calculated from the enzyme progress assay ($K_m$=0.3 $\mu$M and $V_m$=0.1 $\mu$M/min), the minimum $k_{cat}$=0.5 min$^{-1}$. However, a more realistic value would be on the order of 2 min$^{-1}$ in view of the fact that the preparation is estimated to be about 25% pure. Therefore, the HPBS desulfinase from Sphingomonas AD109 appears to be comparable to that from Rhodococcus IGTS8 with the possibility of a higher catalytic efficiency ($k_{cat}/K_m$).

The N-terminal amino acid sequence of the purified Sphingomonas HPBS desulfinase was also determined. Protein microsequencing using standard methods of analysis resulted in the following amino acid sequence:

```
  1          10           20
TTDIHPASAA  SSPAARATIT  YS  (SEQ ID NO.: 7)
```

A comparison of the putative AD109 HPBS desulfinase N-terminal sequence with that of the N-terminus of the IGTS8 DszB protein revealed that 9 out the 22 amino acid residues were identical (41%). In order to determine whether the purified protein is, in fact, the Sphingomonas desulfinase protein, a degenerate (192 permutations) 17-mer oligonucleotide probe with the following sequence: 5' ACN GAY ATH CAY CCN GC 3' (SEQ ID NO.: 8), was designed based on the determined N-terminal sequence. Following labeling with a non-isotopic label this probe was used in hybridization studies using the cloned Sphingomonas AD109 HPBS desulfinase gene (see below) and the dszB gene from IGTS8 (Denome et al., *J. Bacteriol.* 176 : 6707–6716 (1994); Piddington et al., *App. Environ. Microbiol.* 61 : 468–475 (1995). The labeled oligonucleotide probe hybridized to the cloned Sphingomonas HPBS desulfinase gene which indicated that the correct protein had been purified. However, no signal was detected in the lane containing a fragment harboring the Rhodococcus dsz B gene.

Example 6

Cloning of the Sphingomonas AD109 HPBS desulfinase gene

Strain AD109 has been shown to be capable of using HPBS as a sole sulfur source and clearing a DBTO$_2$ plate. On the assumption that the gene(s) responsible for DBTO$_2$ clearing and HPBS desulfinase activity are genetically closely linked, as they are in Rhodococcus IGTS8, a cloning scheme was devised to isolate the HPBS desulfinase gene from Sphingomonas strain AD109. Total genomic DNA from strain AD109 was digested with either EcoRI, BamHI, and HindIII and the resulting fragments were ligated into pUC18 or pSL1180. Following transformation of *E. coli*

DH10β, approximately 1000–2000 Lac-negative, ampicillin-resistant colonies of each library were screened for the ability to clear a DBTO₂ plate. No clearing colonies were detected amongst transformants derived from either the EcoRI or BamHI libraries. However, two clearing colonies were detected utilizing the HindIII library and one clearing colony was detected with the NotI library. Based on restriction endonuclease profiles, both colonies from the HindIII library contained the same large fragment (~20 kb). Furthermore, there was measurable HPBS desulfinase activity in cell-free lysates of these strains.

The single clearing colony from the NotI library contained a 6.5 kb fragment which, according to restriction endonuclease mapping, overlapped the 20 kb HindIII fragment. This clone also contained measurable HPBS desulfinase activity.

Subcloning analysis localized the genes responsible for DBTO₂ clearing and HPBS desulfinase activity to a 6 kb HindIII-NotI fragment. A smaller 2.7 kb HindIII-SmaI fragment was subsequently found to retain HPBS desulfinase activity, but lost the ability to clear a DBTO₂ plate. It is likely, therefore, that the gene that confers the ability to produce clearing zones on a DBT-sulfone plate spans the SmaI site.

Example 7

DNA sequence analysis of the Sphingomonas sp. strain AD109 desulfurization gene cluster The nucleotide sequence of a 4144 bp region which encompasses the AD109 HPBS desulfinase gene was determined from both DNA strands and is present in FIG. 6 (SEQ ID NO.: 12). The overall G+C content of the first 3837 base pairs of the AD109 sequence is 64.5%, a value which is consistent with the range of G+C values (61.7–67.2%) reported for various Sphingomonas species (Yabuuchi et al. (1990)). A comparison of the AD109 nucleotide sequence with the IGTS8 dsz sequence by DNA matrix analysis revealed that a considerable amount of homology exists between the two sequences as evidenced by the presence of a near continuous diagonal line.

Open reading frame analysis of the AD109 sequence revealed the presence of a number of ORFs on both DNA strands, but of these, only three contained the codon-choice pattern characteristic of microorganisms with G-C rich genomes (West et al., *Nucl. Acids Res.* 16: 9323–9334 (1988)). All three identified ORFs were in the same transcriptional orientation. A strong preference for codons with either G or C occurred in positions 1 and 3. The first codon position of all three ORFs ranged from 67 to 72%, while the third codon position of all three ORFs ranged from 79–81%. In addition, the predicted translation initiation sites of all three ORFs are preceded by sequences that resemble a consensus ribosome binding site.

The entire nucleotide sequence of the AD109 region was used to conduct a BLAST search of the available DNA databases. The Rhodococcus IGTS8 dsz genes were the highest scoring sequences that demonstrated homology to the Sphingomonas sequences. The only other nucleotide sequence that demonstrated any significant homology to the Sphingomonas DNA, was the *Streptomyces pristinaespiralis* snaA gene which encodes the large subunit of the PII$_A$ synthase (Blanc et al., *J. Bacteriol.* 177 : 5206–5214 (1995)). The Sphingomonas dszA and *S. pristinaespiralis* snaA genes demonstrate about 60% identity over a 800 bp region proximal to the 5' end of each gene.

The first ORF (bp 442–1800; FIGS. 1A–1D) is 71% identical (at the nucleotide level) to the Rhodococcus dszA gene. The primary translation product of ORF-1 would encode a protein (Sphingomonas DszA or Dsz(S)) that contains 453 amino acids with a predicted molecular weight of 50,200. More importantly, this protein demonstrates considerable homology to the amino acid sequence of Rhodococcus DszA (Dsz(R), SEQ ID NO.: 9) over the entire length of the polypeptide (76% identity and 87% similarity; FIG. 8). The protein databases were also searched with the Sphingomonas DszA protein sequences. Aside from the DszA protein of Rhodococcus IGTS8, several other proteins demonstrated significant homology to the Sphingomonas DszA protein. These include a hypothetical 49.3 kD protein in the IDH-DEOR intergenic region of *Bacillus subtilis* which showed 45% identity over 382 residues, the PII$_A$ synthase SnaA subunit of *S. pristineaspiralis* (Blanc et al.,*J. Bacteriol.* 177 : 5206–5214 (1995)) which was 49% identical over 358 residues and the nitrilotriacetate monooxygenase of *Chelatobacter heintzii* (Xu et al., Abstracts of the 95th General Meeting of the American Society for Microbiology, Q-281) which was 50% identical over the 335 residues examined.

The stop site of the Sphingomonas ORF-1 shows a 4-bp overlap with the translation start site of the second ORF (bp 1800–2906; FIGS. 2A–2C), which shows a high degree of homology to the Rhodococcus IGTS8 dszB gene (67% identity). It was determined that the primary translation product of ORF-2 would encode a 369-amino acid polypeptide with a predicted molecular weight of 40,000 (Sphingomonas DszB or Dsz(S)). At the amino acid level this putative protein is 66% identical (75% similarity) to the Rhodococcus HPBS desulfinase protein DszB (DszB(R), SEQ ID NO: 10), as shown in FIG. 9. Except for the IGTS8 DszB protein, a BLAST search with the Sphingomonas DszB sequence did not identify any other significant homologous sequences in the available databases. The predicted N-terminus of the Sphingomonas DszB protein matches identically the N-terminus of the HPBS desulfinase purified from AD109 cell lysates, except that the amino-terminal methionine was absent. Removal of the methionine residue has been shown to occur when the second amino acid is Ala, Ser, Gly, Pro, Thr or Val (Hirel et al., *Proc. Nat. Acad. Sci. USA* 86 8247–8251 (1989)).

The stop site of the Sphingomonas dszB gene also shows a 4-bp overlap with the translation start site of the third ORF. This ORF (bp 2906–4141; FIGS. 3A–3C), shows significant homology to the Rhodococcus IGTS8 dszC gene. For example, over the first 931 bp, this ORF is 696 identical to the IGTS8 dszC gene and the N-terminus of the protein predicted by this sequence (Sphingomonas DszC, DszC(S)) is 67% identical to the N-terminus of Rhodococcus DszC (DszC(R), SEQ ID NO: 11), as shown in FIG. 10. A BLAST search of the protein databases with the available Sphingomonas DszC sequence identified a number of proteins in addition to the IGTS8 DszC protein. The Sphingomonas DszC protein is 32% identical (over 199 residues) to Isobutylamine N-Hydroxylase (IBAH) of *Streptomyces viridifaciens*. It has previously been shown that IBAH exhibits the greatest similarity to the IGTS8 DszC protein (Parry et al., *J. Bacteriol.*, 179: 409–416 (1997)). In addition, the AD109 DszC protein showed variable homology to a number of acyl coenzyme A dehydrogenases. For example, the N-terminal 300 residues of the Sphingomonas DszC protein is 29% identical to the acyl CoA dehydrogenase of *B. subtilis*.

The sequences (400 bp) directly upstream of the dszA start site contain regulatory elements (i.e., promoter elements) that control transcription of the AD109 dsz gene cluster. A comparison of this potential promoter region with the IGTS8 dsz promoter region failed to reveal any significant homology. It has been shown that the IGTS8 dsz promoter region encompasses a region of potential diad symmetry that may contain an operator (Li et al., *J. Bacteriol.* 178 : 6409–6418 (1996)). An examination of the AD109 sequences directly upstream of dszA revealed no such palindromic sequence.

Example 8

Expression of the Sphingomonas dszB gene in *E. coli*

Figure 7:
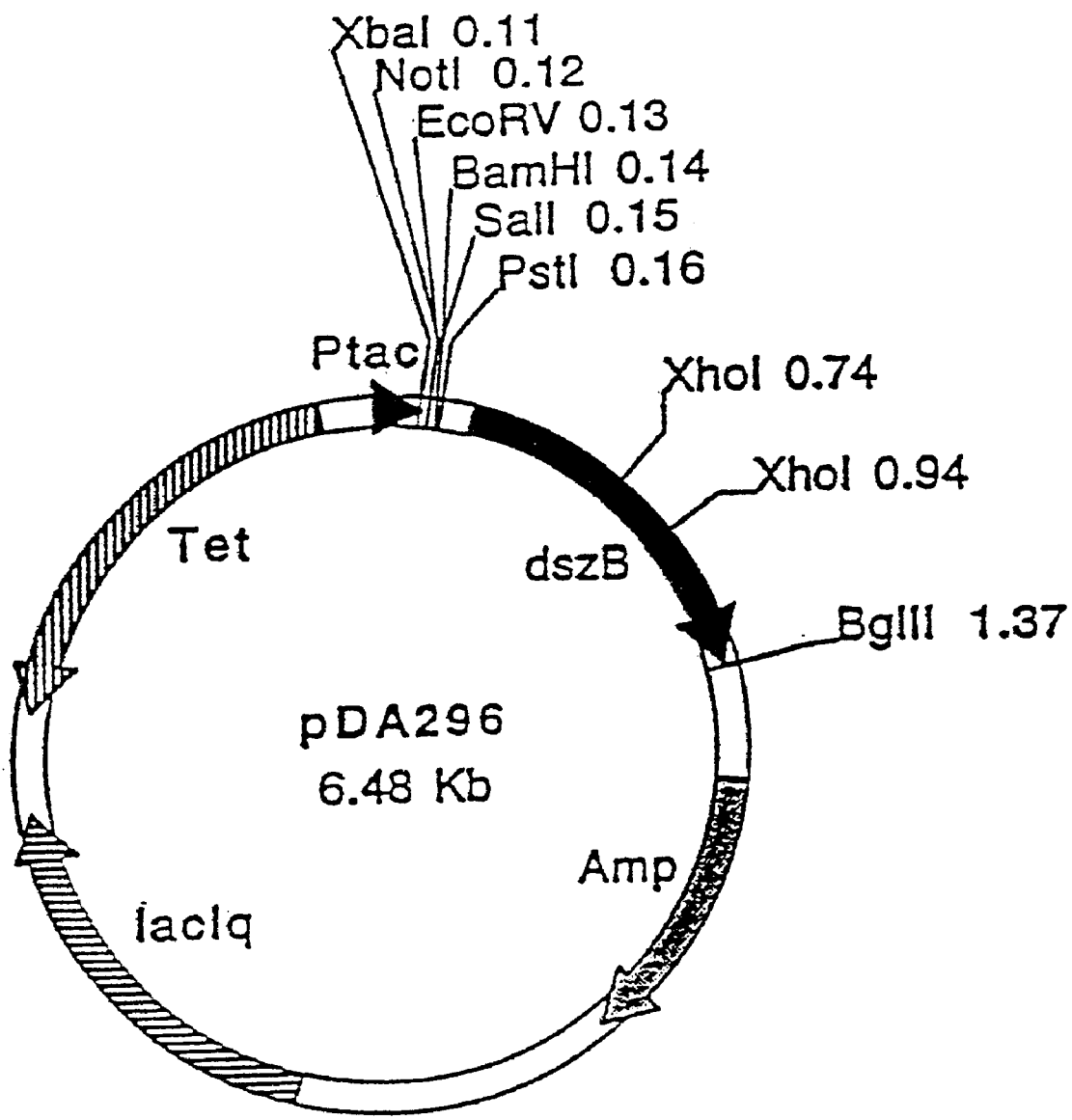
FIG. 7 is a physical map of the plasmid pDA296.

The AD109 dszB gene was subcloned into the tac promoter expression vector, pEBCtac, in two steps. The first step involved cloning a 1.2 kb PstI-BglII fragment that contained the entire coding region of the AD109 dszB gene (FIGS. 2A–2C) into the polylinker plasmid pOK12. The resulting plasmid, designated pDA295, contained a unique XbaI site upstream of the dszB gene. In the second step, a 1.2 kb XbaI-BglII fragment from pDA295 that contained the entire dszB gene was cloned into the XbaI and BglII sites of pEBCtac, thus placing the AD109 dszB gene under the transcriptional control of the tac promoter. This plasmid, designated pDA296 and presented in FIG. 7, was introduced into *E. coli* DH10β for expression studies.

HPBS desulfinase assays (2 mg/ml protein) using cell-free lysates prepared from induced and uninduced cultures of DH10β/pDA296 were performed. In the absence of IPTG the cell-free lysate contained very little HPBS desulfinase activity. Only 22 nmoles of 2-HBP were produced during the G0 min. incubation period which corresponds to a specific activity of 0.2 (nmoles 2-HBP formed/min/mg protein). The lysate prepared from the IPTG-induced culture, however, had approximately 20 times more HPBS desulfinase activity (4.2 nmoles 2-HBP formed/min/mg protein) than the lysate prepared from the uninduced culture.

Equivalents

Those skilled in the art will know, or be able to ascertain, using no more than routine experimentation, many equivalents to the specific embodiments of the invention described herein. These and all other equivalents are intended to be encompassed by the following claims.

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 1362 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..1359

(xi) SEQUENCE DESCRIPTION: SEQ ID NO:1:

```
ATG ACC GAT CCA CGT CAG CTG CAC CTG GCC GGA TTC TTC TGT GCC GGC        48
Met Thr Asp Pro Arg Gln Leu His Leu Ala Gly Phe Phe Cys Ala Gly
 1               5                  10                  15

AAC GTC ACG CAC GCC CAC GGA GCG TGG CGC CAC GCC GAC GAC TCC AAC        96
Asn Val Thr His Ala His Gly Ala Trp Arg His Ala Asp Asp Ser Asn
                20                  25                  30

GGC TTC CTC ACC AAG GAG TAC TAC CAG CAG ATT GCC CGC ACG CTC GAG       144
Gly Phe Leu Thr Lys Glu Tyr Tyr Gln Gln Ile Ala Arg Thr Leu Glu
            35                  40                  45

CGC GGC AAG TTC GAC CTG CTG TTC CTT CCC GAC GCG CTC GCC GTG TGG       192
Arg Gly Lys Phe Asp Leu Leu Phe Leu Pro Asp Ala Leu Ala Val Trp
        50                  55                  60

GAC AGC TAC GGC GAC AAT CTG GAG ACC GGT CTG CGG TAT GGC GGG CAA       240
Asp Ser Tyr Gly Asp Asn Leu Glu Thr Gly Leu Arg Tyr Gly Gly Gln
65                  70                  75                  80

GGC GCG GTG ATG CTG GAG CCC GGC GTA GTT ATC GCC GCG ATG GCC TCG       288
Gly Ala Val Met Leu Glu Pro Gly Val Val Ile Ala Ala Met Ala Ser
                85                  90                  95

GTG ACC GAA CAT CTG GGG CTG GGC GCC ACC ATT TCC ACC ACC TAC TAC       336
Val Thr Glu His Leu Gly Leu Gly Ala Thr Ile Ser Thr Thr Tyr Tyr
```

-continued

| | | | |
|---|---|---|---|
| CCG CCC TAC CAT GTA GCC CGG GTC GTC GCT TCG CTG GAC CAG CTG TCC<br>Pro Pro Tyr His Val Ala Arg Val Val Ala Ser Leu Asp Gln Leu Ser<br>           115                          120                      125 | 384 |
| TCC GGG CGA GTG TCG TGG AAC GTG GTC ACC TCG CTC AGC AAT GCA GAG<br>Ser Gly Arg Val Ser Trp Asn Val Val Thr Ser Leu Ser Asn Ala Glu<br>130                        135                      140 | 432 |
| GCG CGC AAC TTC GGC TTC GAT GAA CAT CTC GAC CAC GAT GCC CGC TAC<br>Ala Arg Asn Phe Gly Phe Asp Glu His Leu Asp His Asp Ala Arg Tyr<br>145                        150                      155                      160 | 480 |
| GAT CGC GCC GAT GAA TTC CTC GAG GTC GTG CGC AAG CTC TGG AAC AGC<br>Asp Arg Ala Asp Glu Phe Leu Glu Val Val Arg Lys Leu Trp Asn Ser<br>           165                          170                      175 | 528 |
| TGG GAT CGC GAT GCG CTG ACA CTC GAC AAG GCA ACC GGC CAG TTC GCC<br>Trp Asp Arg Asp Ala Leu Thr Leu Asp Lys Ala Thr Gly Gln Phe Ala<br>                  180                      185                      190 | 576 |
| GAT CCG GCT AAG GTG CGC TAC ATC GAC CAC CGC GGC GAA TGG CTC AAC<br>Asp Pro Ala Lys Val Arg Tyr Ile Asp His Arg Gly Glu Trp Leu Asn<br>           195                          200                      205 | 624 |
| GTA CGC GGG CCG CTT CAG GTG CCG CGC TCC CCC CAG GGC GAG CCT GTC<br>Val Arg Gly Pro Leu Gln Val Pro Arg Ser Pro Gln Gly Glu Pro Val<br>      210                      215                      220 | 672 |
| ATT CTG CAG GCC GGG CTT TCG GCG CGG GGC AAG CGC TTC GCC GGG CGC<br>Ile Leu Gln Ala Gly Leu Ser Ala Arg Gly Lys Arg Phe Ala Gly Arg<br>225                        230                      235                      240 | 720 |
| TGG GCG GAC GCG GTG TTC ACG ATT TCG CCC AAT CTG GAC ATC ATG CAG<br>Trp Ala Asp Ala Val Phe Thr Ile Ser Pro Asn Leu Asp Ile Met Gln<br>                  245                      250                      255 | 768 |
| GCC ACG TAC CGC GAC ATA AAG GCG CAG GTC GAG GCC GCC GGA CGC GAT<br>Ala Thr Tyr Arg Asp Ile Lys Ala Gln Val Glu Ala Ala Gly Arg Asp<br>           260                          265                      270 | 816 |
| CCC GAG CAG GTC AAG GTG TTT GCC GCG GTG ATG CCG ATC CTC GGC GAG<br>Pro Glu Gln Val Lys Val Phe Ala Ala Val Met Pro Ile Leu Gly Glu<br>                  275                      280                      285 | 864 |
| ACC GAG GCG ATC GCC AGG CAG CGT CTC GAA TAC ATA AAT TCG CTG GTG<br>Thr Glu Ala Ile Ala Arg Gln Arg Leu Glu Tyr Ile Asn Ser Leu Val<br>290                        295                      300 | 912 |
| CAT CCC GAA GTC GGG CTT TCT ACG TTG TCC AGC CAT GTC GGG GTC AAC<br>His Pro Glu Val Gly Leu Ser Thr Leu Ser Ser His Val Gly Val Asn<br>305                        310                      315                      320 | 960 |
| CTT GCC GAC TAT TCG CTC GAT ACC CCG CTG ACC GAG GTC CTG GGC GAT<br>Leu Ala Asp Tyr Ser Leu Asp Thr Pro Leu Thr Glu Val Leu Gly Asp<br>                  325                      330                      335 | 1008 |
| CTC GCC CAG CGC AAC GTG CCC ACC CAA CTG GGC ATG TTC GCC AGG ATG<br>Leu Ala Gln Arg Asn Val Pro Thr Gln Leu Gly Met Phe Ala Arg Met<br>           340                          345                      350 | 1056 |
| TTG CAG GCC GAG ACG CTG ACC GTG GGA GAA ATG GGC CGG CGT TAT GGC<br>Leu Gln Ala Glu Thr Leu Thr Val Gly Glu Met Gly Arg Arg Tyr Gly<br>                  355                      360                      365 | 1104 |
| GCC AAC GTG GGC TTC GTC CCG CAG TGG GCG GGA ACC CGC GAG CAG ATC<br>Ala Asn Val Gly Phe Val Pro Gln Trp Ala Gly Thr Arg Glu Gln Ile<br>           370                          375                      380 | 1152 |
| GCG GAC CTG ATC GAG ATC CAT TTC AAG GCC GGC GGC GCC GAT GGC TTC<br>Ala Asp Leu Ile Glu Ile His Phe Lys Ala Gly Gly Ala Asp Gly Phe<br>385                        390                      395                      400 | 1200 |
| ATC ATC TCG CCG GCG TTC CTG CCC GGA TCT TAC GAG GAA TTC GTC GAT<br>Ile Ile Ser Pro Ala Phe Leu Pro Gly Ser Tyr Glu Glu Phe Val Asp<br>                  405                      410                      415 | 1248 |
| CAG GTG GTG CCC ATC CTG CAG CAC CGC GGA CTG TTC CGC ACT GAT TAC | 1296 |

```
Gln Val Val Pro Ile Leu Gln His Arg Gly Leu Phe Arg Thr Asp Tyr
            420                 425                 430

GAA GGC CGC ACC CTG CGC AGC CAT CTG GGA CTG CGT GAA CCC GCA TAC       1344
Glu Gly Arg Thr Leu Arg Ser His Leu Gly Leu Arg Glu Pro Ala Tyr
            435                 440                 445

CTG GGA GAG TAC GCA TGA                                                1362
Leu Gly Glu Tyr Ala
    450
```

(2) INFORMATION FOR SEQ ID NO:2:

(i) SEQUENCE CHARACTERISTICS:
        (A) LENGTH: 453 amino acids
        (B) TYPE: amino acid
        (D) TOPOLOGY: linear (ii) MOLECULE TYPE: protein (xi) SEQUENCE DESCRIPTION: SEQ ID NO:2:

```
Met Thr Asp Pro Arg Gln Leu His Leu Ala Gly Phe Phe Cys Ala Gly
  1               5                  10                  15

Asn Val Thr His Ala His Gly Ala Trp Arg His Ala Asp Asp Ser Asn
             20                  25                  30

Gly Phe Leu Thr Lys Glu Tyr Tyr Gln Gln Ile Ala Arg Thr Leu Glu
             35                  40                  45

Arg Gly Lys Phe Asp Leu Leu Phe Leu Pro Asp Ala Leu Ala Val Trp
 50                  55                  60

Asp Ser Tyr Gly Asp Asn Leu Glu Thr Gly Leu Arg Tyr Gly Gly Gln
 65                  70                  75                  80

Gly Ala Val Met Leu Glu Pro Gly Val Val Ile Ala Ala Met Ala Ser
                 85                  90                  95

Val Thr Glu His Leu Gly Leu Gly Ala Thr Ile Ser Thr Thr Tyr Tyr
            100                 105                 110

Pro Pro Tyr His Val Ala Arg Val Ala Ser Leu Asp Gln Leu Ser
            115                 120                 125

Ser Gly Arg Val Ser Trp Asn Val Val Thr Ser Leu Ser Asn Ala Glu
130                 135                 140

Ala Arg Asn Phe Gly Phe Asp Glu His Leu Asp His Asp Ala Arg Tyr
145                 150                 155                 160

Asp Arg Ala Asp Glu Phe Leu Glu Val Val Arg Lys Leu Trp Asn Ser
                165                 170                 175

Trp Asp Arg Asp Ala Leu Thr Leu Asp Lys Ala Thr Gly Gln Phe Ala
                180                 185                 190

Asp Pro Ala Lys Val Arg Tyr Ile Asp His Arg Gly Glu Trp Leu Asn
            195                 200                 205

Val Arg Gly Pro Leu Gln Val Pro Arg Ser Pro Gln Gly Glu Pro Val
210                 215                 220

Ile Leu Gln Ala Gly Leu Ser Ala Arg Gly Lys Arg Phe Ala Gly Arg
225                 230                 235                 240

Trp Ala Asp Ala Val Phe Thr Ile Ser Pro Asn Leu Asp Ile Met Gln
                245                 250                 255

Ala Thr Tyr Arg Asp Ile Lys Ala Gln Val Glu Ala Ala Gly Arg Asp
            260                 265                 270

Pro Glu Gln Val Lys Val Phe Ala Ala Val Met Pro Ile Leu Gly Glu
            275                 280                 285

Thr Glu Ala Ile Ala Arg Gln Arg Leu Glu Tyr Ile Asn Ser Leu Val
290                 295                 300
```

```
His Pro Glu Val Gly Leu Ser Thr Leu Ser Ser His Val Gly Val Asn
305                 310                 315                 320

Leu Ala Asp Tyr Ser Leu Asp Thr Pro Leu Thr Glu Val Leu Gly Asp
            325                 330                 335

Leu Ala Gln Arg Asn Val Pro Thr Gln Leu Gly Met Phe Ala Arg Met
            340                 345                 350

Leu Gln Ala Glu Thr Leu Thr Val Gly Glu Met Gly Arg Arg Tyr Gly
            355                 360                 365

Ala Asn Val Gly Phe Val Pro Gln Trp Ala Gly Thr Arg Glu Gln Ile
            370                 375                 380

Ala Asp Leu Ile Glu Ile His Phe Lys Ala Gly Ala Asp Gly Phe
385                 390                 395                 400

Ile Ile Ser Pro Ala Phe Leu Pro Gly Ser Tyr Glu Phe Val Asp
                405                 410                 415

Gln Val Val Pro Ile Leu Gln His Arg Gly Leu Phe Arg Thr Asp Tyr
            420                 425                 430

Glu Gly Arg Thr Leu Arg Ser His Leu Gly Leu Arg Glu Pro Ala Tyr
            435                 440                 445

Leu Gly Glu Tyr Ala
    450

(2) INFORMATION FOR SEQ ID NO:3:

(i) SEQUENCE CHARACTERISTICS:
        (A) LENGTH: 1110 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1107

(xi) SEQUENCE DESCRIPTION: SEQ ID NO:3:

ATG ACG ACA GAC ATC CAC CCG GCG AGC GCC GCA TCG TCG CCG GCG GCG        48
Met Thr Thr Asp Ile His Pro Ala Ser Ala Ala Ser Ser Pro Ala Ala
1               5                   10                  15

CGC GCG ACG ATC ACC TAC AGC AAC TGC CCC GTG CCT AAT GCC CTG CTC        96
Arg Ala Thr Ile Thr Tyr Ser Asn Cys Pro Val Pro Asn Ala Leu Leu
                20                  25                  30

GCC GCG CTC GGC TCA GGT ATT CTG GAC AGT GCC GGG ATC ACA CTT GCC       144
Ala Ala Leu Gly Ser Gly Ile Leu Asp Ser Ala Gly Ile Thr Leu Ala
            35                  40                  45

CTG CTG ACC GGA AAG CAG GGC GAG GTG CAC TTC ACC TAC GAC CGA GAT       192
Leu Leu Thr Gly Lys Gln Gly Glu Val His Phe Thr Tyr Asp Arg Asp
        50                  55                  60

GAC TAC ACC CGC TTC GGC GGC GAG ATT CCG CCG CTG GTC AGC GAG GGA       240
Asp Tyr Thr Arg Phe Gly Gly Glu Ile Pro Pro Leu Val Ser Glu Gly
65                  70                  75                  80

CTG CGT GCG CCG GGG CGG ACC CGC CTG CTG GGA CTG ACG CCG GTG CTG       288
Leu Arg Ala Pro Gly Arg Thr Arg Leu Leu Gly Leu Thr Pro Val Leu
                85                  90                  95

GGC CGC TGG GGC TAC TTC GTC CGG GGC GAC AGC GCG ATC CGC ACC CCG       336
Gly Arg Trp Gly Tyr Phe Val Arg Gly Asp Ser Ala Ile Arg Thr Pro
            100                 105                 110

GCC GAT CTT GCC GGC CGC CGC GTC GGA GTA TCC GAT TCG GCC AGG AGG       384
Ala Asp Leu Ala Gly Arg Arg Val Gly Val Ser Asp Ser Ala Arg Arg
        115                 120                 125
```

-continued

```
ATA TTG ACC GGA AGG CTG GGC GAC TAC CGC GAA CTT GAT CCC TGG CGG     432
Ile Leu Thr Gly Arg Leu Gly Asp Tyr Arg Glu Leu Asp Pro Trp Arg
    130                 135                 140

CAG ACC CTG GTC GCG CTG GGG ACA TGG GAG GCG CGT GCC TTG CTG AGC     480
Gln Thr Leu Val Ala Leu Gly Thr Trp Glu Ala Arg Ala Leu Leu Ser
145                 150                 155                 160

ACG CTC GAG ACG GCG GGG CTT GGC GTC GGC GAC GTC GAG CTG ACG CGC     528
Thr Leu Glu Thr Ala Gly Leu Gly Val Gly Asp Val Glu Leu Thr Arg
                165                 170                 175

ATC GAG AAC CCG TTC GTC GAC GTG CCG ACC GAA CGA CTG CAT GCC GCC     576
Ile Glu Asn Pro Phe Val Asp Val Pro Thr Glu Arg Leu His Ala Ala
            180                 185                 190

GGC TCG CTC AAA GGA ACC GAC CTG TTC CCC GAC GTG ACC AGC CAG CAG     624
Gly Ser Leu Lys Gly Thr Asp Leu Phe Pro Asp Val Thr Ser Gln Gln
        195                 200                 205

GCC GCA GTC CTT GAG GAT GAG CGC GCC GAC GCC CTG TTC GCG TGG CTT     672
Ala Ala Val Leu Glu Asp Glu Arg Ala Asp Ala Leu Phe Ala Trp Leu
    210                 215                 220

CCC TGG GCG GCC GAG CTC GAG ACC CGC ATC GGT GCA CGG CCG GTC CTA     720
Pro Trp Ala Ala Glu Leu Glu Thr Arg Ile Gly Ala Arg Pro Val Leu
225                 230                 235                 240

GAC CTC AGC GCA GAC GAC CGC AAT GCC TAT GCG AGC ACC TGG ACG GTG     768
Asp Leu Ser Ala Asp Asp Arg Asn Ala Tyr Ala Ser Thr Trp Thr Val
                245                 250                 255

AGC GCC GAG CTG GTG GAC CGG CAG CCC GAA CTG GTG CAG CGG CTC GTC     816
Ser Ala Glu Leu Val Asp Arg Gln Pro Glu Leu Val Gln Arg Leu Val
            260                 265                 270

GAT GCC GTG GTG GAT GCA GGG CGG TGG GCC GAG GCC AAT GGC GAT GTC     864
Asp Ala Val Val Asp Ala Gly Arg Trp Ala Glu Ala Asn Gly Asp Val
        275                 280                 285

GTC TCC CGC CTG CAC GCC GAT AAC CTC GGT GTC AGT CCC GAA AGC GTC     912
Val Ser Arg Leu His Ala Asp Asn Leu Gly Val Ser Pro Glu Ser Val
    290                 295                 300

CGC CAG GGA TTC GGA GCC GAT TTT CAC CGC CGC CTG ACG CCG CGG CTC     960
Arg Gln Gly Phe Gly Ala Asp Phe His Arg Arg Leu Thr Pro Arg Leu
305                 310                 315                 320

GAC AGC GAT GCT ATC GCC ATC CTG GAG CGT ACT CAG CGG TTC CTG AAG    1008
Asp Ser Asp Ala Ile Ala Ile Leu Glu Arg Thr Gln Arg Phe Leu Lys
                325                 330                 335

GAT GCG AAC CTG ATC GAT CGG TCG TTG GCG CTC GAT CGG TGG GCT GCA    1056
Asp Ala Asn Leu Ile Asp Arg Ser Leu Ala Leu Asp Arg Trp Ala Ala
            340                 345                 350

CCT GAA TTC CTC GAA CAA AGT CTC TCA CGC CAG GTC GAA GGG CAG ATA    1104
Pro Glu Phe Leu Glu Gln Ser Leu Ser Arg Gln Val Glu Gly Gln Ile
        355                 360                 365

GCA TGA                                                            1110
Ala
```

(2) INFORMATION FOR SEQ ID NO:4:

(i) SEQUENCE CHARACTERISTICS:
        (A) LENGTH: 369 amino acids
        (B) TYPE: amino acid
        (D) TOPOLOGY: linear (ii) MOLECULE TYPE: protein (xi) SEQUENCE DESCRIPTION: SEQ ID NO:4:

```
Met Thr Thr Asp Ile His Pro Ser Ala Ala Ser Ser Pro Ala Ala
1               5                   10                  15
```

```
Arg Ala Thr Ile Thr Tyr Ser Asn Cys Pro Val Pro Asn Ala Leu Leu
             20                  25                  30

Ala Ala Leu Gly Ser Gly Ile Leu Asp Ser Ala Gly Ile Thr Leu Ala
         35                  40                  45

Leu Leu Thr Gly Lys Gln Gly Glu Val His Phe Thr Tyr Asp Arg Asp
         50                  55                  60

Asp Tyr Thr Arg Phe Gly Gly Glu Ile Pro Pro Leu Val Ser Glu Gly
 65              70                  75                      80

Leu Arg Ala Pro Gly Arg Thr Arg Leu Leu Gly Leu Thr Pro Val Leu
                 85                  90                  95

Gly Arg Trp Gly Tyr Phe Val Arg Gly Asp Ser Ala Ile Arg Thr Pro
             100                 105                 110

Ala Asp Leu Ala Gly Arg Arg Val Gly Val Ser Asp Ser Ala Arg Arg
         115                 120                 125

Ile Leu Thr Gly Arg Leu Gly Asp Tyr Arg Glu Leu Asp Pro Trp Arg
         130                 135                 140

Gln Thr Leu Val Ala Leu Gly Thr Trp Glu Ala Arg Ala Leu Leu Ser
145                 150                 155                 160

Thr Leu Glu Thr Ala Gly Leu Gly Val Gly Asp Val Glu Leu Thr Arg
                 165                 170                 175

Ile Glu Asn Pro Phe Val Asp Val Pro Thr Glu Arg Leu His Ala Ala
             180                 185                 190

Gly Ser Leu Lys Gly Thr Asp Leu Phe Pro Asp Val Thr Ser Gln Gln
             195                 200                 205

Ala Ala Val Leu Glu Asp Glu Arg Ala Asp Ala Leu Phe Ala Trp Leu
         210                 215                 220

Pro Trp Ala Ala Glu Leu Glu Thr Arg Ile Gly Ala Arg Pro Val Leu
225                 230                 235                 240

Asp Leu Ser Ala Asp Asp Arg Asn Ala Tyr Ala Ser Thr Trp Thr Val
                 245                 250                 255

Ser Ala Glu Leu Val Asp Arg Gln Pro Glu Leu Val Gln Arg Leu Val
             260                 265                 270

Asp Ala Val Val Asp Ala Gly Arg Trp Ala Glu Ala Asn Gly Asp Val
         275                 280                 285

Val Ser Arg Leu His Ala Asp Asn Leu Gly Val Ser Pro Glu Ser Val
290                 295                 300

Arg Gln Gly Phe Gly Ala Asp Phe His Arg Arg Leu Thr Pro Arg Leu
305                 310                 315                 320

Asp Ser Asp Ala Ile Ala Ile Leu Glu Arg Thr Gln Arg Phe Leu Lys
                 325                 330                 335

Asp Ala Asn Leu Ile Asp Arg Ser Leu Ala Leu Asp Arg Trp Ala Ala
                 340                 345                 350

Pro Glu Phe Leu Glu Gln Ser Leu Ser Arg Gln Val Glu Gly Gln Ile
             355                 360                 365

Ala (2) INFORMATION FOR SEQ ID NO:5:

(i) SEQUENCE CHARACTERISTICS:
        (A) LENGTH: 1236 base pairs
        (B) TYPE: nucleic acid
        (C) STRANDEDNESS: single
        (D) TOPOLOGY: linear (ii) MOLECULE TYPE: DNA (genomic)
```

(ix) FEATURE:
    (A) NAME/KEY: CDS
    (B) LOCATION: 1..1236

(xi) SEQUENCE DESCRIPTION: SEQ ID NO:5:

| | | | | | | | | | | | | | | | | |
|---|---|---|---|---|---|---|---|---|---|---|---|---|---|---|---|---|
| ATG | AAC | GAA | CTC | GTC | AAA | GAT | CTC | GGC | CTC | AAT | CGA | TCC | GAT | CCG | ATC | 48 |
| Met | Asn | Glu | Leu | Val | Lys | Asp | Leu | Gly | Leu | Asn | Arg | Ser | Asp | Pro | Ile | |
| 1 | | | | 5 | | | | | 10 | | | | | 15 | | |
| GGC | GCT | GTG | CGG | CGA | CTG | GCC | GCG | CAG | TGG | GGG | GCC | ACC | GCT | GTT | GAT | 96 |
| Gly | Ala | Val | Arg | Arg | Leu | Ala | Ala | Gln | Trp | Gly | Ala | Thr | Ala | Val | Asp | |
| | | | 20 | | | | | 25 | | | | | 30 | | | |
| CGG | GAC | CGG | GCC | GGC | GGA | TCG | GCA | ACC | GCC | GAA | CTC | GAT | CAA | CTG | CGC | 144 |
| Arg | Asp | Arg | Ala | Gly | Gly | Ser | Ala | Thr | Ala | Glu | Leu | Asp | Gln | Leu | Arg | |
| | | 35 | | | | | 40 | | | | | 45 | | | | |
| GGC | AGC | GGC | CTG | CTC | TCG | CTG | TCC | ATT | CCC | GCC | GCA | TAT | GGC | GGC | TGG | 192 |
| Gly | Ser | Gly | Leu | Leu | Ser | Leu | Ser | Ile | Pro | Ala | Ala | Tyr | Gly | Gly | Trp | |
| | 50 | | | | | 55 | | | | | 60 | | | | | |
| GGC | GCC | GAC | TGG | CCA | ACG | ACT | CTG | GAA | GTT | ATC | CGC | GAA | GTC | GCA | ACG | 240 |
| Gly | Ala | Asp | Trp | Pro | Thr | Thr | Leu | Glu | Val | Ile | Arg | Glu | Val | Ala | Thr | |
| 65 | | | | | 70 | | | | | 75 | | | | | 80 | |
| GTG | GAC | GGA | TCG | CTG | GCG | CAT | CTA | TTC | GGC | TAC | CAC | CTC | GGC | TGC | GTA | 288 |
| Val | Asp | Gly | Ser | Leu | Ala | His | Leu | Phe | Gly | Tyr | His | Leu | Gly | Cys | Val | |
| | | | | 85 | | | | | 90 | | | | | 95 | | |
| CCG | ATG | ATC | GAG | CTG | TTC | GGC | TCG | GCG | CCA | CAA | AAG | GAA | CGG | CTG | TAC | 336 |
| Pro | Met | Ile | Glu | Leu | Phe | Gly | Ser | Ala | Pro | Gln | Lys | Glu | Arg | Leu | Tyr | |
| | | | 100 | | | | | 105 | | | | | 110 | | | |
| CGC | CAG | ATC | GCA | AGC | CAT | GAT | TGG | CGG | GTC | GGG | AAT | GCG | TCG | AGC | GAA | 384 |
| Arg | Gln | Ile | Ala | Ser | His | Asp | Trp | Arg | Val | Gly | Asn | Ala | Ser | Ser | Glu | |
| | | | 115 | | | | | 120 | | | | | 125 | | | |
| AAC | AAC | AGC | CAC | GTG | CTC | GAG | TGG | AAG | CTT | GCC | GCC | ACC | GCC | GTC | GAT | 432 |
| Asn | Asn | Ser | His | Val | Leu | Glu | Trp | Lys | Leu | Ala | Ala | Thr | Ala | Val | Asp | |
| | 130 | | | | | 135 | | | | | 140 | | | | | |
| GAT | GGC | GGG | TTC | GTC | CTC | AAC | GGC | GCG | AAG | CAC | TTC | TGC | AGC | GGC | GCC | 480 |
| Asp | Gly | Gly | Phe | Val | Leu | Asn | Gly | Ala | Lys | His | Phe | Cys | Ser | Gly | Ala | |
| 145 | | | | | 150 | | | | | 155 | | | | | 160 | |
| AAA | AGC | TCC | GAC | CTG | CTC | ATC | GTG | TTC | GGC | GTG | ATC | CAG | GAC | GAA | TCC | 528 |
| Lys | Ser | Ser | Asp | Leu | Leu | Ile | Val | Phe | Gly | Val | Ile | Gln | Asp | Glu | Ser | |
| | | | | 165 | | | | | 170 | | | | | 175 | | |
| CCC | CTG | CGC | GGC | GCG | ATC | ATC | ACC | GCG | GTC | ATT | CCC | ACC | GAC | CGG | GCC | 576 |
| Pro | Leu | Arg | Gly | Ala | Ile | Ile | Thr | Ala | Val | Ile | Pro | Thr | Asp | Arg | Ala | |
| | | | 180 | | | | | 185 | | | | | 190 | | | |
| GGT | GTT | CAG | ATC | AAT | GAC | GAC | TGG | CGC | GCA | ATC | GGG | ATG | CGC | CAG | ACC | 624 |
| Gly | Val | Gln | Ile | Asn | Asp | Asp | Trp | Arg | Ala | Ile | Gly | Met | Arg | Gln | Thr | |
| | | | 195 | | | | | 200 | | | | | 205 | | | |
| GAC | AGC | GGC | AGC | GCC | GAA | TTT | CGC | GAC | GTC | CGA | GTC | TAC | CCA | GAC | GAG | 672 |
| Asp | Ser | Gly | Ser | Ala | Glu | Phe | Arg | Asp | Val | Arg | Val | Tyr | Pro | Asp | Glu | |
| | 210 | | | | | 215 | | | | | 220 | | | | | |
| ATC | TTG | GGG | GCA | CCA | AAC | TCA | GTC | GTT | GAG | GCG | TTC | GTG | ACA | AGC | AAC | 720 |
| Ile | Leu | Gly | Ala | Pro | Asn | Ser | Val | Val | Glu | Ala | Phe | Val | Thr | Ser | Asn | |
| 225 | | | | | 230 | | | | | 235 | | | | | 240 | |
| CGC | GGC | AGC | CTG | TGG | ACG | CCG | GCG | ATT | CAG | TCG | ATC | TTC | TCG | AAC | GTT | 768 |
| Arg | Gly | Ser | Leu | Trp | Thr | Pro | Ala | Ile | Gln | Ser | Ile | Phe | Ser | Asn | Val | |
| | | | | 245 | | | | | 250 | | | | | 255 | | |
| TAT | CTG | GGG | CTC | GCG | CGT | GGC | GCG | CTC | GAG | GCG | GCA | GCG | GAT | TAC | ACC | 816 |
| Tyr | Leu | Gly | Leu | Ala | Arg | Gly | Ala | Leu | Glu | Ala | Ala | Ala | Asp | Tyr | Thr | |
| | | | 260 | | | | | 265 | | | | | 270 | | | |
| CGG | ACC | CAG | AGC | CGC | CCC | TGG | ACA | CCC | GCC | GGC | GTG | GCG | AAG | GCG | ACA | 864 |
| Arg | Thr | Gln | Ser | Arg | Pro | Trp | Thr | Pro | Ala | Gly | Val | Ala | Lys | Ala | Thr | |
| | | | 275 | | | | | 280 | | | | | 285 | | | |
| GAG | GAT | CCC | CAC | ATC | ATC | GCC | ACC | TAC | GGT | GAA | CTG | GCG | ATC | GCG | CTC | 912 |

```
Glu Asp Pro His Ile Ile Ala Thr Tyr Gly Glu Leu Ala Ile Ala Leu
        290                 295                 300

CAG GGC GCC GAG GCG GCC GCG CGC GAG GTC GCG GCC CTG TTG CAA CAG         960
Gln Gly Ala Glu Ala Ala Ala Arg Glu Val Ala Ala Leu Leu Gln Gln
305                 310                 315                 320

GCG TGG GAC AAG GGC GAT GCG GTG ACG CCC GAA GAG CGC GGC CAG CTG        1008
Ala Trp Asp Lys Gly Asp Ala Val Thr Pro Glu Glu Arg Gly Gln Leu
                325                 330                 335

ATG GTG AAG GTT TCG GGT GTG AAG GCC CTC TCG ACG AAG GCC GCC CTC        1056
Met Val Lys Val Ser Gly Val Lys Ala Leu Ser Thr Lys Ala Ala Leu
                340                 345                 350

GAC ATC ACC AGC CGT ATT TTC GAG ACA ACG GGC TCG CGA TCG ACG CAT        1104
Asp Ile Thr Ser Arg Ile Phe Glu Thr Thr Gly Ser Arg Ser Thr His
                355                 360                 365

CCC AGA TAC GGA TTC GAT CGG TTC TGG CGT AAC ATC CGG ACT CAT ACG        1152
Pro Arg Tyr Gly Phe Asp Arg Phe Trp Arg Asn Ile Arg Thr His Thr
370                 375                 380

CTG CAC GAT CCG GTA TCG TAT AAA ATC GTC GAT GTG GGG AAC TAC ACG        1200
Leu His Asp Pro Val Ser Tyr Lys Ile Val Asp Val Gly Asn Tyr Thr
385                 390                 395                 400

CTC AAC GGG ACA TTC CCG GTT CCC GGA TTT ACG TCA                        1236
Leu Asn Gly Thr Phe Pro Val Pro Gly Phe Thr Ser
                405                 410

(2) INFORMATION FOR SEQ ID NO:6:

(i) SEQUENCE CHARACTERISTICS:
        (A) LENGTH: 412 amino acids
        (B) TYPE: amino acid
        (D) TOPOLOGY: linear (ii) MOLECULE TYPE: protein (xi) SEQUENCE DESCRIPTION: SEQ ID NO:6:

Met Asn Glu Leu Val Lys Asp Leu Gly Leu Asn Arg Ser Asp Pro Ile
1               5                   10                  15

Gly Ala Val Arg Arg Leu Ala Ala Gln Trp Gly Ala Thr Ala Val Asp
                20                  25                  30

Arg Asp Arg Ala Gly Gly Ser Ala Thr Ala Glu Leu Asp Gln Leu Arg
            35                  40                  45

Gly Ser Gly Leu Leu Ser Leu Ser Ile Pro Ala Ala Tyr Gly Gly Trp
        50                  55                  60

Gly Ala Asp Trp Pro Thr Thr Leu Glu Val Ile Arg Glu Val Ala Thr
65                  70                  75                  80

Val Asp Gly Ser Leu Ala His Leu Phe Gly Tyr His Leu Gly Cys Val
                85                  90                  95

Pro Met Ile Glu Leu Phe Gly Ser Ala Pro Gln Lys Glu Arg Leu Tyr
                100                 105                 110

Arg Gln Ile Ala Ser His Asp Trp Arg Val Gly Asn Ala Ser Ser Glu
            115                 120                 125

Asn Asn Ser His Val Leu Glu Trp Lys Leu Ala Ala Thr Ala Val Asp
        130                 135                 140

Asp Gly Gly Phe Val Leu Asn Gly Ala Lys His Phe Cys Ser Gly Ala
145                 150                 155                 160

Lys Ser Ser Asp Leu Leu Ile Val Phe Gly Val Ile Gln Asp Glu Ser
                165                 170                 175

Pro Leu Arg Gly Ala Ile Ile Thr Ala Val Ile Pro Thr Asp Arg Ala
                180                 185                 190
```

```
Gly Val Gln Ile Asn Asp Asp Trp Arg Ala Ile Gly Met Arg Gln Thr
            195                 200                 205
Asp Ser Gly Ser Ala Glu Phe Arg Asp Val Arg Val Tyr Pro Asp Glu
        210                 215                 220
Ile Leu Gly Ala Pro Asn Ser Val Val Glu Ala Phe Val Thr Ser Asn
225                 230                 235                 240
Arg Gly Ser Leu Trp Thr Pro Ala Ile Gln Ser Ile Phe Ser Asn Val
                245                 250                 255
Tyr Leu Gly Leu Ala Arg Gly Ala Leu Glu Ala Ala Asp Tyr Thr
                260                 265                 270
Arg Thr Gln Ser Arg Pro Trp Thr Pro Ala Gly Val Ala Lys Ala Thr
            275                 280                 285
Glu Asp Pro His Ile Ile Ala Thr Tyr Gly Glu Leu Ala Ile Ala Leu
    290                 295                 300
Gln Gly Ala Glu Ala Ala Arg Glu Val Ala Ala Leu Leu Gln Gln
305                 310                 315                 320
Ala Trp Asp Lys Gly Asp Ala Val Thr Pro Glu Glu Arg Gly Gln Leu
                325                 330                 335
Met Val Lys Val Ser Gly Val Lys Ala Leu Ser Thr Lys Ala Ala Leu
                340                 345                 350
Asp Ile Thr Ser Arg Ile Phe Glu Thr Thr Gly Ser Arg Ser Thr His
            355                 360                 365
Pro Arg Tyr Gly Phe Asp Arg Phe Trp Arg Asn Ile Arg Thr His Thr
    370                 375                 380
Leu His Asp Pro Val Ser Tyr Lys Ile Val Asp Val Gly Asn Tyr Thr
385                 390                 395                 400
Leu Asn Gly Thr Phe Pro Val Pro Gly Phe Thr Ser
                405                 410

(2) INFORMATION FOR SEQ ID NO:7:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

Thr Thr Asp Ile His Pro Ala Ser Ala Ala Ser Ser Pro Ala Ala Arg
1               5                   10                  15

Ala Thr Ile Thr Tyr Ser
            20

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ACNGAYATHC AYCCNGC                                                   17

(2) INFORMATION FOR SEQ ID NO:9:
```

-continued (i) SEQUENCE CHARACTERISTICS:
    (A) LENGTH: 453 amino acids
    (B) TYPE: amino acid
    (D) TOPOLOGY: linear (ii) MOLECULE TYPE: protein (xi) SEQUENCE DESCRIPTION: SEQ ID NO:9:

```
Met Thr Gln Gln Arg Gln Met His Leu Ala Gly Phe Phe Ser Ala Gly
 1               5                  10                  15

Asn Val Thr His Ala His Gly Ala Trp Arg His Thr Asp Ala Ser Asn
            20                  25                  30

Asp Phe Leu Ser Gly Lys Tyr Tyr Gln His Ile Ala Arg Thr Leu Glu
        35                  40                  45

Arg Gly Lys Phe Asp Leu Leu Phe Leu Pro Asp Gly Leu Ala Val Glu
    50                  55                  60

Asp Ser Tyr Gly Asp Asn Leu Asp Thr Gly Val Gly Leu Gly Gly Gln
65                  70                  75                  80

Gly Ala Val Ala Leu Glu Pro Ala Ser Val Val Ala Thr Met Ala Ala
                85                  90                  95

Val Thr Glu His Leu Gly Leu Gly Ala Thr Ile Ser Ala Thr Tyr Tyr
            100                 105                 110

Pro Pro Tyr His Val Ala Arg Val Phe Ala Thr Leu Asp Gln Leu Ser
        115                 120                 125

Gly Gly Arg Val Ser Trp Asn Val Val Thr Ser Leu Asn Asp Ala Glu
    130                 135                 140

Ala Arg Asn Phe Gly Ile Asn Gln His Leu Glu His Asp Ala Arg Tyr
145                 150                 155                 160

Asp Arg Ala Asp Glu Phe Leu Glu Ala Val Lys Lys Leu Trp Asn Ser
                165                 170                 175

Trp Asp Glu Asp Ala Leu Val Leu Asp Lys Ala Ala Gly Val Phe Ala
            180                 185                 190

Asp Pro Ala Lys Val His Tyr Val Asp His His Gly Glu Trp Leu Asn
        195                 200                 205

Val Arg Gly Pro Leu Gln Val Pro Arg Ser Pro Gln Gly Glu Pro Val
    210                 215                 220

Ile Leu Gln Ala Gly Leu Ser Pro Arg Gly Arg Arg Phe Ala Gly Lys
225                 230                 235                 240

Trp Ala Glu Ala Val Phe Ser Leu Ala Pro Asn Leu Glu Val Met Gln
                245                 250                 255

Ala Thr Tyr Gln Gly Ile Lys Ala Glu Val Asp Ala Ala Gly Arg Asp
            260                 265                 270

Pro Asp Gln Thr Lys Ile Phe Thr Ala Val Met Pro Val Leu Gly Glu
        275                 280                 285

Ser Gln Ala Val Ala Gln Glu Arg Leu Glu Tyr Leu Asn Ser Leu Val
    290                 295                 300

His Pro Glu Val Gly Leu Ser Thr Leu Ser Ser His Thr Gly Ile Asn
305                 310                 315                 320

Leu Ala Ala Tyr Pro Leu Asp Thr Pro Ile Lys Asp Ile Leu Arg Asp
                325                 330                 335

Leu Gln Asp Arg Asn Val Pro Thr Gln Leu His Met Phe Ala Ala Ala
            340                 345                 350

Thr His Ser Glu Glu Leu Thr Leu Ala Glu Met Gly Arg Arg Tyr Gly
        355                 360                 365

Thr Asn Val Gly Phe Val Pro Gln Trp Ala Gly Thr Gly Glu Gln Ile
```

```
              370                 375                 380
Ala Asp Glu Leu Ile Arg His Phe Glu Gly Gly Ala Ala Asp Gly Phe
385                 390                 395                 400

Ile Ile Ser Pro Ala Phe Leu Pro Gly Ser Tyr Asp Glu Phe Val Asp
                405                 410                 415

Gln Val Val Pro Val Leu Gln Asp Arg Gly Tyr Phe Arg Thr Glu Tyr
                420                 425                 430

Gln Gly Asn Thr Leu Arg Asp His Leu Gly Leu Arg Val Pro Gln Leu
            435                 440                 445

Gln Gly Gln Pro Ser
        450
```

(2) INFORMATION FOR SEQ ID NO:10:

(i) SEQUENCE CHARACTERISTICS:
        (A) LENGTH: 365 amino acids
        (B) TYPE: amino acid
        (D) TOPOLOGY: linear (ii) MOLECULE TYPE: protein (xi) SEQUENCE DESCRIPTION: SEQ ID NO:10:

```
Met Thr Ser Arg Val Asp Pro Ala Asn Pro Gly Ser Glu Leu Asp Ser
1               5                   10                  15

Ala Ile Arg Asp Thr Leu Thr Tyr Ser Asn Cys Pro Val Pro Asn Ala
                20                  25                  30

Leu Leu Thr Ala Ser Glu Ser Gly Phe Leu Asp Ala Ala Gly Ile Glu
            35                  40                  45

Leu Asp Val Leu Ser Gly Gln Gln Gly Thr Val His Phe Thr Tyr Asp
50                  55                  60

Gln Pro Ala Tyr Thr Arg Phe Gly Gly Glu Ile Pro Pro Leu Leu Ser
65                  70                  75                  80

Glu Gly Leu Arg Ala Pro Gly Arg Thr Arg Leu Leu Gly Ile Thr Pro
                85                  90                  95

Leu Leu Gly Arg Gln Gly Phe Phe Val Arg Asp Asp Ser Pro Ile Thr
                100                 105                 110

Ala Ala Ala Asp Leu Ala Gly Arg Arg Ile Gly Val Ser Ala Ser Ala
            115                 120                 125

Ile Arg Ile Leu Arg Gly Gln Leu Gly Asp Tyr Leu Glu Leu Asp Pro
130                 135                 140

Trp Arg Gln Thr Leu Val Ala Leu Gly Ser Trp Glu Ala Arg Ala Leu
145                 150                 155                 160

Leu His Thr Leu Glu His Gly Glu Leu Gly Val Asp Asp Val Glu Leu
                165                 170                 175

Val Pro Ile Ser Ser Pro Gly Val Asp Val Pro Ala Glu Gln Leu Glu
                180                 185                 190

Glu Ser Ala Thr Val Lys Gly Ala Asp Leu Phe Pro Asp Val Ala Arg
            195                 200                 205

Gly Gln Ala Ala Val Leu Ala Ser Gly Asp Val Asp Ala Leu Tyr Ser
210                 215                 220

Trp Leu Pro Trp Ala Gly Glu Leu Gln Ala Thr Gly Ala Arg Pro Val
225                 230                 235                 240

Val Asp Leu Gly Leu Asp Glu Arg Asn Ala Tyr Ala Ser Val Trp Thr
                245                 250                 255

Val Ser Ser Gly Leu Val Arg Gln Arg Pro Gly Leu Val Gln Arg Leu
                260                 265                 270
```

```
Val Asp Ala Ala Val Asp Ala Gly Leu Trp Ala Arg Asp His Ser Asp
        275                 280                 285

Ala Val Thr Ser Leu His Ala Ala Asn Leu Gly Val Ser Thr Gly Ala
        290                 295                 300

Val Gly Gln Gly Phe Gly Ala Asp Phe Gln Gln Arg Leu Val Pro Arg
305                 310                 315                 320

Leu Asp His Asp Ala Leu Ala Leu Leu Glu Arg Thr Gln Gln Phe Leu
                325                 330                 335

Leu Thr Asn Asn Leu Leu Gln Glu Pro Val Ala Leu Asp Gln Trp Ala
                340                 345                 350

Ala Pro Glu Phe Leu Asn Asn Ser Leu Asn Arg His Arg
        355                 360                 365

(2) INFORMATION FOR SEQ ID NO:11:

(i) SEQUENCE CHARACTERISTICS:
        (A) LENGTH: 417 amino acids
        (B) TYPE: amino acid
        (D) TOPOLOGY: linear (ii) MOLECULE TYPE: protein (xi) SEQUENCE DESCRIPTION: SEQ ID NO:11:

Met Thr Leu Ser Pro Glu Lys Gln His Val Arg Pro Arg Asp Ala Ala
  1               5                  10                  15

Asp Asn Asp Pro Val Ala Val Ala Arg Gly Leu Ala Glu Lys Trp Arg
                 20                  25                  30

Ala Thr Ala Val Glu Arg Asp Arg Ala Gly Gly Ser Ala Thr Ala Glu
         35                  40                  45

Arg Glu Asp Leu Arg Ala Ser Ala Leu Leu Ser Leu Leu Val Pro Arg
     50                  55                  60

Glu Tyr Gly Gly Trp Gly Ala Asp Trp Pro Thr Ala Ile Glu Val Val
 65                  70                  75                  80

Arg Glu Ile Ala Ala Ala Asp Gly Ser Leu Gly His Leu Phe Gly Tyr
                 85                  90                  95

His Leu Thr Asn Ala Pro Met Ile Glu Leu Ile Gly Ser Gln Glu Gln
                100                 105                 110

Glu Glu His Leu Tyr Thr Gln Ile Ala Gln Asn Asn Trp Trp Thr Gly
            115                 120                 125

Asn Ala Ser Ser Glu Asn Asn Ser His Val Leu Asp Trp Lys Val Ser
130                 135                 140

Ala Thr Pro Thr Glu Asp Gly Gly Tyr Val Leu Asn Gly Thr Lys His
145                 150                 155                 160

Phe Cys Ser Gly Ala Lys Gly Ser Asp Leu Leu Phe Val Phe Gly Val
                165                 170                 175

Val Gln Asp Asp Ser Pro Gln Gln Gly Ala Ile Ile Ala Ala Ala Ile
                180                 185                 190

Pro Thr Ser Arg Ala Gly Val Thr Pro Asn Asp Asp Trp Ala Ala Ile
                195                 200                 205

Gly Met Arg Gln Thr Asp Ser Gly Ser Thr Asp Phe His Asn Val Lys
210                 215                 220

Val Glu Pro Asp Glu Val Leu Gly Ala Pro Asn Ala Phe Val Leu Ala
225                 230                 235                 240

Phe Ile Gln Ser Glu Arg Gly Ser Leu Phe Ala Pro Ile Ala Gln Leu
                245                 250                 255
```

```
Ile Phe Ala Asn Val Tyr Leu Gly Ile Ala His Gly Ala Leu Asp Ala
            260                 265                 270

Ala Arg Glu Tyr Thr Arg Thr Gln Ala Arg Pro Trp Thr Pro Ala Gly
        275                 280                 285

Ile Gln Gln Ala Thr Glu Asp Pro Tyr Thr Ile Arg Ser Tyr Gly Glu
    290                 295                 300

Phe Thr Ile Ala Leu Gln Gly Asp Ala Ala Ala Arg Glu Ala Ala
305                 310                 315                 320

His Leu Leu Gln Thr Val Trp Asp Lys Gly Asp Ala Leu Thr Pro Glu
                325                 330                 335

Asp Arg Gly Glu Leu Met Val Lys Val Ser Gly Val Lys Ala Leu Ala
            340                 345                 350

Thr Asn Ala Ala Leu Asn Ile Ser Ser Gly Val Phe Glu Val Ile Gly
            355                 360                 365

Ala Arg Gly Thr His Pro Arg Tyr Gly Phe Asp Arg Phe Trp Arg Asn
        370                 375                 380

Val Arg Thr His Ser Leu His Asp Pro Val Ser Tyr Lys Ile Ala Asp
385                 390                 395                 400

Val Gly Lys His Thr Leu Asn Gly Gln Tyr Pro Ile Pro Gly Phe Thr
                405                 410                 415

Ser (2) INFORMATION FOR SEQ ID NO:12:

(i) SEQUENCE CHARACTERISTICS:
        (A) LENGTH: 4144 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GGTTCGAGAT CGATCTGACC GTCGAACCCG GCGCGGTTCA AACCATCCTC TGGGGCCTCT      60

TCTTGCACTT GACATAGGAA TCTCTACTAA ATAAATAGAT ATTTATTCGA CACTAAGTTC     120

GGTGATCAGG CCGACCGTGT GTCTCAAGTG CTCGCTCCGG GTTGCCACGA GCTAAAGCGC     180

GCGATGCTGG GGCGACAGCG CTAGGCATTG CGTTCCCTCA CACCAATGAT GAGATGATAC     240

GATGCGCATG ACCACTATCC GCACCTAGCA CGAAAGATCC GTGCATTTCG CGAATGCCAA     300

TGAAGAGGAC CGACGTACGG CAGCTTCCTA CGCTTTCGCG CCATCGTTCA TAGCCAAGGT     360

CTTTTCGACG CCGGTTCGCG TGGGCGACTG ACGGCGGTAG CGCCGCGACT ATTCGTTTCA     420

AACTCACGAG GATAAGAGCC TATGACCGAT CCACGTCAGC TGCACCTGGC CGGATTCTTC     480

TGTGCCGGCA ACGTCACGCA CGCCCACGGA GCGTGGCGCC ACGCCGACGA CTCCAACGGC     540

TTCCTCACCA AGGAGTACTA CCAGCAGATT GCCCGCACGC TCGAGCGCGG CAAGTTCGAC     600

CTGCTGTTCC TTCCCGACGC GCTCGCCGTG TGGGACAGCT ACGGCGACAA TCTGGAGACC     660

GGTCTGCGGT ATGGCGGGCA AGGCGCGGTG ATGCTGGAGC CCGGCGTAGT TATCGCCGCG     720

ATGGCCTCGG TGACCGAACA TCTGGGGCTG GCGCCACCA TTTCCACCAC CTACTACCCG     780

CCCTACCATG TAGCCCGGGT CGTCGCTTCG CTGGACCAGC TGTCCTCCGG GCGAGTGTCG     840

TGGAACGTGG TCACCTCGCT CAGCAATGCA GAGGCGCGCA ACTTCGGCTT CGATGAACAT     900

CTCGACCACG ATGCCCGCTA CGATCGCGCC GATGAATTCC TCGAGGTCGT GCGCAAGCTC     960

TGGAACAGCT GGGATCGCGA TGCGCTGACA CTCGACAAGG CAACCGGCCA GTTCGCCGAT    1020
```

-continued

```
CCGGCTAAGG TGCGCTACAT CGACCACCGC GGCGAATGGC TCAACGTACG CGGGCCGCTT      1080

CAGGTGCCGC GCTCCCCCCA GGGCGAGCCT GTCATTCTGC AGGCCGGGCT TTCGGCGCGG      1140

GGCAAGCGCT TCGCCGGGCG CTGGGCGGAC GCGGTGTTCA CGATTTCGCC CAATCTGGAC      1200

ATCATGCAGG CCACGTACCG CGACATAAAG GCGCAGGTCG AGGCCGCCGG ACGCGATCCC      1260

GAGCAGGTCA AGGTGTTTGC CGCGGTGATG CCGATCCTCG GCGAGACCGA GGCGATCGCC      1320

AGGCAGCGTC TCGAATACAT AAATTCGCTG GTGCATCCCG AAGTCGGGCT TCTACGTTG      1380

TCCAGCCATG TCGGGGTCAA CCTTGCCGAC TATTCGCTCG ATACCCCGCT GACCGAGGTC      1440

CTGGGCGATC TCGCCCAGCG CAACGTGCCC ACCCAACTGG GCATGTTCGC CAGGATGTTG      1500

CAGGCCGAGA CGCTGACCGT GGGAGAAATG GGCCGGCGTT ATGGCGCCAA CGTGGGCTTC      1560

GTCCCGCAGT GGGCGGGAAC CCGCGAGCAG ATCGCGGACC TGATCGAGAT CCATTTCAAG      1620

GCCGGCGGCG CCGATGGCTT CATCATCTCG CCGGCGTTCC TGCCCGGATC TTACGAGGAA      1680

TTCGTCGATC AGGTGGTGCC CATCCTGCAG CACCGCGGAC TGTTCCGCAC TGATTACGAA      1740

GGCCGCACCC TGCGCAGCCA TCTGGGACTG CGTGAACCCG CATACCTGGG AGAGTACGCA      1800

TGACGACAGA CATCCACCCG GCGAGCGCCG CATCGTCGCC GGCGGCGCGC GCGACGATCA      1860

CCTACAGCAA CTGCCCCGTG CCTAATGCCC TGCTCGCCGC GCTCGGCTCA GGTATTCTGG      1920

ACAGTGCCGG GATCACACTT GCCCTGCTGA CCGGAAAGCA GGGCGAGGTG CACTTCACCT      1980

ACGACCGAGA TGACTACACC CGCTTCGGCG GCGAGATTCC GCCGCTGGTC AGCGAGGGAC      2040

TGCGTGCGCC GGGGCGGACC CGCCTGCTGG GACTGACGCC GGTGCTGGGC CGCTGGGGCT      2100

ACTTCGTCCG GGGCGACAGC GCGATCCGCA CCCCGGCCGA TCTTGCCGGC CGCCGCGTCG      2160

GAGTATCCGA TTCGGCCAGG AGGATATTGA CCGGAAGGCT GGGCGACTAC CGCGAACTTG      2220

ATCCCTGGCG GCAGACCCTG GTCGCGCTGG GGACATGGGA GGCGCGTGCC TTGCTGAGCA      2280

CGCTCGAGAC GGCGGGGCTT GGCGTCGGCG ACGTCGAGCT GACGCGCATC GAGAACCCGT      2340

TCGTCGACGT GCCGACCGAA CGACTGCATG CCGCCGGCTC GCTCAAAGGA ACCGACCTGT      2400

TCCCCGACGT GACCAGCCAG CAGGCCGCAG TCCTTGAGGA TGAGCGCGCC GACGCCCTGT      2460

TCGCGTGGCT TCCCTGGGCG GCCGAGCTCG AGACCCGCAT CGGTGCACGG CCGGTCCTAG      2520

ACCTCAGCGC AGACGACCGC AATGCCTATG CGAGCACCTG GACGGTGAGC GCCGAGCTGG      2580

TGGACCGGCA GCCCGAACTG GTGCAGCGGC TCGTCGATGC CGTGGTGGAT GCAGGGCGGT      2640

GGGCCGAGGC CAATGGCGAT GTCGTCTCCC GCCTGCACGC CGATAACCTC GGTGTCAGTC      2700

CCGAAAGCGT CCGCCAGGGA TTCGGAGCCG ATTTTCACCG CCGCCTGACG CCGCGGCTCG      2760

ACAGCGATGC TATCGCCATC CTGGAGCGTA CTCAGCGGTT CCTGAAGGAT GCGAACCTGA      2820

TCGATCGGTC GTTGGCGCTC GATCGGTGGG CTGCACCTGA ATTCCTCGAA CAAAGTCTCT      2880

CACGCCAGGT CGAAGGGCAG ATAGCATGAA CGAACTCGTC AAAGATCTCG GCCTCAATCG      2940

ATCCGATCCG ATCGGCGCTG TGCGGCGACT GGCCGCGCAG TGGGGGGCCA CCGCTGTTGA      3000

TCGGACCGG GCCGGCGGAT CGGCAACCGC CGAACTCGAT CAACTGCGCG GCAGCGGCCT      3060

GCTCTCGCTG TCCATTCCCG CCGCATATGG CGGCTGGGGC GCCGACTGGC CAACGACTCT      3120

GGAAGTTATC CGCGAAGTCG CAACGGTGGA CGGATCGCTG GCGCATCTAT TCGGCTACCA      3180

CCTCGGCTGC GTACCGATGA TCGAGCTGTT CGGCTCGGCG CCACAAAAGG AACGGCTGTA      3240

CCGCCAGATC GCAAGCCATG ATTGGCGGGT CGGGAATGCG TCGAGCGAAA CAACAGCCA      3300

CGTGCTCGAG TGGAAGCTTG CCGCCACCGC CGTCGATGAT GGCGGGTTCG TCCTCAACGG      3360

CGCGAAGCAC TTCTGCAGCG GCGCCAAAAG CTCCGACCTG CTCATCGTGT TCGGCGTGAT      3420
```

-continued

```
CCAGGACGAA TCCCCCCTGC GCGGCGCGAT CATCACCGCG GTCATTCCCA CCGACCGGGC    3480

CGGTGTTCAG ATCAATGACG ACTGGCGCGC AATCGGGATG CGCCAGACCG ACAGCGGCAG    3540

CGCCGAATTT CGCGACGTCC GAGTCTACCC AGACGAGATC TTGGGGGCAC CAAACTCAGT    3600

CGTTGAGGCG TTCGTGACAA GCAACCGCGG CAGCCTGTGG ACGCCGGCGA TTCAGTCGAT    3660

CTTCTCGAAC GTTTATCTGG GGCTCGCGCG TGGCGCGCTC GAGGCGGCAG CGGATTACAC    3720

CCGGACCCAG AGCCGCCCCT GGACACCCGC CGGCGTGGCG AAGGCGACAG AGGATCCCCA    3780

CATCATCGCC ACCTACGGTG AACTGGCGAT CGCGCTCCAG GGCGCCGAGG CGGCCGCGCG    3840

CGAGGTCGCG GCCCTGTTGC AACAGGCGTG GGACAAGGGC GATGCGGTGA CGCCCGAAGA    3900

GCGCGGCCAG CTGATGGTGA AGGTTTCGGG TGTGAAGGCC CTCTCGACGA AGGCCGCCCT    3960

CGACATCACC AGCCGTATTT TCGAGACAAC GGGCTCGCGA TCGACGCATC CCAGATACGG    4020

ATTCGATCGG TTCTGGCGTA ACATCCGGAC TCATACGCTG CACGATCCGG TATCGTATAA    4080

AATCGTCGAT GTGGGGAACT ACACGCTCAA CGGGACATTC CCGGTTCCCG GATTTACGTC    4140

ATGA                                                                 4144
```

(2) INFORMATION FOR SEQ ID NO:13:

(i) SEQUENCE CHARACTERISTICS:
        (A) LENGTH: 4144 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
TCATGACGTA AATCCGGGAA CCGGGAATGT CCCGTTGAGC GTGTAGTTCC CCACATCGAC      60

GATTTTATAC GATACCGGAT CGTGCAGCGT ATGAGTCCGG ATGTTACGCC AGAACCGATC     120

GAATCCGTAT CTGGGATGCG TCGATCGCGA GCCCGTTGTC TCGAAAATAC GGCTGGTGAT     180

GTCGAGGGCG GCCTTCGTCG AGAGGGCCTT CACACCCGAA ACCTTCACCA TCAGCTGGCC     240

GCGCTCTTCG GGCGTCACCG CATCGCCCTT GTCCCACGCC TGTTGCAACA GGGCCGCGAC     300

CTCGCGCGCG GCCGCCTCGG CGCCCTGGAG CGCGATCGCC AGTTCACCGT AGGTGGCGAT     360

GATGTGGGGA TCCTCTGTCG CCTTCGCCAC GCCGGCGGGT GTCCAGGGGC GGCTCTGGGT     420

CCGGGTGTAA TCCGCTGCCG CCTCGAGCGC GCCACGCGCG AGCCCAGAT AAACGTTCGA     480

GAAGATCGAC TGAATCGCCG GCGTCCACAG GCTGCCGCGG TTGCTTGTCA CGAACGCCTC     540

AACGACTGAG TTTGGTGCCC CCAAGATCTC GTCTGGGTAG ACTCGGACGT CGCGAAATTC     600

GGCGCTGCCG CTGTCGGTCT GGCGCATCCC GATTGCGCGC CAGTCGTCAT TGATCTGAAC     660

ACCGGCCCGG TCGGTGGGAA TGACCGCGGT GATGATCGCG CCGCGCAGGG GGGATTCGTC     720

CTGGATCACG CCGAACACGA TGAGCAGGTC GGAGCTTTTG GCGCCGCTGC AGAAGTGCTT     780

CGCGCCGTTG AGGACGAACC CGCCATCATC GACGGCGGTG GCGGCAAGCT TCCACTCGAG     840

CACGTGGCTG TTGTTTTCGC TCGACGCATT CCCGACCCGC CAATCATGGC TTGCGATCTG     900

GCGGTACAGC CGTTCCTTTT GTGGCGCCGA GCCAACAGC TCGATCATCG GTACGCAGCC     960

GAGGTGGTAG CCGAATAGAT GCGCCAGCGA TCCGTCCACC GTTGCGACTT CGCGGATAAC    1020

TTCCAGAGTC GTTGGCCAGT CGGCGCCCCA GCCGCCATAT GCGGCGGGAA TGGACAGCGA    1080

GAGCAGGCCG CTGCCGCGCA GTTGATCGAG TTCGGCGGTT GCCGATCCGC CGGCCCGGTC    1140

CCGATCAACA GCGGTGGCCC CCCACTGCGC GGCCAGTCGC CGCACAGCGC CGATCGGATC    1200
```

```
GGATCGATTG AGGCCGAGAT CTTTGACGAG TTCGTTCATG CTATCTGCCC TTCGACCTGG    1260

CGTGAGAGAC TTTGTTCGAG GAATTCAGGT GCAGCCCACC GATCGAGCGC CAACGACCGA    1320

TCGATCAGGT TCGCATCCTT CAGGAACCGC TGAGTACGCT CCAGGATGGC GATAGCATCG    1380

CTGTCGAGCC GCGGCGTCAG GCGGCGGTGA AAATCGGCTC CGAATCCCTG GCGGACGCTT    1440

TCGGGACTGA CACCGAGGTT ATCGGCGTGC AGGCGGGAGA CGACATCGCC ATTGGCCTCG    1500

GCCCACCGCC CTGCATCCAC CACGGCATCG ACGAGCCGCT GCACCAGTTC GGGCTGCCGG    1560

TCCACCAGCT CGGCGCTCAC CGTCCAGGTG CTCGCATAGG CATTGCGGTC GTCTGCGCTG    1620

AGGTCTAGGA CCGGCCGTGC ACCGATGCGG GTCTCGAGCT CGGCCGCCCA GGGAAGCCAC    1680

GCGAACAGGG CGTCGGCGCG CTCATCCTCA AGGACTGCGG CCTGCTGGCT GGTCACGTCG    1740

GGGAACAGGT CGGTTCCTTT GAGCGAGCCG GCGGCATGCA GTCGTTCGGT CGGCACGTCG    1800

ACGAACGGGT TCTCGATGCG CGTCAGCTCG ACGTCGCCGA CGCCAAGCCC CGCCGTCTCG    1860

AGCGTGCTCA GCAAGGCACG CGCCTCCCAT GTCCCCAGCG CGACCAGGGT CTGCCGCCAG    1920

GGATCAAGTT CGCGGTAGTC GCCCAGCCTT CCGGTCAATA TCCTCCTGGC CGAATCGGAT    1980

ACTCCGACGC GGCGGCCGGC AAGATCGGCC GGGGTGCGGA TCGCGCTGTC GCCCCGGACG    2040

AAGTAGCCCC AGCGGCCCAG CACCGGCGTC AGTCCCAGCA GGCGGGTCCG CCCCGGCGCA    2100

CGCAGTCCCT CGCTGACCAG CGGCGGAATC TCGCCGCCGA AGCGGGTGTA GTCATCTCGG    2160

TCGTAGGTGA AGTGCACCTC GCCCTGCTTT CCGGTCAGCA GGGCAAGTGT GATCCCGGCA    2220

CTGTCCAGAA TACCTGAGCC GAGCGCGGCG AGCAGGGCAT TAGGCACGGG GCAGTTGCTG    2280

TAGGTGATCG TCGCGCGCGC CGCCGGCGAC GATGCGGCGC TCGCCGGGTG GATGTCTGTC    2340

GTCATGCGTA CTCTCCCAGG TATGCGGGTT CACGCAGTCC CAGATGGCTG CGCAGGGTGC    2400

GGCCTTCGTA ATCAGTGCGG AACAGTCCGC GGTGCTGCAG GATGGGCACC ACCTGATCGA    2460

CGAATTCCTC GTAAGATCCG GGCAGGAACG CCGGCGAGAT GATGAAGCCA TCGGCGCCGC    2520

CGGCCTTGAA ATGGATCTCG ATCAGGTCCG CGATCTGCTC GCGGGTTCCC GCCCACTGCG    2580

GGACGAAGCC CACGTTGGCG CCATAACGCC GGCCCATTTC TCCCACGGTC AGCGTCTCGG    2640

CCTGCAACAT CCTGGCGAAC ATGCCCAGTT GGGTGGGCAC GTTGCGCTGG GCGAGATCGC    2700

CCAGGACCTC GGTCAGCGGG GTATCGAGCG AATAGTCGGC AAGGTTGACC CCGACATGGC    2760

TGGACAACGT AGAAAGCCCG ACTTCGGGAT GCACCAGCGA ATTTATGTAT TCGAGACGCT    2820

GCCTGGCGAT CGCCTCGGTC TCGCCGAGGA TCGGCATCAC CGCGGCAAAC ACCTTGACCT    2880

GCTCGGGATC GCGTCCGGCG GCCTCGACCT GCGCCTTTAT GTCGCGGTAC GTGGCCTGCA    2940

TGATGTCCAG ATTGGGCGAA ATCGTGAACA CCGCGTCCGC CCAGCGCCCG GCGAAGCGCT    3000

TGCCCCGCGC CGAAAGCCCG GCCTGCAGAA TGACAGGCTC GCCCTGGGGG GAGCGCGGCA    3060

CCTGAAGCGG CCCGCGTACG TTGAGCCATT CGCCGCGGTG GTCGATGTAG CGCACCTTAG    3120

CCGGATCGGC GAACTGGCCG GTTGCCTTGT CGAGTGTCAG CGCATCGCGA TCCCAGCTGT    3180

TCCAGAGCTT GCGCACGACC TCGAGGAATT CATCGGCGCG ATCGTAGCGG GCATCGTGGT    3240

CGAGATGTTC ATCGAAGCCG AAGTTGCGCG CCTCTGCATT GCTGAGCGAG GTGACCACGT    3300

TCCACGACAC TCGCCCGGAG GACAGCTGGT CCAGCGAAGC GACGACCCGG GCTACATGGT    3360

AGGGCGGGTA GTAGGTGGTG GAAATGGTGG CGCCCAGCCC CAGATGTTCG GTCACCGAGG    3420

CCATCGCGGC GATAACTACG CCGGGCTCCA GCATCACCGC GCCTTGCCCG CCATACCGCA    3480

GACCGGTCTC CAGATTGTCG CCGTAGCTGT CCCACACGGC GAGCGCGTCG GGAAGGAACA    3540
```

-continued

| | | | | | |
|---|---|---|---|---|---|
| GCAGGTCGAA | CTTGCCGCGC | TCGAGCGTGC | GGGCAATCTG | CTGGTAGTAC | TCCTTGGTGA | 3600 |
| GGAAGCCGTT | GGAGTCGTCG | GCGTGGCGCC | ACGCTCCGTG | GGCGTGCGTG | ACGTTGCCGG | 3660 |
| CACAGAAGAA | TCCGGCCAGG | TGCAGCTGAC | GTGGATCGGT | CATAGGCTCT | TATCCTCGTG | 3720 |
| AGTTTGAAAC | GAATAGTCGC | GGCGCTACCG | CCGTCAGTCG | CCCACGCGAA | CCGGCGTCGA | 3780 |
| AAAGACCTTG | GCTATGAACG | ATGGCGCGAA | AGCGTAGGAA | GCTGCCGTAC | GTCGGTCCTC | 3840 |
| TTCATTGGCA | TTCGCGAAAT | GCACGGATCT | TTCGTGCTAG | GTGCGGATAG | TGGTCATGCG | 3900 |
| CATCGTATCA | TCTCATCATT | GGTGTGAGGG | AACGCAATGC | CTAGCGCTGT | CGCCCCAGCA | 3960 |
| TCGCGCGCTT | TAGCTCGTGG | CAACCCGGAG | CGAGCACTTG | AGACACACGG | TCGGCCTGAT | 4020 |
| CACCGAACTT | AGTGTCGAAT | AAATATCTAT | TTATTTAGTA | GAGATTCCTA | TGTCAAGTGC | 4080 |
| AAGAAGAGGC | CCCAGAGGAT | GGTTTGAACC | GCGCCGGGTT | CGACGGTCAG | ATCGATCTCG | 4140 |
| AACC | | | | | | 4144 |

We claim:

1. A nucleotide molecule encoding an enzyme having an amino acid sequence set forth in SEQ ID NO: 2; or an enzymatically active fragment thereof.

2. The nucleotide molecule of claim 2 having the sequence set forth in SEQ ID NO: 1.

3. A nucleotide molecule encoding an enzyme having an amino acid sequence set forth in SEQ ID NO: 4; or an enzymatically active fragment thereof.

4. The nucleotide molecule of claim 3 having the sequence set forth in SEQ ID NO: 3.

5. A nucleotide molecule encoding an enzyme having an amino acid sequence set forth in SEQ ID NO: 6; or an enzymatically active fragment thereof.

6. The nucleotide molecule of claim 5 having the sequence set forth in SEQ ID NO: 5.

7. A nucleic acid molecule comprising one or more nucleotide sequences selected from the group consisting of the sequence set forth in SEQ ID NO: 1, the sequence set forth in SEQ ID NO: 3 and the sequence set forth in SEQ ID NO: 5.

8. A nucleotide sequence comprising at least about 20 contiguous nucleotides from the sequence of SEQ ID NO.: 1, or the complement thereof.

9. The nucleotide sequence of claim 8 comprising at least about 40 contiguous nucleotides from the sequence of SEQ ID NO.: 1 or the complement thereof.

10. The nucleotide sequence of claim 8 comprising at least about 50 contiguous nucleotides from the sequence of SEQ ID NO.: 1 or the complement thereof.

11. A nucleotide sequence comprising at least about 20 contiguous nucleotides from the sequence of SEQ ID NO.: 3, or the complement thereof.

12. The nucleotide sequence of claim 11 comprising at least about 40 contiguous nucleotides from the sequence of SEQ ID NO.: 3 or the complement thereof.

13. The nucleotide sequence of claim 11 comprising at least about 50 contiguous nucleotides from the sequence of SEQ ID NO.: 3 or the complement thereof.

14. A nucleotide sequence comprising at least about 20 contiguous nucleotides from the sequence of SEQ ID NO.: 5, or the complement thereof.

15. The nucleotide sequence of claim 14 comprising at least about 40 contiguous nucleotides.

16. The nucleotide sequence of claim 14 comprising at least about 50 contiguous nucleotides.

17. An enzyme having the amino acid sequence set forth in SEQ ID NO: 2, or an enzymatically active fragment thereof.

18. The enzyme of claim 17, wherein said enzyme is isolated from a microorganism.

19. The enzyme of claim 18 wherein the microorganism is a Sphingomonas.

20. The enzyme of claim 19 wherein the microorganism is Sphingomonas sp. strain AD109.

21. The enzyme of claim 20 said enzyme or fragment thereof being substantially free of other Sphingomonas proteins.

22. An enzyme having substantially the amino acid sequence set forth in SEQ ID NO.: 4, or an enzymatically active fragment thereof.

23. The enzyme of claim 22, wherein said enzyme is isolated from a microorganism.

24. The enzyme of claim 23 wherein the microorganism is a Sphingomonas.

25. The enzyme of claim 24 wherein the microorganism is Sphingomonas sp. strain AD109.

26. The enzyme of claim 25 having a molecular weight of about 40,000 daltons.

27. An enzyme having the amino acid sequence set forth in SEQ ID NO: 4, or an enzymatically active fragment thereof, said enzyme or fragment thereof being substantially free of other Sphingomonas proteins.

28. An enzyme having the amino acid sequence set forth in SEQ ID NO: 6, or an enzymatically active fragment thereof.

29. The enzyme of claim 28, wherein said enzyme is isolated from a microorganism.

30. The enzyme of claim 29 wherein the microorganism is a Sphingomonas.

31. The enzyme of claim 30 wherein the microorganism is Sphingomonas sp. strain AD109.

32. An enzyme having the amino acid sequence set forth in SEQ ID NO: 6, or an enzymatically active fragment thereof, said enzyme being substantially free of other Sphingomonas proteins.

33. An enzyme comprising the amino acid sequence set forth in SEQ ID NO.: 2.

34. An enzyme comprising the amino acid sequence set forth in SEQ ID NO.: 4.

35. An enzyme comprising the amino acid sequence set forth in SEQ ID NO.: 6.

36. A Sphingomonas enzyme catalyzing the conversion of dibenzothiophene to dibenzothiophene-5,5-dioxide.

37. A Sphingomnonas enzyme catalyzing the conversion of dibenzothiophene-5,5-dioxide to 2-(2-hydroxyphenyl) benzenesulfinate.

38. A Sphingoinonas enzyme catalyzing the conversion of 2-(2-hydroxyphenyl) benzenesulfinate to 2-hydroxybiphenyl and inorganic sulfur.

39. A plasmid comprising a nucleic acid molecule of claim 1 operatively linked to a promoter.

40. A plasmid comprising a nucleic acid molecule of claim 3 operatively linked to a promoter.

41. A plasmid comprising a nucleic acid molecule of claim 5 operatively linked to a promoter.

42. A plasmid comprising a nucleotide molecule of claim 7 operatively linked to a promoter.

43. A transformed microorganism containing a recombinant DNA plasmid comprising a DNA molecule encoding an enzyme set forth in SEQ ID NO: 2, or an active fragment thereof.

44. A transformed microorganism containing a recombinant DNA plasmid comprising a DNA molecule encoding an enzyme set forth in SEQ ID NO: 4, or an active fragment thereof.

45. A transformed microorganism containing a recombinant DNA plasmid comprising a DNA molecule encoding an enzyme set forth in SEQ ID NO: 6, or an active fragment thereof.

46. A transformed microorganism containing a recombinant DNA plasmid comprising a DNA sequence encoding an enzyme set forth in SEQ ID NO: 2, or an active fragment thereof; a DNA sequence encoding an enzyme set forth in SEQ ID NO: 2, or an active fragment thereof; and a DNA sequence encoding an enzyme set forth in SEQ ID NO: 2, or an active fragment thereof.

* * * * *

UNITED STATES PATENT AND TRADEMARK OFFICE
CERTIFICATE OF CORRECTION

PATENT NO. : 6,133,016　　　　　　　　　　　　　　　　Page 1 of 1
DATED : October 17, 2000
INVENTOR(S) : Aldis Darzins and Gregory T. Mrachko It is certified that error appears in the above-identified patent and that said Letters Patent is hereby corrected as shown below:

Column 53, claim 2
Line 27, after "claim" delete 2 and insert --1-- therefor.

Signed and Sealed this

Third Day of July, 2001

*Attest:*

NICHOLAS P. GODICI
*Attesting Officer*　　　*Acting Director of the United States Patent and Trademark Office*